US008178713B2

(12) United States Patent
Miller et al.

(10) Patent No.: US 8,178,713 B2
(45) Date of Patent: May 15, 2012

(54) SULFUR-CONTAINING PHOSPHOLIPID DERIVATIVES

(75) Inventors: Andrew David Miller, London (GB); Michael R. Jørgensen, London (GB); Rolf Kristian Berge, Bønes (NO); Jon Skorve, Arnatveit (NO)

(73) Assignee: Pronovo Biopharma Norge AS, Lysaker (NO)

( * ) Notice: Subject to any disclaimer, the term of this patent is extended or adjusted under 35 U.S.C. 154(b) by 681 days.

(21) Appl. No.: 10/518,427

(22) PCT Filed: Jun. 16, 2003

(86) PCT No.: PCT/GB03/02582
§ 371 (c)(1),
(2), (4) Date: Sep. 30, 2005

(87) PCT Pub. No.: WO04/000854
PCT Pub. Date: Dec. 31, 2003

(65) Prior Publication Data
US 2006/0105987 A1    May 18, 2006

(30) Foreign Application Priority Data

Jun. 20, 2002 (GB) .................................. 0214267.7
Jul. 29, 2002 (GB) .................................. 0217506.5

(51) Int. Cl.
*C07C 69/34* (2006.01)
*G01N 33/92* (2006.01)
*A01N 37/02* (2006.01)
(52) U.S. Cl. ........................ 560/146; 436/71; 514/547
(58) Field of Classification Search .................. None
See application file for complete search history.

(56) References Cited

U.S. PATENT DOCUMENTS

| 3,910,790 | A | | 10/1975 | Lohmer et al. |
| 5,093,365 | A | | 3/1992 | Berge et al. |
| 5,151,534 | A | * | 9/1992 | Shroot et al. ............... 554/88 |
| 5,268,494 | A | | 12/1993 | Shroot et al. |
| 5,290,960 | A | | 3/1994 | Singh |
| 6,365,628 | B1 | | 4/2002 | Berge |
| 6,511,670 | B1 | | 1/2003 | Maignan et al. |
| 7,375,135 | B2 | | 5/2008 | Najib-Fruchart et al. |
| 2002/0188023 | A1 | * | 12/2002 | Jorgensen et al. ........... 514/552 |
| 2004/0219450 | A1 | * | 11/2004 | Fletcher et al. ............. 424/450 |
| 2007/0009608 | A1 | * | 1/2007 | Berge ............................ 424/523 |
| 2007/0015795 | A1 | * | 1/2007 | Berge ............................ 514/337 |

FOREIGN PATENT DOCUMENTS

| DE | 2 210 230 | | 9/1973 |
| EP | 0250994 | | 6/1987 |
| EP | 0345038 | | 5/1989 |
| EP | 0 342 115 | A1 | 11/1989 |
| EP | 0447553 | | 7/1990 |
| EP | 0 622 370 | A2 | 11/1994 |
| EP | 1 044 966 | A1 | 10/2000 |
| JP | S49-102616 | | 9/1974 |
| JP | 3-079659 | | 4/1991 |
| NO | 20001905 | | 10/2000 |
| WO | WO 93/21191 | A1 | 10/1993 |
| WO | WO 96/11908 | | 4/1996 |
| WO | 9703663 | | 2/1997 |
| WO | 9958120 | | 11/1999 |
| WO | 9958121 | | 11/1999 |
| WO | 9958122 | | 11/1999 |
| WO | 9958123 | | 11/1999 |
| WO | 0030444 | * | 6/2000 |
| WO | 0168582 | | 9/2001 |
| WO | 0203983 | | 1/2002 |
| WO | WO 02/26218 | | 4/2002 |
| WO | WO 02/43728 | | 6/2002 |
| WO | 03014073 | | 2/2003 |
| WO | WO 03/014073 | A1 | 2/2003 |

OTHER PUBLICATIONS

Goodman & Gilman's The Pharmacological Basis of Therapeutics. 10th ed. NY McGraw Hill 2001 p. 3.*
Ruoxin et al. Sulfur-substituted Phosphatidylethanolamines. J.Org. Chem. 1993, 58, 1952-1954.*
Lehninger et al., "Principles of Biochemistry", 2nd ed., 1993, Worth Publishers, Inc., pp. 246-251.*
Runquist et al., Biochimica et Biophysica Acta, Biomembranes (1988), 940(1), 10-2.*
Johnson et al., Journal of the American Chemical Society (1957), 79, 753-4.*
Database Caplus Chemical Abstracts Service, Columbus, Ohio, US; Database Accession No. 1989:227959, Abstract of Rezanka et al.,:"Preparative separation of algal polar lipids and of individual molecular species by high-performance liquid chromatography and their identification by gas chromatography-mass spectrometry" in Journal of Chromatography (19.*
Database Caplus Chemical Abstracts Service, Columbus, Ohio, US; Database Accession No. 1991:182027, Abstract of Liao et al.,:"Main fatty acids and triglyceride composition of kernel oil of lodes vitiginea" in Zhiwu Xuebao (1990), 32(6), 473-6.*
Notice of Allowance from copending U.S. Appl. No. 10/220,502 dated Oct. 25, 2010.
Abdi-Dezfuli, F. et al., "Effects of Saturated and Polyunsaturated Fatty Acids and Their 3-Thia Fatty Acid Analogues on MCF-7 Breast Cancer Cell Growth," *Ann. of NY Acad. Sci.* (1994) 744:306-309.
Abstract of Schwarz et al., *Bioinorganic Chemistry* (1973) 2(1):47-68, CAS online citation 80:10264.
Ayté, J. et al., "Rat mitochondrial and cytosolic 3-hydroxy-3-methylglutaryl-CoA synthases are encoded by two different genes," *PNAS* (1990) 87:3874-3878.

(Continued)

*Primary Examiner* — Karl J Puttlitz
(74) *Attorney, Agent, or Firm* — Finnegan, Henderson, Farabow, Garrett & Dunner, LLP

(57) ABSTRACT

The present invention provides a lipid compound comprising at least one non-polar moiety and a polar moiety, wherein each or at least one non-polar moiety is of the formula X—Y—Z—, wherein X is a hydrocarbyl chain, Y is selected from at least one of S, Se, $SO_2$, SO, and O, and Z is an optional hydrocarbyl group, wherein the polar moiety is of the formula —[C(O)]$_m$PHG, wherein PHG is a polar head group, and wherein m is the number of non-polar moieties.

25 Claims, No Drawings

OTHER PUBLICATIONS

Buist, P. H., et al., "Use of Sulfur as an Oxidant Detector," *Tetrahedron Lett.* (1988) 29(4):435-38.

Chomczynski, P. et al., "Single-Step Method of RNA Isolation by Acid Guanidinium Thiocyanate-Phenol-Chloroform Extraction," *Anal. Biochem.* (1987) 162:156-159.

Copending U.S. Appl. No. 10/220,502.

Delfino, J. M., et al., "Synthesis of a Bipolar Phosphatidylethanolamine: A Model Compound for a Membrane-Spanning Probe," *Tetrahedron Lett.* (1987) 28(21):2323-26.

Derwent English Abstract for DE 2 210 230, Derwent Week: 197338.
Derwent English Abstract for EP 1044966, Derwent Week: 200101.
Derwent English Abstract for EP 342115, Derwent Week: 198946.
Derwent English Abstract for NO 200001905, Derwent Week: 200101.

English language abstract of JP 3-079659, published on Apr. 4, 1991.
English translation of JP S49-102616, published on Sep. 27, 1974.

Esser, V. et al., "Cloning, Sequencing, and Expression of a cDNA Encoding Rat Liver Mitochondrial Carnitine Palmitoyltransferase I," *J. Biol. Chem.* (1993) 268(8):5817-5822.

Guo, Z., et al., "The Effect of Two-dimensional Ordering on Photoreactions of Long-chain Unsaturated Carboxylic Acids," *J. Chem. Soc., Chem. Commun.* (1991) 7:479-81.

Holm, C. et al., "Human adipose tissue hormone-sensitive lipase: identification and comparison with other species," *Biochimica et Biophysica Acta* (1989) 1006:193-197.

International Search Report for PCTNO01/00082 dated Jun. 19, 2001.

Koopmans, S. J. et al., "In vivo insulin responsiveness for glucose uptake and production at eu- and hypoglycemic levels in normal and diabetic rats," *Biochimica et. Biophysica Acta* (1992) 1115:230-238.

Kundu, A. et al., "Copper(II)/Tin(II) Reagent for Allylation, Propargylation, Alkynylation, and Benzylation of Deselenides: A Novel Bimetallic Reactivity," *Organometallics* (2000) 19(1):105-107.

Li, Ruoxin, et al., "Synthesis of Sulfur-Substituted Phosphatidylethanolamines and Inhibition of Protozoan Cyclopropane Fatty Acid Synthase," *Tetrahedron Lett.* (1993) 34(8):1279-82.

Manabe, S., "Enantioselective [2,3] Sigmatropic Rearrangment of α-Propargyloxyacetic Acids Mediate by BuLi-(−)-Sparteine Complex," *Chem. Pharm. Bull.* (1998) 46(2):335-336.

Markowitz, M. A. and Singh, A., "Microstructure formation properties of 1,2-bis(15-thi-pentacosa-10,12-diynoyl)-*sn*-3-phosphocholine: an acyl chain modified diacetylenic phospholipid," *Chemistry and Physics of Lipids* (1996) 84:65-74.

Marshall, J. A. et al., "Chiral Base-Induced [2,3] Wittig Rearrangement of Acyclic α-(Propargyloxy)acetic Acids and Smides," *J. Org. Chem.* (1992) 57(9):2747-2750.

Office Action from copending U.S. Appl. No. 10/220,502 dated Sep. 15, 2009.
Office Action from copending U.S. Appl. No. 10/220,502 dated Aug. 21, 2006.
Office Action from copending U.S. Appl. No. 10/220,502 dated Jan. 23, 2009.
Office Action from copending U.S. Appl. No. 10/220,502 dated Jun. 15, 2004.
Office Action from copending U.S. Appl. No. 10/220,502 dated Mar. 21, 2008.
Office Action from copending U.S. Appl. No. 10/220,502 dated Mar. 10, 2005.
Office Action from copending U.S. Appl. No. 10/220,502 dated May 15, 2007.
Office Action from copending U.S. Appl. No. 10/220,502 dated Nov. 30, 2005.

Pearl, M. B. et al., "Acetylenic Acids of *Alvaradoa amorphoides* Seed Oil," *Lipids* (1973) 8(11):627-630.

Peterson, U. et al., "Origin of membrane dipole potential: Contribution of the phospholipid fatty acid chains," *Chemistry and Physics of Lipids* (2002) 117:19-27.

Pinho e Melo, T. M. V. D. et al., "Intramolecular dipolar cycloaddition reaction of 5H,7H-thiazolo[3,4-c]oxazol-4-ium-1-olates: synthesis of chiral 1H-pyrrolo[1,2-c]thiazole derivatives," *J. Chem. Soc. Perkin Trans I* (1999) 1219-1223.

Sato, K. et al., "A Synthesis of Dihydrothiopyran-3-ones. The Intramolecular Cyclization of Allylthioglycolic Acid Chlorides," *J. Org. Chem.* (1971) 36(15):2077-2080.

Vaagenes, H. et al., "Early Modulation of Genes Encoding Peroxisomal and Mitochondrial β-Oxidation Enzymes by 3-Thia Fatty Acids," *Biochemical Pharmacology* (1998) 56:1571-1582.

Woeltje, K. F. et al., "Cloning, Sequencing, and Expression of a cDNA Encoding Rat Liver Mitochondrial Carnitine Palmitoyltransferase II," *J. Biol. Chem.* (1990) 265(18):10720-10725.

Wu, P. et al., "Effects of Chain Length and Sulphur Position of Thia Fatty Acids on Their Incorporation into Phospholipids in 7800 C1 Hepatoma Cells and Isolated Rat Hepatocytes, and Their Effects on Fatty Acid Composition of Phospholipids," *Biochemical Pharmacology* (1996) 51:751-758.

Yamamoto M. et al., "Cyclisation of Alkynecarboxylic Acids: Synthesis and Reactions of 6-Methylene-1,4-oxathian-2-ones and Their 4,4-Dioxides," *J. Chem. Research (S)* (1990) 12-13.

*J. Chem. Res. M* (1990) 273-281.

Final Office Action dated Sep. 25, 2008, in copending U.S. Appl. No. 10/220,502.

CAPLUS English Abstract of WO 03/014073 A1 Feb. 20, 2003.

Hasegawa, E. et al. "Polymerizable Glycerophosphocholines Containing Terminal 2,4-Hexadienyloxy Groups and Their Polymerized Vesicles," *Polymer Bulletin* (1986) 15(5): 397-403.

Inami, K. et al. "Synthesis of Lysophosphatidylserine with 19:4 Acyl Group, as a Novel Sodium-Potassium ATPase Inhibitor, in Relation to DLIS-2, an Endogenous Digoxin-like Substance," *Tetrahedron Letters* (1990) 31(28): 4033-4036.

Li, R. et al. "Sulfur-Substituted Phosphatidylethanolamines," *Journal of Organic Chemistry* (1993) 58(7): 1952-1954.

Markowitz, A.M. et al. "Microstructure formation properties of 1,2-bis(15-thia-pentacosa-10,12-diynoyl)-*sn*-3-phosphocholine: an acyl chain modified diacetylenic phospholipid," *Chemistry and Physics of Lipids* (1996) 84(1): 65-74.

Molleyres, L.P. et al. "Structural Studies on the Diglyceride-mediated Activation of Protein Kinase C," *The Journal of Biological Chemistry* (1988) 263(29): 14832-14838.

Tsujibo, H. et al. "Hypotensive Compounds Isolated from Alcohol Extract of the Unossified Horn of *Cervus elaphus* L. var. *xanthopygus* MILNE-EDWARG (Rokujo). I. Isolation of Lysophosphatidyl Choline as a Hypotensive Principle and Structure-Activity Study of Related Compounds," *Chemical & Pharmaceutical Bulletin* (1987) 35(2): 365-359.

Skrede et al., Thia fatty acids, metabolism and metabolic effects, Biochimica et Biophysica Acta 1344 (1997) 115-131.

Garras et al., Subcellular localisation and induction of NADH-sensitive acetyl-CoA hydrolase and propionyl-CoA hydrolase activities in rat liver under lipogenic conditions after treatment with sulfur-substituted fatty acids, Biochimica et Biophysica Acta 1255 (1995) 154-160.

Willumsen et al., Docosahexaenoic acid shows no triglyceride-lowering effects but increases the peroxisomal fatty acid oxidation in liver of rats, Journal of Lipid Research Vo. 34, (1993) 13-22.

Berge et al., Impact of Cytochrome P450 system on lipoprotein metabolism. Effect of abnormal fatty acids (3-thia fatty acids), Pharmac. Ther. vol. 61 (1994) 345-382.

Molleyres, Louis P., et al., Structural studies on the diglyceride-mediated activation of protein kinase C, Journal of Biological Chemistry (1998) 263(29), 14832-8.

Sharma, A. et al., An Efficient Derivation of the Versatile Chiron Antipode 1-tert-Butyldimethylsilylpenta-1, 4-diyn-3-ol: Application to the Synthesis of (15*E,R,R*)-Duryne, Journal of Organic Chemistry, (1998) 63(18), 6128-6131.

Horiike, M., et al. Synthesis of Insect Sex Pheromones and Their Homologues; (Z)-6-Alkenyl Acetates from the Wittig Reaction, Agric. Biol. Chem, (1978) 42(10), 1963-1965.

Jayasuriaya, N., et al., Design, Synthesis, and Activity of Membrane-Disrupting Bolaphiles, J. Am. Chem. Soc., (1990) 112, 5844-5850.

Hermetter, A., et al., A Facile Procedure for the Synthesis of Saturated Phosphatidylcholines, Chemistry and Physics of Lipids, (1981) 28, 111-115.

Wang, P., et al., Synthesis of Phospholipid-Inhibitor Conjugates by Enzymatic Transphosphatidylation with Phospholipase D, J. Am. Chem. Soc., (1993) 115, 10487-10491.

Bestmann, H., et al., Pheromones; 87. An Efficient Synthesis of (6E,11Z)-6,11-Hexadecadienyl Acetate and (6E,11Z)-6,11-Hexadecadienal: Female Sex Pheromone Components of *Antheraea pernyi* and *A. polyphemus* (Lepidoptera: Saturniidae), Synthesis, (1992) 1239-1241.

DeDuve, C., et al., Tissue Fractionation Studies, Biochem. J., (1955) 60 604-617.

Bremer, J., The Effect of Fasting on the Activity of Liver Carnitine Palmitoyltransferase and Its Inhibition by Malonyl-CoA, Biochimica et Biophysica Acta, (1981) 665 628-631.

Clinkenbeard, K.D., et al., Intracellular Localization of the 3-Hydroxy-3-methylglutaryl Coenzyme A Cycle Enzymes in Liver, The Journal of Biological Chemistry, (1975) 250(8) 3108-3116.

Small, G.M., et al., A sensitive spectrophotmetric assay for peroxisomal acyl-CoA oxidase, Biochem. J., (1985) 227 205-210.

Bartnik, Friedhelm, et al., "Film-forming, resorbable wound dressing containing oligomeric esters of lactic acid or glycolic acid", Chemical Abstracts, vol. 110(18) (1989) 401-402.

Kurii, Jun, et al., "Bleaching composition", Chemical Abstracts, vol. 115 (1991) 131.

Office Action from copending U.S. Appl. No. 10/220,502 dated Feb. 24, 2010.

Derwent English abstract for EP 0 250 994, WPI Acc No. 1988-000420.

International Search Report for International Application No. PCT/GB2003/002582 dated Sep. 12, 2003.

Peterson, U. et al., Origin of membrane dipole potential: Contribution of the phospholipid fatty acid chains, *Chemistry and Physics of Lipids* (2002) 19-27.

Peterson, U. et al., Origin of membrane dipole potential: Contribution of the phospholipid fatty acid chains, *Chemistry and Physics of Lipids* (2002) 19-27, Abstract showing Mar. 22, 2002 internet available date.

* cited by examiner

SULFUR-CONTAINING PHOSPHOLIPID DERIVATIVES

The present invention relates to a compound. In particular the present invention relates to a compound having pharmaceutical activity WO-A-01/68582 relates to fatty acid analogues. Further, WO-A-01/68582 relates to the use of the fatty acid analogues for the treatment and/or prevention of syndrome X, obesity, hypertension, fatty liver, diabetes, hyperglycaemia, hyperinsulinemia and stenosis. WO-A-01/68582 also relates to processes for the preparation of the novel fatty acid analogues.

As discussed in WO-A-01/68582, EP-A-0345038 describes the use of non-oxidizable fatty acid analogues of the formula; Alkyl-X—$CH_2$COOR wherein the alkyl is a saturated or unsaturated hydrocarbon chain of 8 to 22 carbon atoms, X represents a O, S, SO or $SO_2$, and R is hydrogen or a C1-C4 alkyl group, for the treatment of hyperlipaemic conditions and for the reducing the concentration of cholesterol and triglycerides in the blood of mammals.

WO-A-97/03663 (PCT/N095/00195) describes alkyl-S—$CH_2$COOR and alkyl-Se—$CH_2$COOR for the inhibition of the oxidative modification of LDL. Further, this application describes the use of the selenium-compound for the treatment of hyperlipaemic conditions and for reducing the concentration of cholesterol and trigylcerides.

WO-A-99/58121 (PCT/N099/00135), WO-A99/58122 (PCT/NO99/00136) and WO-A-99/58123 (PCT/N099/00149) describes fatty acid analogues of the formula (I) $CH_3$—$[CH_2]_m$-$[Xi\text{-}CH_2]_n$—COOR— wherein n is an integer from 1 to 12, wherein m is an integer from 0 to 23, wherein i is an odd number which indicates the position relative to COOR, wherein Xi independent of each other are selected from the group comprising O, S, SO, $SO_2$, Se and $CH_2$, and wherein R represents hydrogen or C1-C4 alkyl, with the proviso that at least one of the Xi is not $CH_2$, or a salt, prodrug or complex thereof. This formula comprises one or several X groups (preferably selenium and sulphur) in positions 3, 5, 7, 9, etc. Further, WO-A-99/58121, WO-A-99/58122 and WO-A-99/58123 describe several medicinal and nutritional applications.

WO-A-99/58121 describes the use of the fatty acid analogues for the treatment and/or prevention of obesity, hypertension, fatty liver and the multi metabolic syndrome termed metabolic syndrome or Syndrome X. Further, WO-A-99/58121 describes a method for the treatment or prevention of an obese or overweight condition, and a method for producing weigh loss or a reduction of the fat mass in a human or non-human animal. WO-A-99/58121 also describes a nutritional composition effective to reduce, or to prevent an increase in, the total body weight or the total body fat mass in a human or non-human animal, and also a method for the modification of the fat distribution and content of animals in order to improve the quality of the meat, or product such as milk and eggs.

WO-A-99/58122 describes use of fatty acid analogues for the treatment and/or prevention of diabetes (both type I and II), and a method for the treatment or prevention of hyperglycaemia, hyperinsulinemia and reduced sensitivity to insulin. A nutritional composition effective to reduce, or to prevent an increase in the concentration of glucose in the blood of a human or non-human animal is also disclosed, as is a method for reducing the concentration of glucose in the blood of a human or non-human animal.

WO-A-99/58123 describes the use of the fatty acid analogues for the treatment and/or prevention of primary and/or secondary stenosis, and/or a disease caused by procedural vascular trauma and/or pathological proliferation of smooth muscle cells, and/or an increased level of plasma homocystein.

Aspects of the invention are defined in the appended claims.

In one aspect the present invention provides a lipid compound comprising at least one non-polar moiety and a polar moiety, wherein each or at least one non-polar moiety is of the formula X—Y—Z—, wherein X is a hydrocarbyl chain, Y is selected from at least one of S, Se, $SO_2$, SO, and O, and Z is an optional hydrocarbyl group, wherein the polar moiety is of the formula —$[C(O)]_m$PHG, wherein PHG is a polar head group, and wherein m is the number of non-polar moieties.

In a further aspect the present invention provides a combination comprising a liposome and a compound according to the present invention or a micelle containing a compound according to the present invention.

In a further aspect the present invention provides a pharmaceutical composition comprising a compound according to the present invention or a combination according to the present invention optionally admixed with a pharmaceutically acceptable carrier, diluent, excipient or adjuvant In a further aspect the present invention provides use of a compound according to the present invention or a pharmaceutically acceptable salt thereof, or a combination according to the present invention in medicine.

In a further aspect the present invention provides use of a compound according to the present invention or a pharmaceutically acceptable salt thereof in the manufacture of a medicament for the treatment and/or prevention of a condition selected from syndrome X, obesity, hypertension, fatty liver, diabetes, hyperglycaemia, hyperinsulinemia and stenosis.

In a further aspect the present invention provides use of a compound according to the present invention or a pharmaceutically acceptable salt thereof in the manufacture of a medicament for lowering concentration of cholesterol and triglycerides in the blood of mammals and/or inhibiting the oxidative modification of low density lipoprotein.

In a further aspect the present invention provides a method for producing weigh loss or a reduction of the fat mass in a human or non-human animal in need thereof, comprising administering thereto an effective amount of a compound according to the present invention or a pharmaceutically acceptable salt thereof.

In a further aspect the present invention provides a nutritional composition comprising a compound according to the present invention and optionally a foodstuff.

We have identified new lipid derivatives, such as phospholipids derivatives, (and in particular phosphatidyl cholines (PCs) 1 and ethanolamines (PEs) 2), triacylglycerides (TAGs) and non-natural type lipids, that may be of use in various therapeutic applications.

1

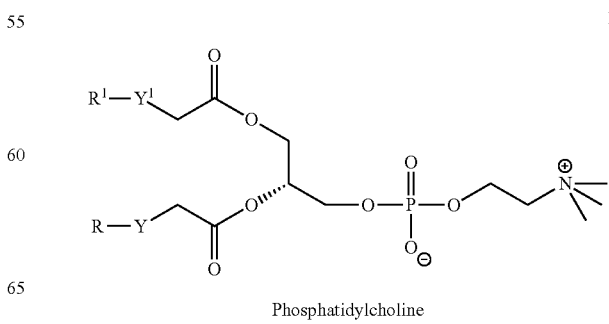

Phosphatidylcholine

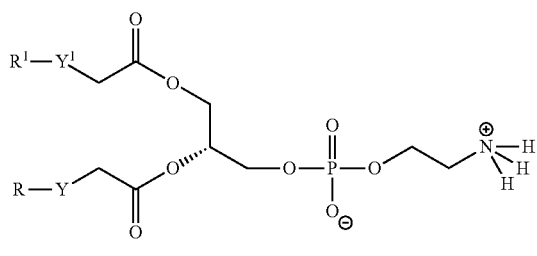

Phosphatidylethanolamine

Y = S, SO, SO$_2$, O, Se or CH$_2$
Y$^1$ = S, SO, SO$_2$, O, Se or CH$_2$
R = alkyl, alkenyl or alkynyl
R$^1$ = alkyl, alkenyl or alkynyl These lipids and phospholipids will incorporate the known[1a-d] sulphur fatty acid, tetradecylthioacetic acid (TTA, 3) as well as its unsaturated analogues, dTTA 4 and tTTA 5. It is understood that analogues which contain one of Se, SO, SO$_2$, O or CH$_2$ in place of sulphur will also provide useful pharmaceutical activity. In addition the length and degrees of saturation of the alkyl chains can also be varied.

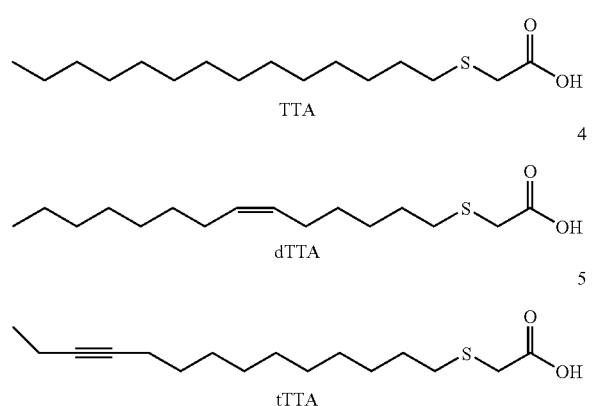

TTA is a modified fatty acid which has a number of powerful effects demonstrable both in vivo and in vitro on living organisms.[1a-d,2,3] It has properties very similar to natural fatty acids, the main difference being that TTA cannot be oxidised by the mitochondrial β-oxidation, but significantly increases the oxidation of other fatty acids. Despite the fact that TTA is not able to undergo β-oxidation, it is metabolised in most ways as a normal saturated fatty acid, but has a strong preference to being incorporated into phospholipids.[1a-d,2,3]

TTA affects antioxidant status at different levels by having the potential of changing the antioxidant defence system in addition to being an antioxidant itself through its free radical scavenging capacity. Addition of TTA may prevent the oxidative modification of LDL particles in plasma and reduce the generation of lipid peroxides.[1a-d,2,3]

The sulphur atom is more electronegative than carbon. Hence, the 3-thia acid is slightly more acidic than its corresponding fatty acid. Thia fatty acids are also more polar and slightly more soluble in water than fatty acids of corresponding chain length.

The parent fatty acids derivative used in the present novel compounds have one or more of the following therapeutic effects. This is confirmed by the reference given:

1) The treatment of hyperlipidaemic conditions and the reduction of concentration of cholesterol and triglycerides in the blood of mammals. Selenium analogues also show such properties as well as the inhibition of oxidative modification LDL.[4,5]
2) The treatment of and/or prevention of obesity, hypertention, fatty liver and multi metabolic syndrome (Syndrome X).[1b]
3) The treatment and/or the prevention of diabetes (Type I and II), hyperglycaemia, hyperinsulinemia, and reduced sensitivity to insulin.[1c]
4) The treatment and/or prevention of primary stenosis, secondary stenosis, and a disease caused by proceural vascular trauma and pathological proliferation of smooth muscle cells, and increase level of plasma homocystein.[1d]
5) The treatment and/or prevention of cancer. More specifically, treatment and/or prevention of primary and secondary neoplasms.[6]
6) The treatment and/or prevention of proliferative skin disorders (WO 02/26218)
7) The treatment and/or prevention of inflammatory disorders (WO 02/43728)

The fatty acid lipid derivatives of the present invention have corresponding therapeutic effects and/or biological properties.

For ease of reference, these and further aspects of the present invention are now discussed under appropriate section headings. However, the teachings under each section are not necessarily limited to each particular section.

PREFERABLE ASPECTS

Polar Moiety
Polar Head Group (PHG)

It will be appreciated by one of skill in the art that the polar head group may be derived from a suitable lipid. By the term "lipid" it may be meant a compound based on a fatty acids or a closely related compounds such as their corresponding alcohol or sphingosine base. It will be also be appreciated by one of skill in the art that the polar head group may be the polar head group of any suitable lipid.

In one preferred aspect the polar head group is derived from phospholipids, ceramides, triacylglycerols, lysophospholipids, phosphatidylserines, glycerols, alcohols, alkoxy compounds, monoacylglycerols, gangliosides, sphingomyelins, cerebrosides, phosphatidylcholines, phosphatidylethanolamines, phosphatidylinositols (PI), diacylglycerols, Phosphatidic acids, glycerocarbohydrates, polyalcohols and phosphatidylglycerols.

In one preferred aspect the polar head group is the polar head group of a lipid selected from phospholipids, ceramides, triacylglycerols, lysophospholipids, phosphatidylserines, glycerols, alcohols, alkoxy compounds, monoacylglycerols, gangliosides, sphingomyelins, cerebrosides, phosphatidylcholines, phosphatidylethanolamines, phosphatidylinositols (PI), diacylglycerols, Phosphatidic acids, glycerocarbohydrates, polyalcohols and phosphatidylglycerols.

In one preferred aspect the polar head group is derived from phospholipids, ceramides, triacylglycerols, lysophospholipids and phosphatidylserines.

In one preferred aspect the polar head group is the polar head group of a lipid selected from phospholipids, ceramides, triacylglycerols, lysophospholipids and phosphatidylserines.

Preferably the polar head group is derived from of a phospholipid.

Preferably the polar head group is the polar head group of a phospholipid.

Preferably the phospholipid is a neutral or anionic phospholipid.

In one preferred aspect the polar head group is derived from a phospholipid selected from a phosphatidylcholine (PC), a phosphatidylethanolamine (PE) such as Dioleoylphosphatidylcholine (DOPC) and Dioleoylphosphatidyl-ethanolamine (DOPE), and combinations thereof.

In one preferred aspect the polar head group is the polar head group of a phospholipid selected from a phosphatidylcholine (PC), a phosphatidylethanolamine (PE) such as Dioleoylphosphatidylcholine (DOPC) and Dioleoylphosphatidyl-ethanolamine (DOPE), and combinations thereof.

In one preferred aspect the polar head group is derived from a phospholipid selected from a phosphatidylcholine (PC), a phosphatidylethanolamine (PE) such as Dioleoylphosphatidyl-ethanolamine (DOPE), and combinations thereof.

In one preferred aspect the polar head group is the polar head group of a phospholipid selected from a phosphatidylcholine (PC), a phosphatidylethanolamine (PE) such as Dioleoylphosphatidyl-ethanolamine (DOPE), and combinations thereof.

In one preferred aspect the polar head group is a polar head group is selected from groups of the formula.

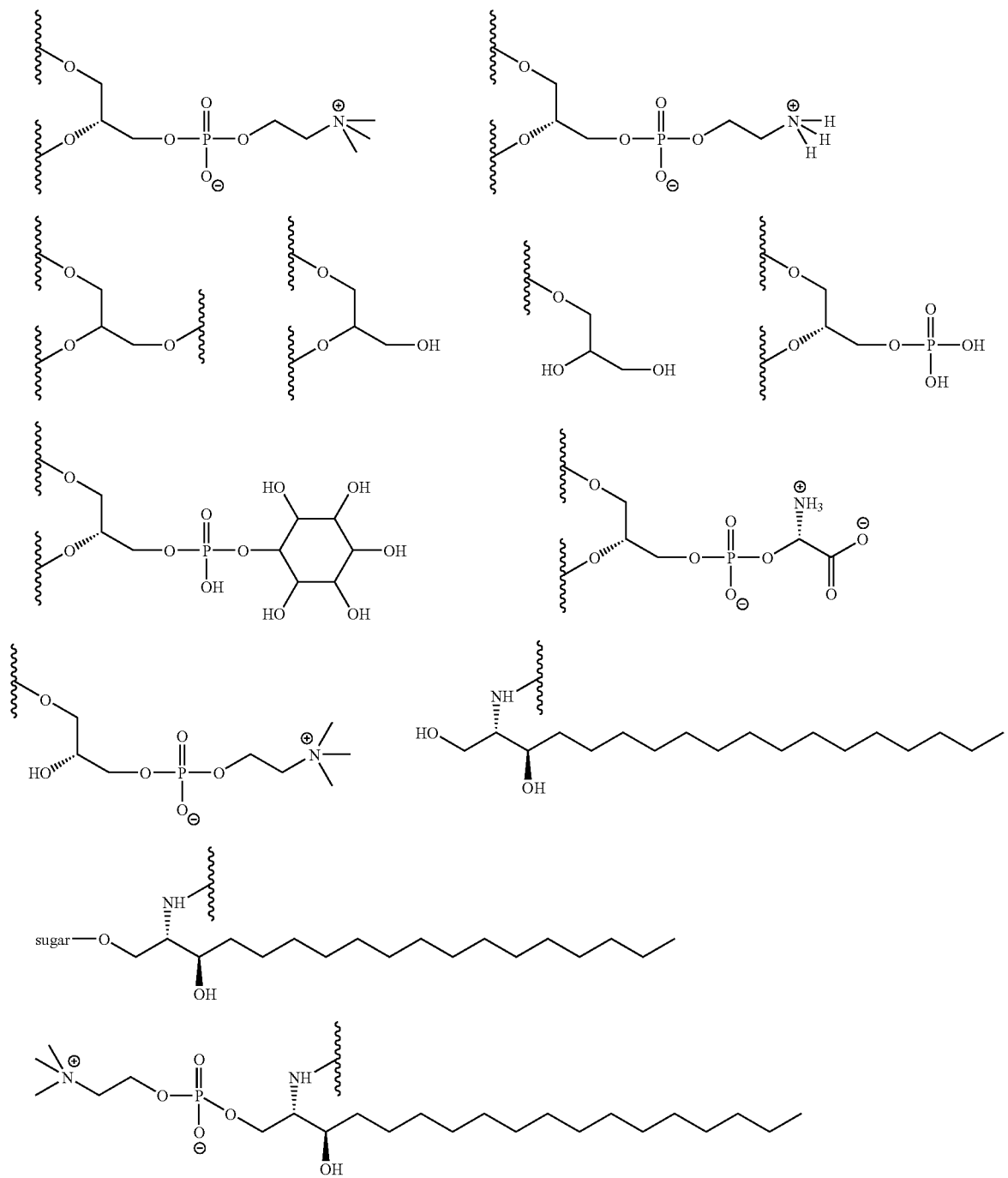

In one preferred aspect the polar head group is the polar head group is selected from groups of the formula.

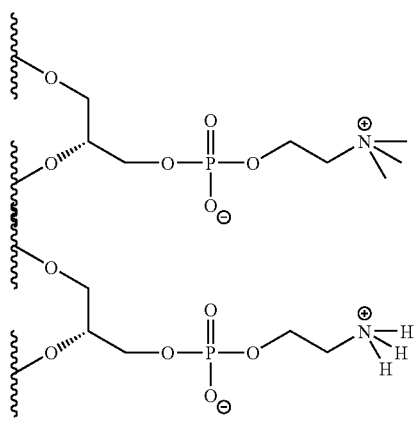

In one preferred aspect the polar head group is derived from of a triacyiglycerols.

In one preferred aspect the polar head group is the polar head group of a triacyiglycerols.

In one preferred aspect the polar head group is of the formula.

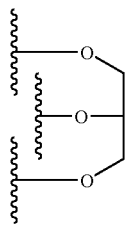

In one aspect the polar head group (PHG) may be the group -W-Linker-HG, wherein W is selected from $CH_2$, O, $NR^1$ and S, wherein $R^1$ is H or a hydrocarbyl group, wherein Linker is an optional linker group, and HG is a head group.

The head group (HG) may be polar or non-polar. When HG is non-polar it may be rendered polar by group —C(O)W-Linker-. Such head groups are encompassed by the present definition provided —C(O)W-Linker-HG is polar and HG is polar when attached to the —C(O)W-Linker- group.

In one aspect the head group (HG) may be an alkyl group. In this aspect preferably the alkyl contains at least 5 carbon, for example it is a $C_{5-100}$ alkyl group, a $C_{5-80}$ alkyl group, a $C_{5-60}$ alkyl group, a $C_{5-50}$ alkyl group, a $C_{5-40}$ alkyl group, $C_{5-30}$ alkyl group or a $C_{5-20}$ alkyl group.

In one aspect the head group (HG) is derived from phospholipids, ceramides, triacylglycerols, lysophospholipids, phosphatidylserines, glycerols, alcohols, alkoxy compounds, monoacylglycerols, gangliosides, sphingomyelins, cerebrosides, phosphatidylcholines, phosphatidylethanolamines, phosphatidylinositols (PI), diacylglycerols, Phosphatidic acids, glycerocarbohydrates, polyalcohols and phosphatidylglycerols.

In one preferred aspect the head group is the head group of a lipid selected from phospholipids, ceramides, triacylglycerols, lysophospholipids, phosphatidylserines, glycerols, alcohols, alkoxy compounds, monoacylglycerols, gangliosides, sphingomyelins, cerebrosides, phosphatidylcholines, phosphatidylethanolamines, phosphatidylinositols (PI), diacylglycerols, Phosphatidic acids, glycerocarbohydrates, polyalcohols and phosphatidylglycerols.

In one preferred aspect the head group is a head group is selected from groups of the formula.

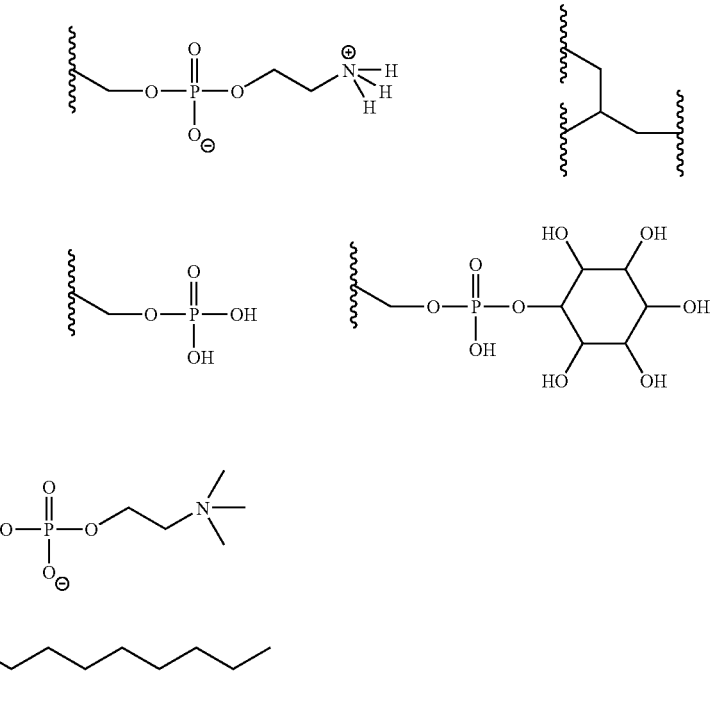

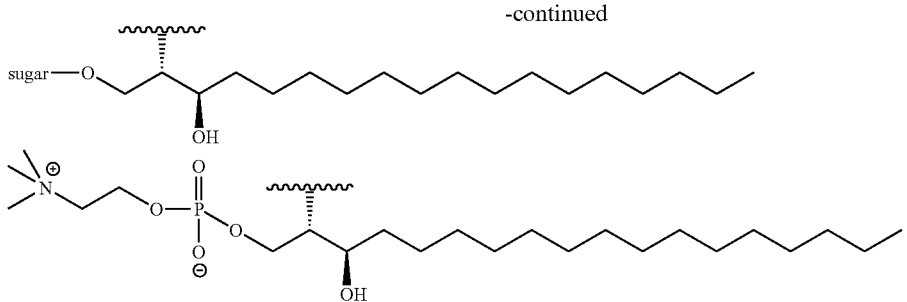

In one preferred aspect the head group is a head group is selected from groups of the formula.

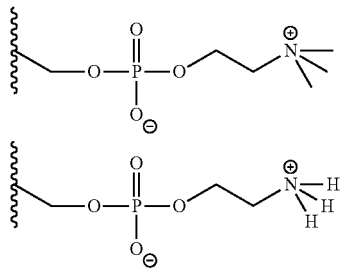

Linker

The linker of -W-Linker-HG may be any suitable group. A typical linker group is a hydrocarbyl group.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

The Linker is preferably, $C_{1-30}$, $C_{1-25}$, $C_{1-20}$, $C_{1-15}$, $C_{1-10}$, or $C_{1-5}$, hydrocarbyl group.

The Linker is preferably H, $C_{1-30}$, $C_{1-25}$, $C_{1-20}$, $C_{1-15}$, $C_{1-10}$, or $C_{1-5}$ hydrocarbon group.

The Linker is preferably $C_{1-30}$, $C_{1-25}$, $C_{1-20}$, $C_{1-15}$, $C_{1-10}$, or $C_{1-5}$ optionally substituted alkyl group.

The Linker is preferably $C_{1-30}$, $C_{1-25}$, $C_{1-20}$, $C_{1-15}$, $C_{1-10}$, or $C_{1-5}$, unsubstituted alkyl group.

In one preferred aspect at least one optional linker group is not present. In one preferred aspect no optional linker groups are present.

When one or more or all optional linker groups are not present, the group/compound from which the polar head group is derived is typically chosen to have one or more —OH groups. These allow a simple ester bond between the non-polar moiety and the polar moiety to be provided.

It will be appreciated by one skilled in the art that when an optional linker is present two or more W groups may or may not be bonded to the same atom of the linker. It is envisages that in some aspects the two or more W groups are boned to different atoms of a linker.

W

W of -W-Linker-HG is selected from $CH_2$, O, $NR^1$ and S, wherein $R^1$ is H or a hydrocarbyl group.

In one preferred aspect W is O or $NR^1$.

$R^1$ is preferably H or a hydrocarbon group.

$R^1$ is preferably H, $C_{1-30}$, $C_{1-25}$, $C_{1-20}$, $C_{1-15}$, $C_{1-10}$, $C_{1-5}$, or $C_{5-15}$ hydrocarbyl group.

$R^1$ is preferably H, $C_{1-30}$, $C_{1-25}$, $C_{1-20}$, $C_{1-15}$, $C_{1-10}$, $C_{1-5}$, or $C_{5-15}$ hydrocarbon group.

$R^1$ is preferably H, $C_{1-30}$, $C_{1-25}$, $C_{1-20}$, $C_{1-15}$, $C_{1-10}$, $C_{1-5}$, or $C_{5-15}$ optionally substituted alkyl group.

$R^1$ is preferably H, $C_{1-30}$, $C_{1-25}$, $C_{1-20}$, $C_{1-15}$, $C_{1-10}$, $C_{1-5}$, or $C_{5-15}$ unsubstituted alkyl group.

Non-Polar Moiety

As discussed above the present invention provides a lipid compound comprising at least one non-polar moiety and a polar moiety, wherein each or at least one non-polar moiety is of the formula X—Y—Z—, wherein X is a hydrocarbyl chain, Y is selected from at least one of S, Se, $SO_2$, SO, and O, and Z is an optional hydrocarbyl group, wherein the polar moiety is of the formula —$[C(O)]_m$PHG, wherein PHG is a polar head group, and wherein m is the number of non-polar moieties.

It will be appreciated that the present invention provides for lipids comprising more than one non-polar moiety, wherein at least one non-polar moiety is of the formula X—Y—Z—, (wherein X is a hydrocarbyl chain, Y is selected from at least one of S, Se, $SO_2$, SO, and O, and Z is an optional hydrocarbyl group) and one or more lipids which are not of this formula. In other words, the present compounds include lipids which have multiple non-polar moieties of which only one need meet the X—Y-Z requirement.

In one aspect the present invention may provide a lipid compound comprising at least two non-polar moieties and a polar moiety, wherein one non-polar moiety is of the formula X—Y—Z—, wherein one non-polar moiety is of the formula X—$CH_2$—Z—, wherein each X is independently a hydrocarbyl chain, Y is selected from at least one of S, Se, $SO_2$, SO, and O, and each Z is independently an optional hydrocarbyl group, wherein the chain X—$CH_2$—Z optionally and preferably contains an even number of atoms; wherein the polar moiety is of the formula —[C(O)]$_m$PHG, wherein PHG is a polar head group, and wherein m is the number of non-polar moieties.

It will be understood that the chain length of X—CH$_2$— is the longest chain of directly bonded atoms within moiety X—CH$_2$—It will be understood that a chain and consequently the chain length does not include atoms of cyclic substituents or substituents of a terminal carbon.

In a preferred aspect each non-polar moiety is of the formula X—Y—Z—, wherein X is a hydrocarbyl chain, Y is selected from at least one of S, Se, SO$_2$, SO, and O, and Z is an optional hydrocarbyl group.

X

As discussed above X is a hydrocarbyl chain: By "hydrocarbyl chain" it is meant a linear hydrocarbyl group.

In the following definitions of chain length it is meant the longest chain of directly bonded atoms within moiety X. It will be understood that a chain and consequently the chain length does not include atoms of cyclic substituents or substituents of a terminal carbon.

In one preferred aspect X is a group selected from optionally substituted alkyl, optionally substituted alkenyl and optionally substituted alkynyl.

In one preferred aspect X is a group selected from optionally substituted $C_6$-$C_{24}$ alkyl, optionally substituted $C_6$-$C_{24}$ alkenyl and optionally substituted $C_8$-$C_{24}$ alkynyl.

In one preferred aspect X is a group selected from optionally substituted alkyl having a chain length of 6 to 24 atoms, optionally substituted alkenyl having a chain length of 6 to 24 atoms and optionally substituted alkynyl having a chain length of 6 to 24 atoms.

In one preferred aspect X is a group selected from optionally substituted alkyl having a chain length of 10 to 18 atoms, optionally substituted alkenyl having a chain length of 10 to 18 atoms and optionally substituted alkynyl having a chain length of 10 to 18 atoms.

In one preferred aspect X is a group selected from optionally substituted alkyl having a chain length of 14 atoms, optionally substituted alkenyl having a chain length of 14 atoms and optionally substituted alkynyl having a chain length of 14 atoms.

In one preferred aspect X is a group selected from unsubstituted alkyl, unsubstituted alkenyl and unsubstituted alkynyl.

In one preferred aspect X is a group selected from unsubstituted $C_6$-$C_{24}$ alkyl, unsubstituted $C_6$-$C_{24}$ alkenyl and unsubstituted $C_6$-$C_{24}$ alkynyl.

In one preferred aspect X is a group selected from unsubstituted alkyl having a chain length of 6 to 24 atoms, unsubstituted alkenyl having a chain length of 6 to 24 atoms and unsubstituted alkynyl having a chain length of 6 to 24 atoms.

In one preferred aspect X is a group selected from unsubstituted $C_{10}$-$C_{18}$ alkyl, unsubstituted $C_{10}$-$C_{18}$ alkenyl and unsubstituted $C_{10}$-$C_{18}$ alkynyl.

In one preferred aspect X is a group selected from unsubstituted alkyl having a chain length of 10 to 18 atoms, unsubstituted alkenyl having a chain length of 10 to 18 atoms and unsubstituted alkynyl having a chain length of 10 to 18 atoms.

In one preferred aspect X is a group selected from unsubstituted $C_{14}$ alkyl, unsubstituted $C_{14}$ alkenyl and unsubstituted $C_{14}$ alkynyl.

In one preferred aspect X is a group selected from unsubstituted alkyl having a chain length of 14 atoms, unsubstituted alkenyl having a chain length of 14 atoms and unsubstituted alkynyl having a chain length of 14 atoms.

In one preferred aspect X is a hydrocarbon chain. By "hydrocarbon chain" it is meant a linear hydrocarbon group.

In one aspect X is selected from $C_6$-$C_{24}$ alkenyl containing one or more double bonds and optionally one or more triple bonds, $C_6$-$C_{24}$ alkynyl, $C_6$-$C_{24}$ alkyl optionally substituted with at least one of F, Cl, hydroxy, $C_1$-$C_4$ alkoxy, $C_1$-$C_4$ alkylthio, $C_2$-$C_5$ acyloxy and $C_1$-$C_4$ alkyl.

One skilled in the art will appreciate that alkynyl groups containing one or more alkenyl groups may be provided or alkenyl groups containing one or more alkynyl groups may be provided When X contains one or more double bonds, preferably at least one, more preferably each, is in cis configuration.

In one preferred aspect X is an acetylenic hydrocarbyl group. The term "acetylenic hydrocarbyl" as used herein means a group comprising at least C and H, having at least one —C≡C— bond and may optionally comprise one or more other suitable substituents. Examples of such substituents may include halo-, alkoxy-, nitro-, a hydrocarbon group, an N-acyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

In one preferred aspect X is an acetylenic hydrocarbyl group containing a single C≡C bond. It will be understood by one skilled in the art that by "X is an acetylenic hydrocarbyl group containing a single C≡C bond" it is meant the or each X contains one and only one C≡C bond.

In one preferred embodiment of the present invention, the acetylenic hydrocarbyl group is an alkynyl group.

In one preferred aspect X is a group selected from optionally substituted alkynyl groups having a chain length of 6 to 24 atoms.

In one preferred aspect X is a group selected from optionally substituted alkynyl groups having a chain length of 10 to 18 atoms.

In one preferred aspect X is a group selected from optionally substituted alkynyl groups having a chain length of 16 or 17 atoms.

In one preferred aspect X is a group selected from unsubstituted alkynyl groups.

In one preferred aspect X is a group selected unsubstituted $C_6$-$C_{24}$ alkynyl groups.

In one preferred aspect X is a group selected from unsubstituted alkynyl groups having a chain length of 6 to 24 atoms.

In one preferred aspect X is a group selected from unsubstituted $C_{10}$-$C_{18}$ alkynyl groups.

In one preferred aspect X is a group selected from unsubstituted alkynyl groups having a chain length of 10 to 18 atoms.

In one preferred aspect X is a group selected from unsubstituted $C_{16}$ or $C_{17}$ alkynyl groups.

In one preferred aspect X is a group selected from unsubstituted alkynyl having a chain length of 16 or 17 atoms.

In one preferred aspect the C≡C of the acetylenic hydrocarbyl group is distanced from the terminal end of the acetylenic hydrocarbyl group by from 2 to 15 carbons.

In one preferred aspect the C≡C of the acetylenic hydrocarbyl group is distanced from the terminal end of the acetylenic hydrocarbyl group by 2 carbons.

In one preferred aspect the C≡C of the acetylenic hydrocarbyl group is distanced from the terminal end of the acetylenic hydrocarbyl group by 3 carbons.

In one preferred aspect the C≡C of the acetylenic hydrocarbyl group is distanced from the terminal end of the acetylenic hydrocarbyl group by 7 carbons.

In one preferred aspect the C≡C of the acetylenic hydrocarbyl group is distanced from the terminal end of the acetylenic hydrocarbyl group by 13 carbons.

Y

In one preferred aspect at least one Y group is selected from S and Se.

In one preferred aspect Y is selected from S and Se. In other word, in one preferred aspect each Y is selected from S and Se.

In a highly preferred aspect at least one Y group is S.

In a highly preferred aspect Y is S. In other words, in a highly preferred aspect each Y is S.

In a further highly preferred aspect the compound of the present invention is of the formula

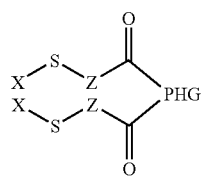

wherein groups X and Z are selected independently of each other.

In a further highly preferred aspect the compound of the present invention is of the formula

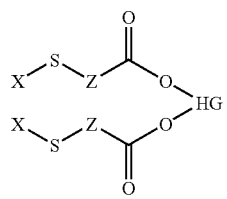

wherein groups X and Z are selected independently of each other.

Z

As discussed above Z is an optional hydrocarbyl group. In one aspect Z is present In one aspect Z is not present.

In one preferred aspect Z is an alkyl group.

In one preferred aspect Z is a $C_1$-$C_{10}$, preferably $C_1$-$C_6$, preferably $C_1$-$C_3$ alkyl group. Preferably Z is —$CH_2$—.

YZ

In one aspect Y and Z together may be formed by a unit which may repeat within the YZ moiety.

Preferably Y—Z together represent the group $[Y^1—CH_2]_n$, wherein $Y^1$ is selected from S, Se, $SO_2$, SO, and O, and wherein n is an integer from 1 to 20

In this aspect preferably $Y^1$ is selected from S and Se. Yet more preferably $Y^1$ is S.

Preferably n is from 1 to 10, more preferably from 1 to 5, more preferably 1, 2 or 3. In one highly preferred aspect n is 1.

In one aspect the compound is of the formula

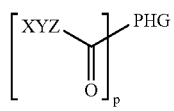

wherein p is at least 1, such as 1 to 1000, 1 to 1000, 1 to 100, 1 to 50, 1 to 20, 1 to 10, preferably 1 to 5, preferably 1, 2 or 3, and wherein each W, X, Y and Z is selected independently of each other.

Examples of suitable compounds from which the polar head group may be derived for given values of p are as follows

| p | |
|---|---|
| 1 | glycerols |
| | alcohols |
| | alkoxy compounds |
| | lysophospholipids |
| | monoacylglycerols |
| | gangliosides |
| | sphingomyelins |
| | cerebrosides |
| 2 | phosphatidylcholines (PC) |
| | phosphatidylethanolamines (PE), |
| | phosphatidylserines (PS) |
| | phosphatidylinositols (PI) |
| | diacylglycerols |
| | Phosphatidic acids |
| | glycerocarbohydrates |
| | phosphatidylglycerols |
| 3 | triacylglycerols |
| 1 or more | polyalcohols |

In one aspect the compound is of the formula

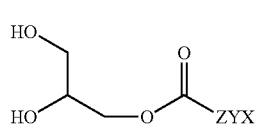 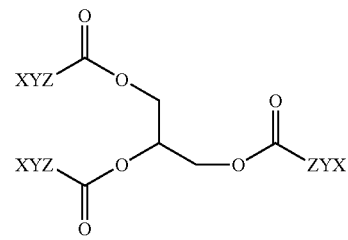 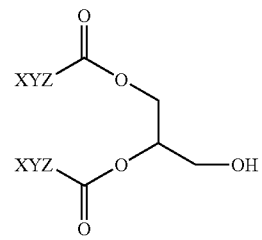

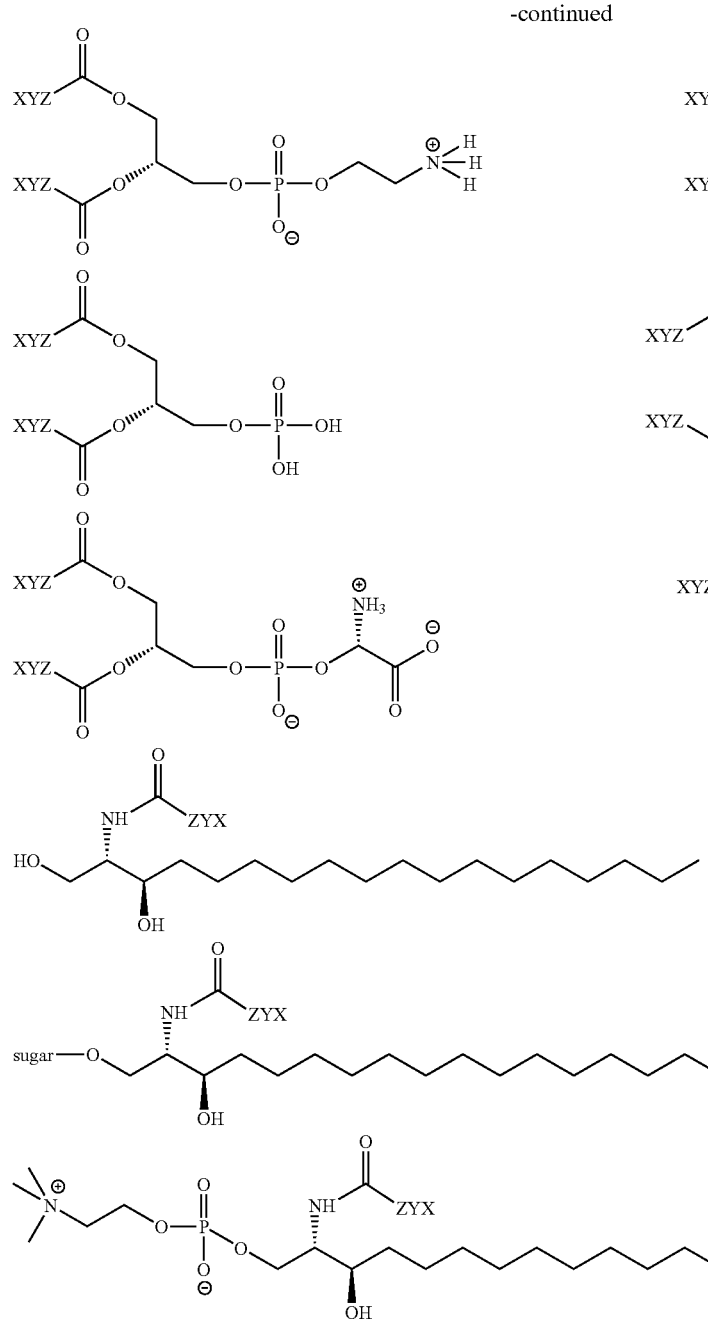
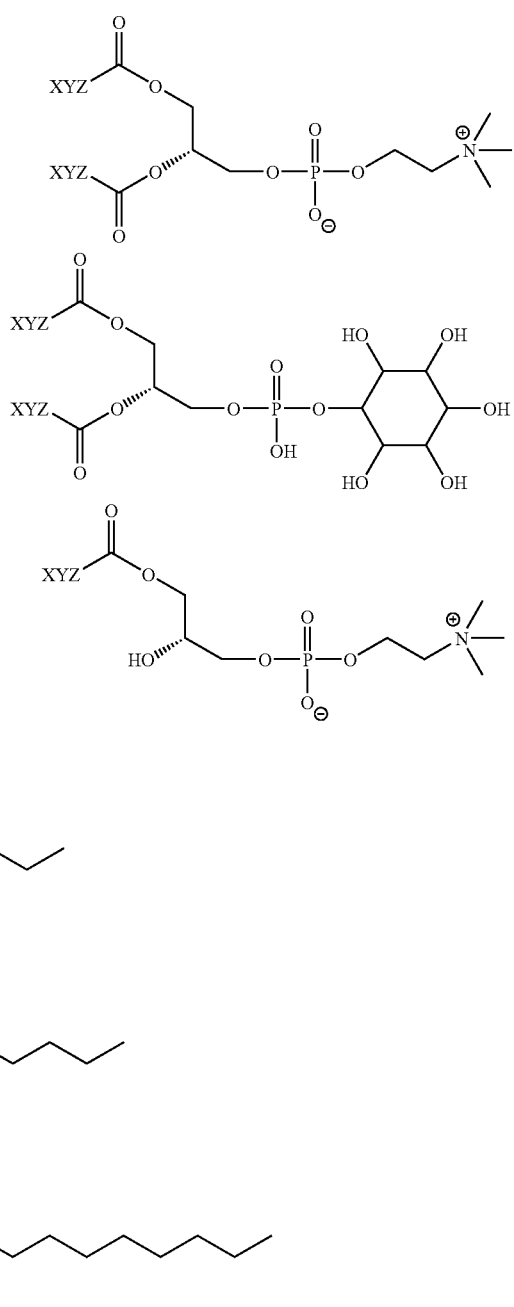
In one aspect the compound is of the formula
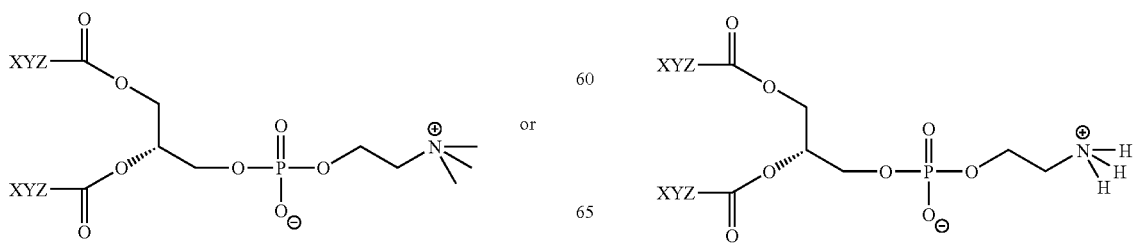

In one aspect the compound is of the formula

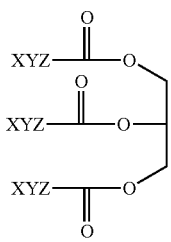

In one aspect the compound is of the formula

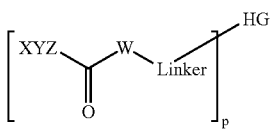

wherein p is 1 to 10, preferably 1 to 5, preferably 1, 2 or 3, and wherein each W, X, Y and Z is selected independently of each other.

In one aspect the compound is of the formula

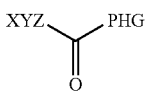

In one aspect the compound is of the formula

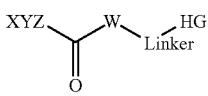

Preferably the compound comprises at least two non-polar moieties wherein each is independently selected from non-polar moieties of the formula X—Y—Z—.

In one preferred aspect the compound is of the formula

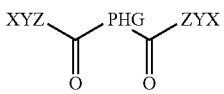

wherein each W, X, Y and Z is selected independently of each other.

In one preferred aspect the compound is of the formula

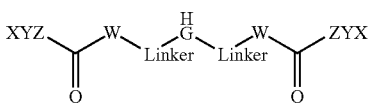

wherein each W, X, Y and Z is selected independently of each other.

In one aspect the compound comprises at least three non-polar moieties wherein each is independently selected from non-polar moieties of the formula X—Y—Z—.

In one preferred aspect the compound is of the formula

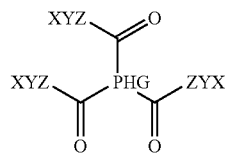

wherein each W, X, Y and Z is selected independently of each other.

In one preferred aspect the compound is of the formula

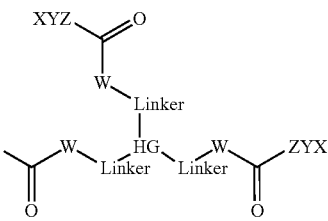

wherein each W, X, Y and Z is selected independently of each other.

Further highly preferred aspects of the present invention are described below. The present invention may provide
a compound of the formula

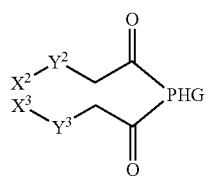

wherein $Y^2$ and $Y^3$ are independently S or Se, and $X^2$ and $X^3$ are independently selected from unsubstituted $C_{10}$-$C_{18}$ alkyl, unsubstituted $C_{10}$-$C_{18}$ alkenyl and unsubstituted $C_{10}$-$C_{18}$ alkynyl.

a compound of the formula

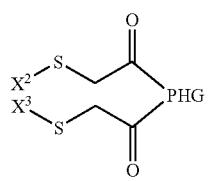

$X^2$ and $X^3$ are independently selected from unsubstituted $C_{10}$-$C_{18}$ alkyl, unsubstituted $C_{10}$-$C_{18}$ alkenyl and unsubstituted $C_{10}$-$C_{18}$ alkynyl.

a compound of the formula

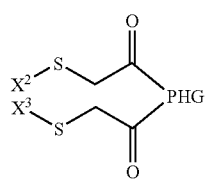

$X^2$ and $X^3$ are independently selected from unsubstituted $C_{14}$ alkyl, unsubstituted $C_{14}$ alkenyl and unsubstituted $C_{14}$ alkynyl.

a compound of the formula

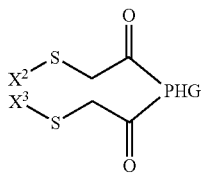

$X^2$ and $X^3$ are independently selected from $CH_3(CH_2)_{13}—$, $CH_3(CH_2)_6CH=CH(CH_2)_5—$, and $CH_3CH_2C\equiv C(CH_2)_{10}—$.

a compound of the formula

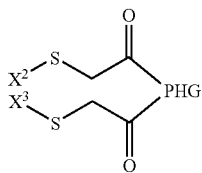

$X^2$ and $X^3$ are both $CH_3(CH_2)_{13}—$.

a compound of the formula

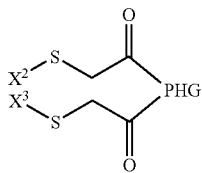

$X^2$ and $X^3$ are both $CH_3(CH_2)_6CH=CH(CH_2)_5—$.

a compound of the formula

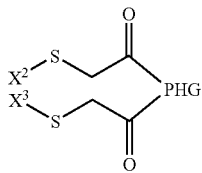

$X^2$ and $X^3$ are both $CH_3CH_2C\equiv C(CH_2)_{10}—$.

a compound of the formula

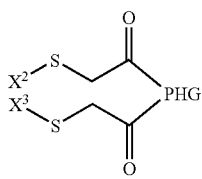

$X^2$ and $X^3$ are both $CH_3(CH_2)_{13}—$, wherein the PHG is derived from the polar head group of a phosphatidylcholine (PC), or a phosphatidylethanolamine (PE).

a compound of the formula

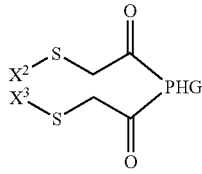

$X^2$ and $X^3$ are both $CH_3(CH_2)_6CH=CH(CH_2)_5—$, wherein PHG is derived from the polar head group of a phosphatidylcholine (PC), or a phosphatidylethanolamine (PE).

a compound of the formula

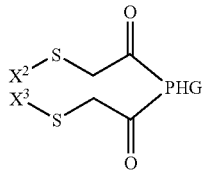

$X^2$ and $X^3$ are both $CH_3CH_2C\equiv C(CH_2)_{10}—$, (wherein PHG is derived from the polar head group of a phosphatidylcholine (PC), or a phosphatidylethanolamine (PE).

a compound of the formula

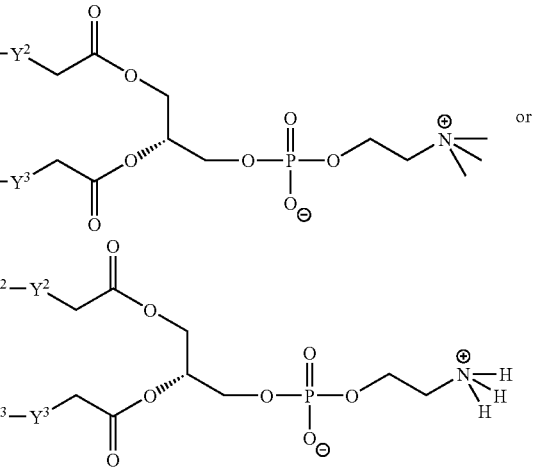

wherein $Y^2$ and $Y^3$ are independently S or Se, and $X^2$ and $X^3$ are independently selected from $C_{10}$-$C_{18}$ alkyl, $C_{10}$-$C_{18}$ alkenyl and $C_{10}$-$C_{18}$ alkynyl.

a compound of the formula

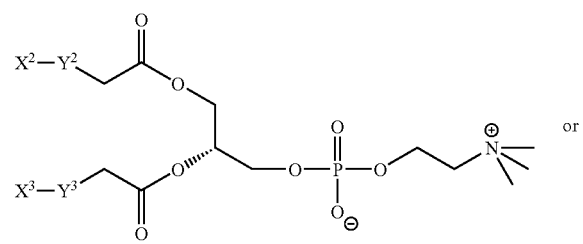

-continued

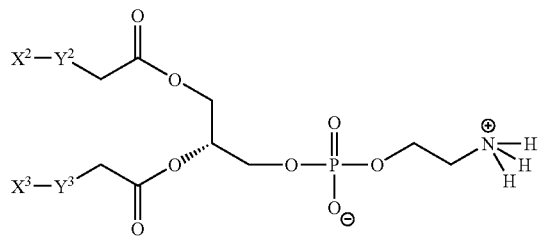

wherein $Y^2$ and $Y^3$ are independently S or Se, and $X^2$ and $X^3$ are independently selected from unsubstituted $C_{10}$-$C_{18}$ alkyl, unsubstituted $C_{10}$-$C_{18}$ alkenyl and unsubstituted $C_{10}$-$C_{18}$ alkynyl.

a compound of the formula

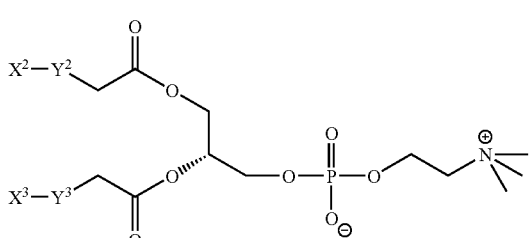

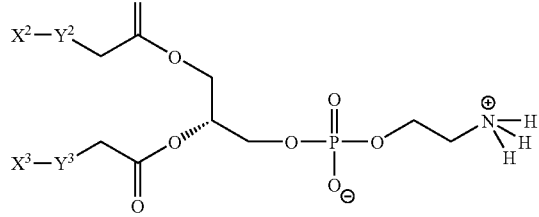

wherein $Y^2$ and $Y^3$ are independently S or Se, and $X^2$ and $X^3$ are independently selected from unsubstituted $C_{14}$ alkyl, unsubstituted $C_{14}$ alkenyl and unsubstituted $C_{14}$ alkynyl.

a compound of the formula

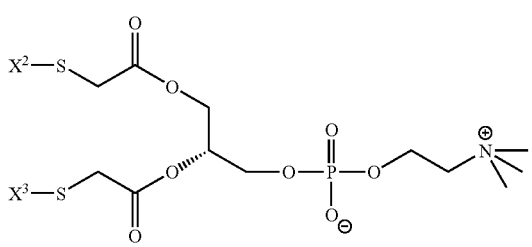

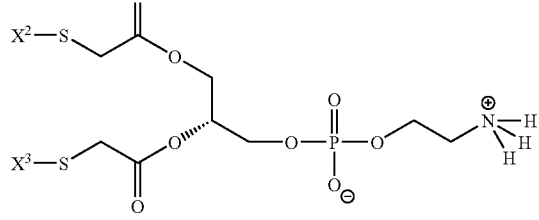

wherein $X^2$ and $X^3$ are independently selected from $C_{10}$-$C_{18}$ alkyl, $C_{10}$-$C_8$ alkenyl and $C_{10}$-$C_{18}$ alkynyl.

a compound of the formula

wherein $X^2$ and $X^3$ are independently selected from unsubstituted $C_{10}$-$C_{18}$ alkyl, unsubstituted $C_{10}$-$C_{18}$ alkenyl and unsubstituted $C_{10}$-$C_{18}$ alkynyl.

a compound of the formula

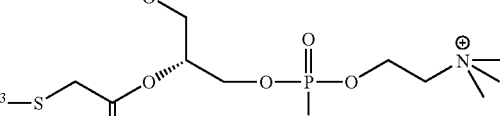

wherein $X^2$ and $X^3$ are independently selected from unsubstituted $C_{14}$ alkyl, unsubstituted $C_{14}$ alkenyl and unsubstituted $C_{14}$ alkynyl.

a compound of the formula

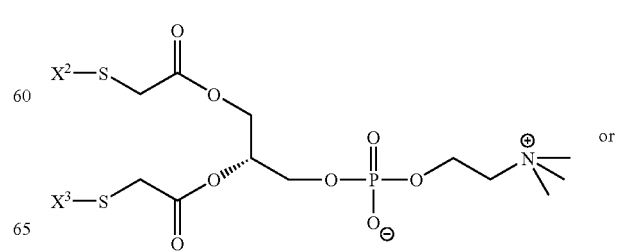

-continued

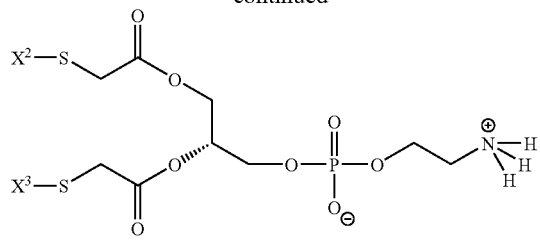

$X^2$ and $X^3$ are both $CH_3(CH_2)_{13}$—
a compound of the formula

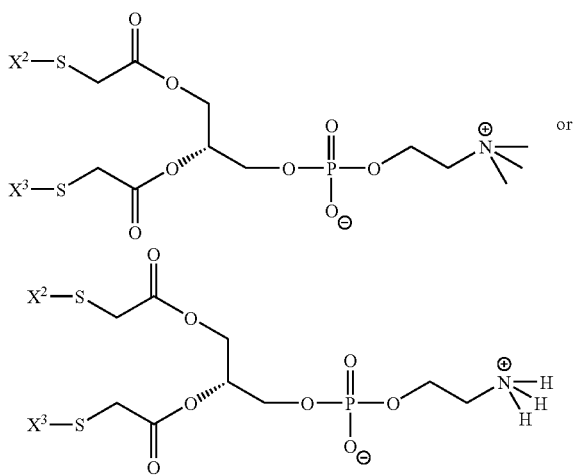

$X^2$ and $X^3$ are both $CH_3(CH_2)_6CH=CH(CH_2)_5$—
a compound of the formula

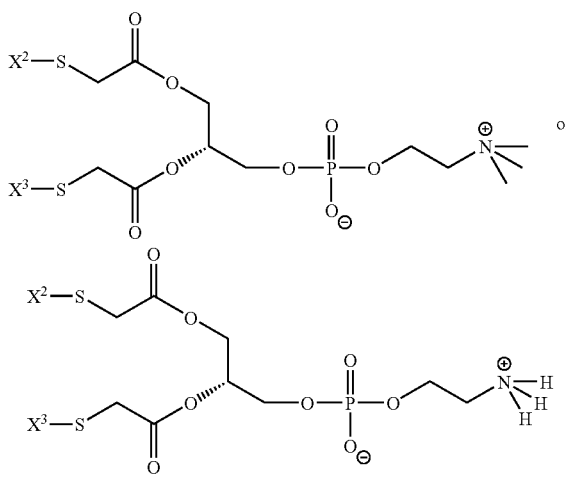

$X^2$ and $X^3$ are both $CH_3CH_2C\equiv C(CH_2)_{10}$—
a compound of the formula

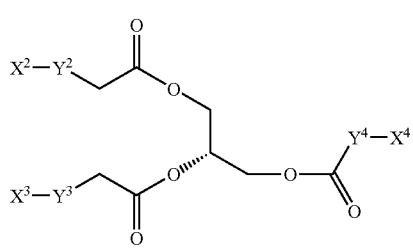

wherein $Y^2$, $Y^3$ and $Y^4$ are independently S or Se, and $X^2$, $X^3$ and $X^4$ are independently selected from $C_{10}$-$C_{18}$ alkyl, $C_{10}$-$C_{18}$ alkenyl and $C_{10}$-$C_{18}$ alkynyl.

a compound of the formula

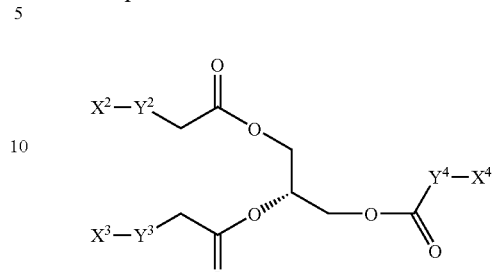

wherein $Y^2$, $Y^3$ and $Y^4$ are independently S or Se, and $X^2$, $X^3$ and $X^4$ are independently selected from unsubstituted $C_{10}$-$C_{18}$ alkyl, unsubstituted $C_{10}$-$C_{18}$ alkenyl and unsubstituted $C_{10}$-$C_{18}$ alkynyl.

a compound of the formula

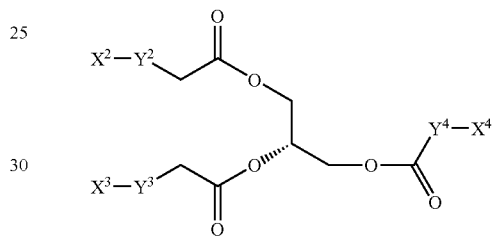

wherein $Y^2$, $Y^3$ and $Y^4$ are independently S or Se, and $X^2$, $X^3$ and $X^4$ are independently selected from unsubstituted $C_{14}$ alkyl, unsubstituted $C_{14}$ alkenyl and unsubstituted $C_{14}$ alkynyl.

a compound of the formula

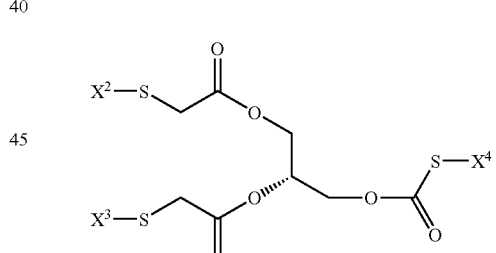

wherein $X^2$, $X^3$ and $X^4$ are independently selected from $C_{10}$-$C_{18}$ alkyl, $C_{10}$-$C_{18}$ alkenyl and $C_{10}$-$C_{18}$ alkynyl.

a compound of the formula

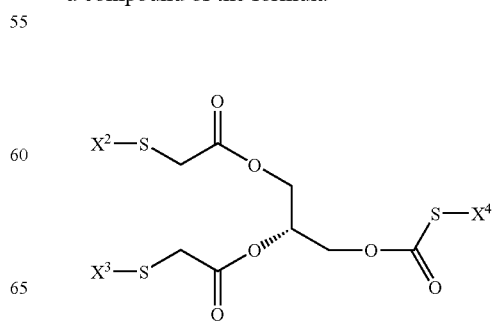

wherein $X^2$, $X^3$ and $X^4$ are independently selected from unsubstituted $C_{10}$-$C_{18}$ alkyl, unsubstituted $C_{10}$-$C_{18}$ alkenyl and unsubstituted $C_{10}$-$C_{18}$ alkynyl.

a compound of the formula

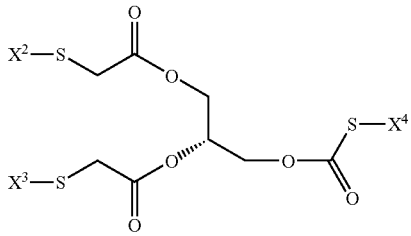

wherein $X^2$ and $X^3$ are independently selected from unsubstituted $C_{14}$ alkyl, unsubstituted $C_{14}$ alkenyl and unsubstituted $C_{14}$ alkynyl.

a compound of the formula

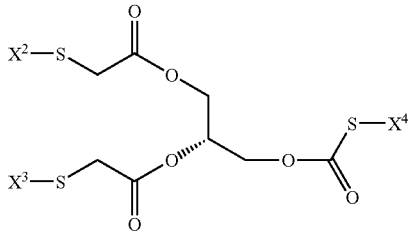

wherein $X^2$, $X^3$ and $X^4$ are each $CH_3(CH_2)_{13}$— a compound of the formula

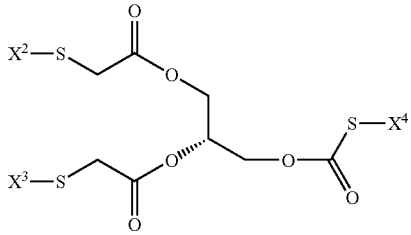

wherein $X^2$, $X^3$ and $X^4$ are each $CH_3(CH_2)_6CH\!=\!CH(CH_2)_5$— a compound of the formula

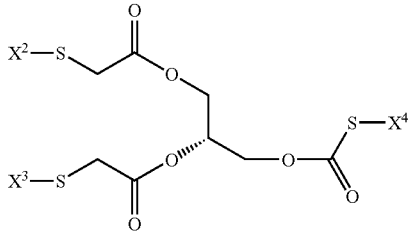

wherein $X^2$, $X^3$ and $X^4$ are each $CH_3CH_2C\!\equiv\!C(CH_2)_{10}$—

Further Aspects

The compounds of the present invention may be combined with a liposome or formulated into micellar form to assist in administration.

In a further aspect the present compound maybe formulated in a cochleate delivery vehicles. Cochleate delivery vehicles represent a new technology platform for oral delivery of drugs. Cochleates are stable phospholipid-cation precipitates composed of simple, naturally occurring materials, for example, phosphatidylserine and calcium. Cochleates are a potential nanosized system that can encapsulate hydrophobic, amphiphilic, negatively or positively charged moieties.

In one aspect the compound of the present invention is an isolated form or purified form. For example, the compound may be in a form or at a purity other than that found in a biological system such as in vivo.

The compounds of the present invention may be formulated to provide a pharmaceutical composition comprising a compound of the invention optionally admixed with a pharmaceutically acceptable carrier, diluent, excipient or adjuvant.

In one further aspect the compound may be a lipid compound comprising at least one non-polar moiety and a polar moiety, wherein the non-polar moiety is of the formula X—Y—Z—, wherein X is a hydrocarbyl chain, Y is selected from at least one of S, Se, $SO_2$, SO, O, $CH_2$, and Z is an optional hydrocarbyl group, wherein when Y is $CH_2$, the chain X—Y-Z contains an even number of atoms; wherein the polar moiety is of the formula —[C(O)]$_m$PHG, wherein PHG is a polar head group, and wherein m is the number of non-polar moieties.

Pharmaceutical Composition

The present invention also provides a pharmaceutical composition comprising a therapeutically effective amount of the agent of the present invention and a pharmaceutically acceptable carrier, diluent or excipients (including combinations thereof).

This is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

This pharmaceutical composition will desirably be provided in a sterile form. It may be provided in unit dosage form and will generally be provided in a sealed container. A plurality of unit dosage forms may be provided.

Pharmaceutical compositions within the scope of the present invention may include one or more of the following: preserving agents, solubilising agents, stabilising agents, wetting agents, emulsifiers, sweeteners, colourants, flavouring agents, odourants, salts compounds of the present invention may themselves be provided in the form of a pharmaceutically acceptable salt), buffers, coating agents, antioxidants, suspending agents, adjuvants, excipients and diluents. Examples of preservatives include sodium benzoate, sorbic acid and esters of p-hydroxybenzoic acid.

They may also contain other therapeutically active agents in addition to compounds of the present invention. Where two or more therapeutic agents are used they may be administered separately (e.g. at different times and/or via different routes)

and therefore do not always need to be present in a single composition. Thus combination therapy is within the scope of the present invention.

Route of Administration

A pharmaceutical composition within the scope of the present invention may be adapted for administration by any appropriate route. For example, it may be administered by the oral (including buccal or sublingual), rectal, nasal, topical (including buccal, sublingual or transdermal), vaginal or parenteral (including subcutaneous, intramuscular, intravenous or intradermal) routes. Such a composition may be prepared by any method known in the art of pharmacy, for example by admixing one or more active ingredients with a suitable carrier.

Different drug delivery systems can be used to administer pharmaceutical compositions of the present invention, depending upon the desired route of administration. Drug delivery systems are described, for example, by Langer (Science 249:1527-1533 (1991)) and by Illum and Davis (Current Opinions in Biotechnology 2: 254-259 (1991)). Different routes of administration for drug delivery will now be considered in greater detail:

The agents of the present invention may be administered alone but will generally be administered as a pharmaceutical composition—e.g. when the agent is in admixture with a suitable pharmaceutical excipient, diluent or carrier selected with regard to the intended route of administration and standard pharmaceutical practice.

For example, the agent can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, via the penis, vaginal, epidural, sublingual.

It is to be understood that not all of the agent need be administered by the same route. Likewise, if the composition comprises more than one active component, then those components may be administered by different routes.

If the agent of the present invention is administered parenterally, then examples of such administration include one or more of: intravenously, intra-arterially, intraperitoneally, intrathecally, intraventricularly, intraurethrally, intrastemally, intracranially, intramuscularly or subcutaneously administering the agent; and/or by using infusion techniques.

(I) Oral Administration

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, maize starch or derivatives thereof, stearic acid or salts thereof. Soft gelatine capsules may comprise vegetable oils, waxes, fats, semi-solid, or liquid polyols etc. Solutions and syrups may comprise water, polyols and sugars. For the preparation of suspensions oils (e.g. vegetable oils) may be used to provide oil-in-water or water-in-oil suspensions. An active agent intended for oral administration may be coated with or admixed with a material that delays disintegration and/or absorption of the active agent in the gastrointestinal tract (e.g. glyceryl monostearate or glyceryl distearate may be used). Thus the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

(II) Transdermal Administration

Pharmaceutical compositions adapted for transdermal administration may be provided as discrete patches intended to remain in intimate contact with the epidermis of the recipient for a prolonged period of time. For example, the active ingredient may be delivered from the patch by iontophoresis. (Iontophoresis is described in *Pharmaceutcal Research*, 3(6): 318 (1986).)

(III) Topical Administration

Alternatively, the agent of the present invention can be administered in the form of a suppository or pessary, or it may be applied topically in the form of a gel, hydrogel, lotion, solution, cream, ointment or dusting powder. The agent of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

(IV) Rectal Administration

Pharmaceutical compositions adapted for rectal administration may be provided as suppositories or enemas.

(V) Nasal Administration

Pharmaceutical compositions adapted for nasal administration may use solid carriers, e.g. powders (preferably having a particle size in the range of 20 to 500 microns). Powders can be administered in the manner in which snuff is taken, i.e. by rapid inhalation through the nose from a container of powder held close to the nose. Compositions adopted for nasal administration may alternatively use liquid carriers, e.g. nasal sprays or nasal drops. These may comprise aqueous or oil solutions of the active ingredient.

Compositions for administration by inhalation may be supplied in specially adapted devices —e.g. in pressurised aerosols, nebulizers or insufflators. These devices can be constructed so as to provide predetermined dosages of the active ingredient (VI) Vaginal Administration Pharmaceutical compositions adapted for vaginal administration may be provided as pessaries, tampons, creams, gels, pastes, foams or spray formulations.

(VII) Parenteral Administration

If the agent of the present invention is administered parenterally, then examples of such administration include one or more of: intravenously, intra-arterially, intraperitoneally, intrathecally, intraventricularly, intraurethrally, intrasternally, intracranially, intramuscularly or subcutaneously administering the agent; and/or by using infusion techniques.

For parenteral administration, the agent is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Transdermal

"Transdermal" refers to the delivery of a compound by passage through the skin and into the blood stream.

Transmucosal

"Transmucosal" refers to delivery of a compound by passage of the compound through the mucosal tissue and into the blood stream.

Transurethral or Intraurethral

"Transurethral" or "intraurethral" refers to delivery of a drug into the urethra, such that the drug contacts and passes through the wall of the urethra and enters into the blood stream.

Penetration Enhancement or Permeation Enhancement

"Penetration enhancement" or "permeation enhancement" refers to an increase in the permeability of the skin or mucosal tissue to a selected pharmacologically active compound such that the rate at which the compound permeates through the skin or mucosal tissue is increased.

Penetration enhancers may include, for example, dimethylsulfoxide (DMSO), dimethyl formamide (DMF), N,N-dimethylacetamide (DMA), decylmethylsulfoxide (CIOMSO), polyethyleneglycol monolaurate (PEGML), glyceral monolaurate, lecithin, 1-substituted azacycloheptanones, particularly 1-N-dodecylcyclazacylcoheptanones (available under the trademark Azone™ from Nelson Research & Development Co., Irvine, Calif.), alcohols and the like.

Carriers or Vehicles

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

Examples of pharmaceutically acceptable carriers include, for example, water, salt solutions, alcohol, silicone, waxes, petroleum jelly, vegetable oils, polyethylene glycols, propylene glycol, sugars, gelatin, lactose, amylose, magnesium stearate, talc, surfactants, silicic acid, viscous paraffin, perfume oil, fatty acid monoglycerides and diglycerides, petroethral fatty add esters, hydroxymethyl-cellulose, polyvinylpyrrolidone, and the like.

Epidermal Drug Delivery (Transfersomes)

Transfersomes ("carrying bodies") are complex, most often vesicular, bi- or multi-component aggregates capable of crossing barriers and of transferring material between the application and the destination sites. Transfersomes are sold by IDEA Corporation, Munich, Germany, and TRANSFERSOME is a trade mark of that company. Transfersome transdermal drug delivery technology may be used for controllable and non-invasive delivery of a wide variety of large molecules as well as for the improved delivery of small molecules, including the metabolic enzyme antagonists and/or drugs of the present invention.

Transfersomes may be optimised to attain extremely flexible and self-regulating membranes. They are therefore deformable and consequently can cross microporous barriers efficiently, even when the available passages are much smaller than the average aggregate size. Transfersome formulations are typically composed of natural amphipatic compounds suspended in a water-based solution, optionally containing biocompatible surfactants. Vesicular Transfersomes consist of a lipid bilayer surrounding an aqueous core and further contain at least one component, capable of softening the membrane. The bilayer of a Transferosome is therefore more flexible than a liposome membrane, even metastable. Transfersome vesicles consequently change their shape easily by adjusting locally to ambient stress.

Skin is one of the best biological barriers. Its outermost part, the horny layer, reaches less than 10% into the depth of the skin but contributes over 80% to the skin permeability barrier. This body protecting layer consists of overlapping, flaccid corneocytes, organized in columnar clusters, sealed with multilamellar lipid sheets that are covalently attached to the cell membranes and very tightly packed. Generally, the average number of and the degree of order in the intercellular lipid lamellae increases toward the skin surface. This is accompanied by a continuous, but nonlinear, decrease in local water content near the surface. Notwithstanding this, the peak skin barrier is located in the inner half of the horny layer, where the intercellular lipid seals are already formed, but not yet compromised by the skin cells detachment.

Passage of fransfersome aggregates across the skin is a function of vesicle membrane flexibility, hydrophilicity, and the ability to retain vesicle integrity, while the aggregate undergoes a significant change in shape. When a suspension of Transfersome vesicles is placed on the surface of the skin, water evaporates from the relatively arid skin surface and the vesicles start to dry out. Due to the strong polarity of major Transfersome ingredients, the large number of hydrophilic groups on the membrane, assisted by the softness of the membrane, the vesicles are attracted to the areas of higher water content in the narrow gaps between adjoining cells in the skin barrier, enabling skin penetration of the vehicle. This, together with the vesicle's extreme ability to deform, enables Transfersome aggregates to open, temporarily, the tiny "cracks" through which water normally evaporates out of the skin. Channels between the skin cells, two orders of magnitude wider than the original micropores, are thus created. Such newly activated passages can accommodate sufficiently deformable vesicles, which maintain their integrity but change their shape to fit the channel. Along the resulting "virtual pathways", or "virtual channels" in the horny layer, Transfersomes reach regions of high water content in the deeper skin layers. There, the vesicles (re)distribute. Since Transfersomes are too large to enter the blood vessels locally, they bypass the capillary bed and get to subcutaneous tissue, where they accumulate.

Although small molecules that have crossed the horny layer of the skin (stratum corneum) are normally cleared from the skin through the blood circulation, delivery of drugs by means of Transfersome vesicles allows accumulation of drug deep under the skin. Due to their large size, the vesicles are cleared slowly from the skin and associated drugs can accumulate at the site. Transfersome mediated administration of weight drugs, consequently, tends to shift the drug distribution towards the deep tissue under the application site.

Blood Brain Barrier (BBB)

Pharmaceutical compositions may be designed to pass across the blood brain barrier (BBB). For example, a carrier such as a fatty acid, inositol or cholesterol may be selected that is able to penetrate the BBB. The carrier may be a substance that enters the brain through a specific transport system in brain endothelial cells, such as insulin-like growth factor I or II. The carrier may be coupled to the active agent or may contain/be in admixture with the active agent. Liposomes can be used to cross the BBB. WO91/04014 describes a liposome delivery system in which an active agent can be encapsulated/embedded and in which molecules that are normally transported across the BBB (e.g. insulin or insulin-like growth factor I or II) are present on the liposome outer surface. Liposome delivery systems are also discussed in U.S. Pat. No. 4,704,355.

Polymer Delivery/Therapeutics

The agents may further be delivered attached to polymers. Polymer based therapeutics have been proposed to be effective delivery systems, and generally comprise one or more agents to be delivered attached to a polymeric molecule, which acts as a carrier. The agents are thus disposed on the polymer backbone, and are carried into the target cell together with the polymer.

The agents may be coupled, fused, mixed, combined, or otherwise joined to a polymer. The coupling, etc between the agent and the polymer may be permanent or transient, and may involve covalent or non-covalent interactions (including ionic interactions, hydrophobic forces, Van der Waals interactions, etc). The exact mode of coupling is not important, so long as the agent is taken into a target cell substantially together with the polymer. For simplicity, the entity comprising the agent attached to the polymer carrier is referred to here as a "polymer-agent conjugate".

Any suitable polymer, for example, a natural or synthetic polymer, may be used, preferably the carrier polymer is a synthetic polymer such as PEG. More preferably, the carrier polymer is a biologically inert molecule. Particular examples of polymers include polyethylene glycol (PEG), N-(2-hydroxypropyl) methacrylamide (HPMA) copolymers, polyamidoamine (PAMAM) dendrimers, HEMA, linear polyamidoamine polymers etc. Any suitable linker for attaching the agent to the polymer may be used. Preferably, the linker is a biodegradable linker. Use of biodegradable linkers enables controlled release of the agent on exposure to the extracellular or intracellular environment. High molecular weight macromolecules are unable to diffuse passively into cells, and are instead engulfed as membrane-encircled vesicles. Once inside the vesicle, intracellular enzymes may act on the polymer-agent conjugate to effect release of the agent. Controlled intracellular release circumvents the toxic side effects associated with many drugs.

Furthermore, agents may be conjugated, attached etc by methods known in the art to any suitable polymer, and delivered. The agents may in particular comprise any of the molecules referred to as "second agents", such as polypeptides, nucleic acids, macromolecules, etc, as described in the section below. In particular, the agent may comprise a pro-drug as described elsewhere.

The ability to choose the starting polymer enables the engineering of polymer-agent conjugates for desirable properties. The molecular weight of the polymer (and thus the polymer-agent conjugate), as well as its charge and hydrophobicity properties, may be precisely tailored. Advantages of using polymer-agent conjugates include economy of manufacture, stability (longer shelf life) and reduction of immunogencity and side effects. Furthermore, polymer-agent conjugates are especially useful for the targeting of tumour cells because of the enhanced permeability and retention (EPR) effect, in which growing tumours are more 'leaky' to circulating macromolecules and large particules, allowing them easy access to the interior of the tumour. Increased accumulation and low toxicity (typically 10-20% of the toxicity of the free agent) are also observed. Use of hyperbranched dendrimers, for example, PAMAM dendrimers, is particularly advantageous in that they enable monodisperse compositions to be made and also flexibility of attachment sites (within the interior or the exterior of the dendrimer). The pH responsiveness of polymer-agent conjugates, for example, those conjugated to polyamindoamine polymers, may be tailored for particular intracellular environments. This enables the drug to be released only when the polymer therapeutic encounters a particular pH or range of pH, i.e., within a particular intracellular compartment. The polymer agent conjugates may further comprise a targeting means, such as an immunoglobulin or antibody, which directs the polymer-agent conjugate to certain tissues, organs or cells comprising a target, for example, a particular antigen. Other targeting means are described elsewhere in this document, and are also known in the art.

Particular examples of polymer-agent conjugates include "Smancs", comprising a conjugate of styrene-co-maleic anhydride and the antitumour protein neocarzinostatin, and a conjugate of PEG (poly-ethylene glycol) with L-asparaginase for treatment of leukaemia; PK1 (a conjugate of a HPMA copolymer with the anticancer drug doxorubicin); PK2 (similar to PK1, but furthermore including a galactose group for targeting primary and secondary liver cancer); a conjugate of HPMA copolymer with the anticancer agent captothecin; a conjugate of HPMA copolymer with the anticancer agent paclitaxel; HPMA copolymer-platinate, etc. Any of these polymer-agent conjugates are suitable for co-loading into the transgenic cells of the present invention.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The agent and/or the pharmaceutical composition of the present invention may be administered in accordance with a regimen of from 1 to 10 times per day, such as once or twice per day.

For oral and parenteral administration to human patients, the daily dosage level of the agent may be in single or divided doses.

Depending upon the need, the agent may be administered at a dose of from 0.01 to 30 mg/kg body weight, such as from 0.1 to 10 mg/kg, more preferably from 0.1 to 1 mg/kg body weight. Naturally, the dosages mentioned herein are exemplary of the average case. There can, of course, be individual instances where higher or lower dosage ranges are merited.

Therapeutically Effective Amount

"Therapeutically effective amount" refers to the amount of the therapeutic agent which is effective to achieve its intended purpose. While individual patient needs may vary, determination of optimal ranges for effective amounts of each nitric oxide adduct is within the skill of the art. Generally the dosage regimen for treating a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination and can be adjusted by one skilled in the art. Thus, the dosage regimen actually employed may vary widely and therefore may deviate from the preferred dosage regimen set forth herein.

Individual

As used herein, the term "individual" refers to vertebrates, particularly members of the mammalian species. The term includes but is not limited to domestic animals, sports animals, primates and humans.

Pharmaceutical Combinations

In general, the agent may be used in combination with one or more other pharmaceutically active agents. The other agent is sometimes referred to as being an auxiliary agent.

Patient

"Patient" refers to animals, preferably mammals, more preferably humans.

Pharmaceutically Acceptable Salt

The agent may be in the form of—and/or may be administered as—a pharmaceutically acceptable salt—such as an acid addition salt or a base salt—or a solvate thereof, including a hydrate thereof. For a review on suitable salts see Berge et al, J. Pharm. Sci., 1977, 66, 1-19.

Typically, a pharmaceutically acceptable salt may be readily prepared by using a desired acid or base, as appropriate. The salt may precipitate from solution and be collected by filtration or may be recovered by evaporation of the solvent.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

Disease States

In one aspect the present invention provides use of a compound of the invention in the manufacture of a medicament for the treatment and/or prevention of a condition selected from syndrome X, obesity, hypertension, fatty liver, diabetes, hyperglycaemia, hyperinsulinemia and stenosis.

In one aspect the present invention provides use of a compound of the invention in the manufacture of a medicament for lowering concentration of cholesterol and triglycerides in the blood of mammals and/or inhibiting the oxidative modification of low density lipoprotein.

In one aspect the present invention provides a method for producing weigh loss or a reduction of the fat mass in a human or non-human animal in need thereof, comprising administering thereto an effective amount of a compound of the invention or a pharmaceutically acceptable salt thereof.

In one aspect the present invention provides a method for the modification of the fat distribution and content of animals in order to improve the quality of the meat, or product such as milk and eggs, comprising administering thereto an effective amount of a compound of the invention or a pharmaceutically acceptable salt thereof. Preferably said animal is an agricultural animal, such as gallinaceous birds, bovine, ovine, caprine or porcine mammals. The animal may be a fish or shellfish, such as salmon, cod, Tilapia, clams, oysters, lobster or crabs.

In one aspect the present invention provides use of a compound of the invention or a pharmaceutically acceptable salt thereof in the manufacture of a medicament for the inhibition and/or prevention of the growth of tumours.

Preferably the present invention provides use of a compound of the invention in the manufacture of a medicament for the inhibition and/or prevention of the invasion of a primary tumour into the connective tissue.

Preferably the present invention provides use of a compound of the invention in the manufacture of a medicament for the inhibition and/or prevention of the metastatic properties of a tumour, i.e. to inhibit the formation of secondary tumours.

The use of the present compounds may increase the overall survival of mammals with tumours.

In one aspect the present invention provides a method for the treatment and/or inhibition of primary and secondary metastatic neoplasms, comprising administering a compound of the invention or a pharmaceutically acceptable salt thereof.

In one aspect the present invention provides use of a compound of the invention or a pharmaceutically acceptable salt thereof in the manufacture of a medicament for the prevention and/or treatment of proliferative skin disorders.

Preferably the present invention provides use of a compound of the invention in the manufacture of a medicament for the prevention and/or treatment of proliferative skin disorders, wherein the skin proliferation disease is selected from the group comprising psoriasis, atopic dermatitis, non-specific dermatitis, primary irritant contact dermatitis, allergic contact dermatitis, lamellar ichthyosis, epidermolytic hyperkeratosis, pre malignant sun induced keratosis, and seborrheic. More preferably the skin proliferation disease is psoriasis.

In one aspect the present invention provides use of a compound of the invention or a pharmaceutically acceptable salt thereof in the manufacture of a medicament for the inhibition of proliferation and/or induction of differentiation of keratinocytes.

In one aspect the present invention provides use of a compound of the invention or a pharmaceutically acceptable salt thereof in the manufacture of a medicament for the prevention and/or treatment of inflammatory disorders Preferably the present invention provides use of a compound of the invention or a pharmaceutically acceptable salt thereof in the manufacture of a medicament for the prevention and/or treatment of inflammatory disorders, wherein the inflammatory disorder is selected from the group comprising immune mediated disorders such as rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myastenia gravis), various cardiovascular disorders (e.g. myocarditis, congestive heart failure, arteriosclerosis and stable and unstable angina, and Wegener's granulomatosis), inflammatory bowel diseases and Chron's colitis, nephritis, various inflammatory skin disorders (e.g. psoriasis, atopic dermatitis and food allergy) and acute and chronic allograft rejection after organ transplantation.

In one aspect the present invention provides a method for enhancing the endogenous production of interleukin-10 (IL-10) in mammalian cells or tissues, comprising administering a compound of the invention or a pharmaceutically acceptable salt thereof. Preferably the mammal has developed or is susceptible to develop an autoimmune and/or inflammatory disorder.

In one aspect the present invention provides a method for suppression of the endogenous production of interleukin-2 (IL-2) in mammalian cells or tissues, comprising administering a compound of the invention or a pharmaceutically acceptable salt thereof. Preferably the mammal has developed or is susceptible to develop an autoimmune and/or inflammatory disorder.

In one aspect the present invention provides use of a compound of the invention or a pharmaceutically acceptable salt thereof in the manufacture of a medicament for the inhibition of proliferation of stimulated peripheral mononuclear cells (PBMC).

Further description of these and other diseases is provided below.

Obesity, and Related Diseases

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, Acanthosis nigricans, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease.

The present invention therefore aims to provide a treatment regimen that is useful in returning the body weight of obese subjects toward a normal, ideal body weight.

The present invention therefore aims to provide a therapy for obesity that results in maintenance of the lowered body weight for an extended period of time. Further, The present invention therefore aims to reduce or inhibit the weight gain normally induced by fat rich diets.

The present invention therefore aims to prevent obesity and, once treatment has begun, to arrest progression or prevent the onset of diseases that are the consequence of, or secondary to, the obesity, such as hypertension and fatty liver.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity.

The present invention therefore aims to provide a treatment regimen that is useful in lowering the blood pressure.

Further, The present invention therefore aims to provide a treatment regimen that is useful in lowering the concentration of triacylglycerols in the liver. It is anticipated that such a regimen will provide an inhibiting effect on the development of a fatty liver condition, and also be suited as a method for the treatment of the manifested disease.

The compounds of the present invention activate the oxidation, and also reduce the concentration of triglycerides in the liver.

The term "metabolic syndrome" is used to describe a multimetabolic syndrome which is inter alia characterised by hyperinsulinemia, insulin resistance, obesity, glucose intolerance, Type 2 diabetes mellitus, dyslipidemia or hypertension.

As indicated above it is anticipated that the compounds of the present invention will provide a positive effect on all the conditions mentioned above, i.e. by regulating both the glucose and lipid homeostasis, and thus it is anticipated that the compounds of the present invention will be suitable agents for the regulation of the above defined metabolic disease (sometimes called syndrome X).

Diabetes

There are two major forms of diabetes mellitus. One is type I diabetes, which is also known as insulin-dependent diabetes mellitus (IDDM), and the other is type II diabetes, which is also known as noninsulin-dependent diabetes mellitus (NIDDM). Most patients with IDDM have a common pathological picture; the nearly total disappearance of insulin-producing pancreatic beta cells which results in hyperglycemia.

Considerable evidence has been accumulated showing that most IDDM is the consequence of progressive beta-cell destruction during an asymptomatic period often extending over many years. The prediabetic period can be recognised by the detection of circulating islet-cell autoantibodies and insulin autoantibodies.

There is a need for a compound which would be nontoxic and have no side effects but which would prevent clinical IDDM and NIDDM.

Type I diabetes: severe diabetes mellitus, usually of abrupt onset prior to maturity, characterised by low plasma insulin levels, polydipsia, polyuria, increased appetite, weight loss and episodic ketoacidosis; also referred to as IDDM.

Type II diabetes: an often mild form of diabetes mellitus, often of gradual onset, usually in adults, characterised by normal to high absolute plasma insulin levels which are relatively low in relation to plasma glucose levels; also referred to as NIDDM.

Type I and II diabetes are in accordance with an etiologic classification considered as primary diabetes respectively.

Secondary diabetes comprises pancreatic, extrapancreatic/endocrine or drug-induced diabetes. Further, some types of diabetes are classified as exceptional forms. These include lipoatrophic, myatonic diabetes, and a type of diabetes caused by disturbance of insulin receptors.

Considering the high prevalence of diabetes in our society and the serious consequences associated therewith as discussed above, any therapeutic drug potentially useful for the treatment and prevention of this disease could have a profound beneficial effect on their health. There is a need in the art for a drug that will reduce the concentration of glucose in the blood of diabetic subjects without significant adverse side effects.

The present invention therefore aims to provide a treatment regimen that is useful in lowering the blood glucose and to treat a diabetic condition.

The present invention therefore aims to provide a treatment regimen that is useful in lowering the concentration of insulin in the blood, and to increase the effect of the remaining insulin.

Stenosis

Many pathological conditions have been found to be associated with smooth muscle cell proliferation. Such conditions include restenosis, arteriosclerosis, coronary heart disease, thrombosis, myocardial infarction, stroke, smooth muscle neoplasms such as leiomyoma and leiomyosarcoma of the bowel and uterus and uterine fibroid or fibroma.

Over half a million interventional intravascular procedures are performed each year. While such invasive procedures continue to improve over time, as many as 30-50% of the procedures performed each year fail as a result of restenosis, i.e. the formation of secondary stenosis. The reduction of restenosis is, therefore, often cited as the most critical factor in increasing the success realised in the treatment of cardiovascular disease through the use of interventional intravascular procedures, such as angioplasty, atherectomy, and procedures utilising stents and laser technology.

In balloon angioplasty, e.g. Percutaneous Transluminal Coronary Angioplasty (PTCA), a small incision is made to an artery in the patient's leg or arm and a long hollow tube, called a guide catheter, is inserted into the artery. A thick guide wire and deflated balloon catheter are then inserted into the guide catheter and are carefully advanced through the patient's blood vessels using x-ray visualization. The deflated balloon is advanced until it reaches the site of the luminal narrowing, at which point the physician inflates the balloon one or more times to a pressure of about 4-6 atm for about 60 sec. When inflated, the balloon cracks and fractures the plaque and stretches the muscle fibre in the artery wall beyond its ability to recoil completely. Although no plaque is removed in this procedure, the fracturing of the plaque and the stretching of the arterial wall increase the vessel lumen, thereby allowing for increased blood flow.

The restenosis that accompanies such procedures is characterised by platelet aggregation and adhesion, smooth muscle cell proliferation, narrowing of the vessel lumen, restricted vasodilatation, and an increase in blood pressure. Smooth muscle cells in the intimal layer of the artery have been reported to enter the growth cycle within about 2-3 days of these procedures and to proliferate for several days thereafter (intimal hyperplasia).

Compounds that reportedly suppress smooth muscle profile ration in vitro may have undesirable pharmacological side effects when used in vivo. Heparin is an example of one such compound, which reportedly inhibits smooth muscle cell proliferation in vitro but when used in vivo has the potential adverse side effect of inhibiting coagulation.

As is apparent from the foregoing, many problems remain to be solved in the use of inhibitory drugs to effectively treat smooth muscle cell mobilisation and proliferation. It would be highly advantageous to develop new compositions or methods for inhibiting stenosis, restenosis or related disorders due to proliferation and mobilisation of vascular smooth muscle cells following, for example, traumatic injury to vessels rendered during vascular surgery.

It is anticipated that the compounds in accordance with the present invention will be effectively it the treatment of these diseases.

Tumours

As discussed in WO 02/03983 the development of new and more effective chemotherapeutic agents for cancer treatment requires consideration of a variety of factors including cytotoxicity, tumour cell proliferation, invasion and metastasis. Conventional anticancer agents have typically been identified on the basis of their cytotoxicity alone.

Tumour progression is thought to occur when variant cells having selective growth properties arise within a tumour cell population, and one of the final stages of tumour progression is the appearance of the metastatic phenotype.

During metastasis, the tumour cells invade the blood vessels, survive against circulating host immune defences, and then extravasate, implant, and grow at sites distant from the primary tumour. This ability of tumour cells to invade neighbouring tissues and to colonise other organs is among the leading causes of cancer related deaths.

The term metastasis encompasses a number of phenotypic traits which together result in the clinical problem that most often leads to death from cancer. The cells lose their adherence and restrained position within an organised tissue, move into adjacent sites, develop the capacity both to invade and to egress from blood vessels, and become capable of proliferating in unnatural locations or environments. These changes in growth patterns are accompanied by an accumulation of biochemical alterations which have the capacity to promote the metastatic process.

So far, little is known about the intrinsic mechanism involved in the metastatic cascade. It is likely that in some cases the augmented metastatic potential of certain tumour cells may be due to an increased expression of oncogenes, which normally are responsible for control of various cellular functions, including differentiation, proliferation, cell motility, and communication. Further, it has been shown that substances that modulate signal transduction pathways can inhibit the metastatic behaviour of a tumour, and it is also speculated that compounds with surface related effects, e.g. compounds which modulates the cell membranes, might be involved in the process leading to metastasis.

Cancer is a disease of inappropriate tissue accumulation. This derangement is most evident clinically when tumour tissue bulk compromises the function of vital organs.

Contrary to what is generally thought, human malignant disorders are usually not diseases of rapid cell proliferation. In fact, the cells of most common cancers proliferate more slowly than many cells in normal tissues.

It is a relatively slow accumulation of tumour tissue within vital organs that proves fatal to most patients who die of cancer.

Chemotherapeutic agents share one characteristic: they are usually more effective in killing or damaging malignant cells than normal cells. However, the fact that they do harm normal cells indicates their potential for toxicity.

Nearly all chemotherapeutic agents currently in use interfere with DNA synthesis, with the provision of precursors for DNA and RNA synthesis, or with mitosis. Such drugs are most effective against cycling cells. The mechanism of cell death after treatment with any single agent or combination of agents is complex and is likely to include more than one process. Because most clinically detectable tumours are composed mostly of non-cycling cells, it is not surprising that chemotherapy is not always effective in eradicating cancer.

The strategy of cancer treatment is to shift tumour cells from a non-cycling compartment to a cycling compartment.

Several methods that promote this shift form the basis for combined-modality treatment Surgery is most commonly used to reduce tumour size and thus facilitate re-entry of cancer cells into the cell cycle. After the primary tumour is completely removed, microscopic metastases may remain at distant sites. Because of their small size, the micrometastases are composed principally of cycling cells.

Small numbers of cells that remain at primary tumour site are also likely to re-enter the cell cycle. Thus, the remaining cancer cells are often susceptible to chemotherapy. Radiation therapy or chemotherapy alone can also be used to reduce tumour bulk and thus recruit cells into the cycling cell compartment.

Combination drug therapy is, therefore, the basis for most chemotherapy employed at present. Combination chemotherapy uses the different mechanisms of action and cytotoxic potentials of multiple drugs.

However, even though the chemotherapeutic agents are more effective in killing or damaging malignant cells than normal cells, the fact that they do harm normal cells indicates their great potential for toxicity. For chemotherapy to be effective, the patient must be in good physiologic condition.

Cancer treatment requires inhibition of a variety of factors including tumour cell proliferation, metastatic dissemination of cancer cells to other parts of the body, invasion, tumour-induced neovascularization, and enhancement of host immunological responses and cytotoxicity.

Conventional cancer chemotherapeutic agents have often been selected on the basis of their cytotoxicity to tumour cells. However, some anticancer agents have adverse effects on the patient's immunological system. Unfortunately, for the vast majority of conventional antineoplastic agents the margin between an effective dose and a toxic dose, i.e., the therapeutic index, is extremely low. Thus, it would be greatly advantageous if a cancer therapy or treatment could be developed that would afford noncytotoxic protection against factors that might lead to growth, progression and metastasis of invasive cancers.

The present invention is directed to a method for the prevention and/or treatment of primary and metastatic neoplasms that involves using a fatty acid analogues of the present invention to treat a patient suffering from a cancer.

The two essential features of cancer are invasion and metastasis. At one extreme, microinvasion of the basement membrane characterises the transition from neoplasia to cancer, and at the other extreme, metastases generally lead to death.

Invasion into the underlying connective tissue by primary tumour proceeds in stages and is facilitated by various mediators produced by the tumour cells. Tumour cells that have not invaded the basement membrane and remain confined within the epithelium are termed carcinoma in situ.

Metastases, on the other hand, may form when circulating tumour cells with adherent lymphocytes and platelets are trapped in capillaries and the tumour cell membrane interacts with the capillary endothelium. The capillary endothelial junctions retract, and tumour cell ligands bind to receptors on the endothelial and basement membranes.

Tumour cells then release collagenase IV, which destroys collagen IV, a major component of the underlying basement membrane. Invasion of the subcapillary connective tissue is aided by binding to the glycoproteins laminin and fibronectin, by the release of proteases that destroy the matrix, and by the secretion of motility and chemotactic factors. Tumour cells then may proliferate and synthesise platelet aggregatory factors such as thromboxanes and procoagulants, thereby leading to the deposition of a fibrin cocoon around the cells. Such a cocoon may protect the micrometastasis from attack by the host's immune system.

Cancers that can be prevented and/or treated by the compositions and methods of the present invention include, but are not limited to, human sarcomas and carcinomas, e.g. carcinomas, e.g., colon carcinoma, pancreatic cancer, breast cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumour, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Specific examples of such cancers are described in the sections below.

Skin Disorders

As discussed in WO 02/26218 proliferative skin diseases are widespread throughout the world and afflict millions of humans and their domesticated animals. Proliferative skin diseases are characterized by keratinocyte cell proliferation, or division, and may also be associated with incomplete epidermal differentiation.

Psoriasis is the most serious of the proliferative skin diseases with which this invention is concerned.

Psoriasis is a genetically determined disease of the skin characterized by two biological hallmarks. First, there is a profound epidermal hyperproliferation related to accelerated and incomplete differentiation. Second, there is a marked inflammation of both epidermis and dermis with an increased recruitment of T lymphocytes, and in some cases, formation of neutrophil microabcesses. Many pathologic features of psoriasis can be attributed to alterations in the growth and maturation of epidermal keratinocytes, with increased proliferation of epidermal cells, occurring within 0.2 mm of the skin's surface.

Traditional investigations into the pathogenesis of psoriasis have focused on the increased proliferation and hyperplasia of the epidermis. In normal skin, the time for a cell to move from the basal layer through the granular layer is 4 to 5 weeks. In psoriatic lesions, the time is decreased sevenfold to tenfold because of a shortened cell cycle time, an increase in the absolute number of cells capable of proliferating, and an increased proportion of cells that are actually dividing. The hyperproliferative phenomenon is also expressed, although to a substantially smaller degree, in the clinically uninvolved skin of psoriatic patients.

A common form of psoriasis, psoriasis vulgaris, is characterized by well-demarcated erythematous plaques covered by thick, silvery scales. A characteristic finding is the isomorphic response (Koebner phenomenon), in which new psoriatic lesions arise at sites of cutaneous trauma.

Lesions are often localized to the extensor surfaces of the extremities, and the nails and scalp are also commonly involved.

Therapeutic efforts in psoriasis are aimed at decreasing the proliferative rate of the epidermis, either by direct action on cell division or indirectly by reducing the immunological response. For patients with localized, limited psoriasis, administration of topical corticosteroids is the most convenient outpatient therapy.

Rapid improvement may be seen with this approach, but the beneficial short-term efficacy is limited and chronic topical corticosteroid treatment is not advisable. Side effects from chronic topical corticosteroid therapy can include atrophy of the skin, development of tolerance to the agent used (tachyphylaxis), and serious exacerbation of the disease after discontinuation. Pituitary-adrenal suppression is a potential and serious complication of potent topical corticosteroid therapy, particularly when the agent covers a large portion of the body surface and is used under occlusive dressings.

The retinoids, particularly etretinate, either alone or in combination with PUVA, are also an effective treatment for psoriasis. Etretinate is especially useful in the exfoliative and pustular varieties of psoriasis. However, several major potential complications must be monitored in patients placed on retinoids. As a class, the retinoids are potent teratogens and should not be given to women of childbearing age who are not using adequate contraception.

Etretinate, like other retinoids, can produce elevations in cholesterol and triglyceride levels; therefore dietary regulation may be necessary. In addition, because etretinate can induce hepatotoxicity, liver function tests should be performed before and at regular intervals during use of the drug.

Considering the complications and side effects attendant to the use of different drugs and photochemotherapy currently used in treating a skin proliferative disease such as psoriasis, there is a need for a new method and a new composition to inhibit keratinocyte proliferation to alleviate the symptoms of skin proliferation diseases.

Inflammatory and Auto-Immune Disoders

As discussed in WO 02/43728, interleukins, interferons, colony stimulating factors and TNFa are examples of a group of diverse multi-functional proteins called cytokines. Cytokines are a class of secreted soluble proteins normally present in very low concentration in a variety of cells; Lymphoid, inflammatory hemopoietic and other cells such as connective tissue cells (e.g. fibroblasts, osteoblasts) secrete a variety of cytokines which regulate the immune, inflammatory, repair and acute phase responses by controlling cell proliferation, differentiation and effector functions. The effects of cytokines are mediated through binding to high affinity receptors on specific cell types.

An important cytokine is IL-10, a 35-40 kDa peptide produced by helper T-cells, B-cells, monocytes, macrophages and other cell types. In vitro, IL-10 has demonstrated immunosuppressive properties as evidenced by its ability to suppress cytokine production including IL-1 and TNFa.

IL-10 also inhibits activation of other inflammatory cytokines, and therefore has potent anti-inflammatory activity.

It has been of recent interest to administer-IL-10 in the treatment of certain conditions characterized by excessive IL-1 and TNFa production. Such diseases or conditions include loosening of prosthetic joint implants, inflammation, diabetes, cancer, graft versus host diseases, viral, fungal and bacterial infections, lipopolysaccharide endotoxin shock, diseases of depressed bone marrow function, thrombocytopenia, osteoporosis, spondyloarthropathies, Paget's disease, inflammatory bowel disease, arthritis, osteoarthritis, autoimmune diseases such as rheumatoid arthritis, systemic lupus erythematosus, and connective tissue diseases.

For example, purified IL-10 has been shown in vitro to suppress certain types of viral infections. U.S. Pat. No. 5,665,345 discloses a method for inhibiting replication of the human immunodeficiency virus, retro-viruses, and Kaposi sarcoma in human cells by administering IL-10.

IL-10 has also been suggested for use in the treatment of certain cancers. U.S. Pat. No. 5,570,190 discloses administering exogenous IL-10 to treat mammals suffering from acute myelogenous leukemia and acute lymphocytic leukemia. IL-10 is said to be administered either in the purified or recombinant form and is believed to inhibit the proliferation of acute leukemia blast cells.

Similarly, IL-10 was shown to inhibit bone marrow metastasis in severe combined immunodeficient mice.

The above conventional approaches to treating conditions characterized by excessive IL-1 and TNFa production have been limited to administering exogenous purified or recombinant IL-10 intravenously. Since IL-10 is a protein, it is difficult to infuse intravenously into a mammal because proteins often leach out of solution and bind to the plastic or glass used in intravenous administration sets. Also, proteins are often incompatible and precipitate when mixed with physiological solutions such as dextrose or saline. In addition, oral and topical routes are unavailable for IL-10 administration. The oral route is unavailable because protein is degraded in the gastrointestinal tract.

None of the above approaches suggests enhancing endogenous IL-10 production in mammals for prophylaxis and treatment of diseases or conditions.

Further, it is known that IL-10 is a powerful deactivator of macrophages and T cells, and inadequate production has been implicated in various autoimmune and inflammatory disorders.

The present study shows that the present compounds enhance both LPS and PHA stimulated IL-10, and suppress PHA stimulated IL-2 production in PBMC from healthy blood donors. This may have several implications. First, these findings suggest a marked anti-inflammatory net effect of the present compounds by both enhancing the release of the anti-inflammatory cytokine IL10 and by suppressing the release of the inflammatory cytokine IL-2. Second, our findings suggest that the present compounds may modulate both monocyte (i.e. LPS stimulation) and lymphocyte activation (i.e. PHA stimulation). Finally, the in vitro effect of the present compounds on activated PBMC from healthy blood donors may reflect the situation in various patient populations characterized by enhanced inflammatory activation in vivo. In fact, ex vivo activated PBMC from healthy controls, may represent the relevant target cells for therapeutically intervention in vivo in various inflammatory disorders.

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Treatment

This includes any therapeutic application that can benefit a human or non-human animal. The treatment of mammals is particularly preferred. Both human and veterinary treatments are within the scope of the present invention.

Treatment may be in respect of an existing condition or it may be prophylactic. It may be of an adult, a juvenile, an infant, a foetus, or a part of any of the aforesaid (e.g. an organ, tissue, cell, or nucleic acid molecule).

An active agent for use in treatment can be administered via any appropriate route and at any appropriate dosage. Dosages can vary between wide limits, depending upon the nature of the treatment, the age and condition of the individual to be treated, etc. and a physician will ultimately determine appropriate dosages to be used. However, without being bound by any particular dosages, a daily dosage of a compound of the present invention of from 1 µg to 1 mg/kg body weight may be suitable. The dosage may be repeated as often as appropriate. If side effects develop, the amount and/or frequency of the dosage can be reduced, in accordance with good clinical practice.

Polymorphic Form(S)/Asymmetric Carbon(S)

The agent of the present invention may exist in polymorphic form.

The agent of the present invention may contain one or more asymmetric carbon atoms and therefore exists in two or more stereoisomeric forms. Where an agent contains an alkenyl or alkenylene group, cis (E) and trans (Z) isomerism may also occur. The present invention includes the individual stereoisomers of the agent and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the agent or a suitable salt or derivative thereof. An individual enantiomer of a compound of the agent may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Isotopic Variations

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Pro-Drug

It will be appreciated by those skilled in the art that the agent of the present invention may be derived from a prodrug. Prodrugs are entities which may or may not possess pharmacological activity as such, but may be administered (such as orally or parenterally) and thereafter subject to bioactivation (for example metabolised) in the body to form the agent of the present invention which is pharmacologically active. Examples of prodrugs include entities that have certain protected group(s) and which may not possess pharmacological activity as such, but may, in certain instances, be administered (such as orally or parenterally) and thereafter metabolised in the body to form the agent of the present invention which are pharmacologically active.

Pro-Moiety

It will be further appreciated that certain moieties known as "pro-moieties", for example as described in "Design of Prodrugs" by H. Bundgaard, Elsevier, 1985 (the disclosure of which is hereby incorporated by reference), may be placed on appropriate functionalities of the agents. Such prodrugs are also included within the scope of the invention.

Derivative

The term "derivative" or "derivatised" as used herein includes chemical modification of an agent. Illustrative of such chemical modifications would be replacement of hydrogen by a halo group, an alkyl group, an acyl group or an amino group.

Chemical Modification

In one embodiment of the present invention, the agent may be a chemically modified agent.

The chemical modification of an agent of the present invention may either enhance or reduce hydrogen bonding interaction, charge interaction, hydrophobic interaction, Van Der Waals interaction or dipole interaction between the agent and the target.

In one aspect, the identified agent may act as a model (for example, a template) for the development of other compounds.

The present invention will now be described in further detail in the following examples.

EXAMPLES

The phospholipids, triacylglycerides and other lipids (natural or non-natural) of the present invention (including the lipids proposed in section 2.3) incorporating the described fatty acids may display similar therapeutic and biological properties to the fatty acids such as TTA. Thus, a number of phospholipids, triacylglycerides and other non-natural lipids containing thia-fatty acid derivatives were synthesized. In vivo experiments (in male Wistar rats) were conducted on some of the examples in order to compare their biological effect (with respect to plasma lipid levels and hepatic fatty acid oxidation) against TTA 3. A further in vivo study was conducted wherein TTA and TTA phospholipids were incorporated into liposomes to facilitate intravenous administration.

Synthesis of the Fatty Acids

Fatty acid derivatives for use in accordance with the present invention may be synthesised in accordance with the teaching of WO01/68502.

The strategy for synthesizing fatty acids 3 and 4 is given in Scheme 1. Firstly, the condensation of 2-mercaptoacetic acid and tetradecyl bromide in the presence of sodium methoxide yields, after acidification, TTA as a colourless solid in 82% yield.

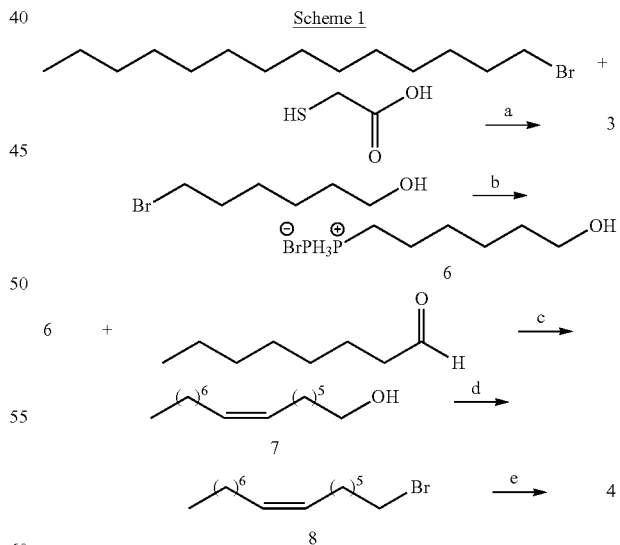

Scheme 1

(a) NaOMe, MeOH, r.t., 2 d; then H$^+$, 82%; (b) PPh$_3$, AcOH, reflux, 6 d, 98%;
(c) NaH, DMSO, then octaldehyde, 0° C., 54%; (d) PBr$_3$, pyridine, Et$_2$O, 70%;
(e) 2-mercaptoacetic acid, NaOMe, MeOH then 8, 96%.

The synthesis of cis-alkene analogue 4 proceeds with a Wittig reaction between phosphonium salt 6 and 1-octanal to afford cis-alkene alcohol 7 (59% yield).[7] Bromination of the alcohol and subsequent reaction with the disodium salt of 2-mercaptoacetic acid yielded the desired fatty acid dTTA 4 (67% for the 2 steps).

Because of uncertainty of the cis/trans selectivity of the Wittig reaction a more cis-selective approach was utilized (Scheme 2). Thus the acetate 9 was hydrolysed with p-TsOH, the resultant primary alcohol THP-protected and the bromide transformed into an iodide via a Finkelstein halogen exchange reaction thereby affording 10 in a good 70% yield for the 3 steps. Iodide 10 was then reacted with the in situ generated alkyl lithiate of 11 giving the protected alkynyl alcohol 12 (76% yield). At this stage the alkene was generated by the cis-selective Lindlar hydrogenation, which proceeded smoothly and in good yield (93%). GC-MS analysis showed homogeneity of the cis moiety. The protected alcohol was transformed in one step to the bromide 8 which was subsequently treated with 2-mercaptoacetic acid in the presence of base to afford the desired fatty acid 4 (dTTA) in 74% yield (2 steps).

Alkyne analogue 5 was synthesized in a similar manner as above. THP-protection of 10-bromodecan-1-ol yielded 14 (74% yield) (Scheme 3).[8] The resultant bromide 14 was then treated with lithium acetylide giving terminal alkyne 15 in 65% yield.[9] Deprotonation of the alkyne with n-butyl lithium allowed by treatment of the resultant lithiate with ethyl iodide in the presence of HMPA afforded the alkylated alkyne 16.[9] The synthesis was completed in a manner analogous to the synthesis of 4 giving the desired tTTA 5 in an overall 35% yield.

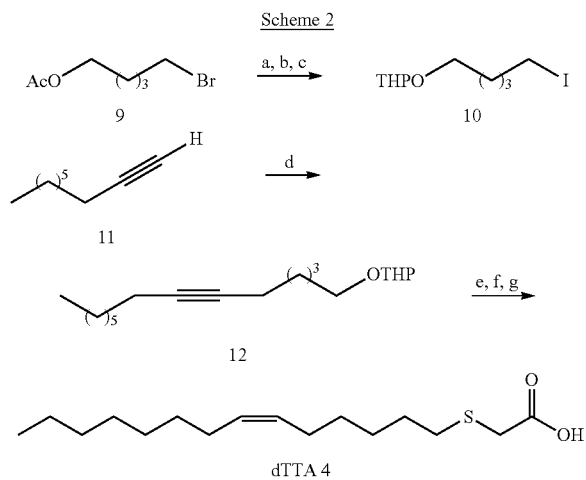

Scheme 2

(a) pTsOH, MeOH, Δ; (b) DHP, PPTS, CH$_2$Cl$_2$, r.t; (c) NaI, acetone, Δ, >70% for 3 steps; (d) n-BuLi, THF/HMPA, 0° C., then 2-(3-iodopentoxy)tetrahydropyran, 76%; (e) Lindlar catalyst, H$_2$, quinnoline, hexanes, 93%; (f) PPh$_3$Br$_2$, PPh$_3$, CH$_2$Cl$_2$, 0° C., 86%; (g) 2-mercaptoacetic acid, NaOMe, MeOH, then 8, >85%

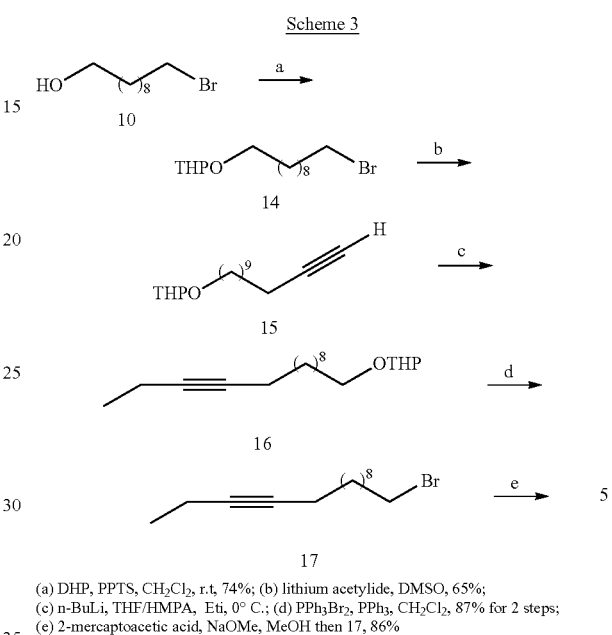

Scheme 3

(a) DHP, PPTS, CH$_2$Cl$_2$, r.t, 74%; (b) lithium acetylide, DMSO, 65%; (c) n-BuLi, THF/HMPA, Eti, 0° C.; (d) PPh$_3$Br$_2$, PPh$_3$, CH$_2$Cl$_2$, 87% for 2 steps; (e) 2-mercaptoacetic acid, NaOMe, MeOH then 17, 86%

2.2 Synthesis of Phospholipid Derivatives

The synthesis of phosphatidylcholine (PC) derivative 1,2-ditetradecylthioacetoyl-sn-glycero-3-phosphocholine (TTA-PC, 18) is shown in Scheme 4. The analogues dTTA-PC 19 and tTTA-PC, 20 were synthesized in analogous manner.

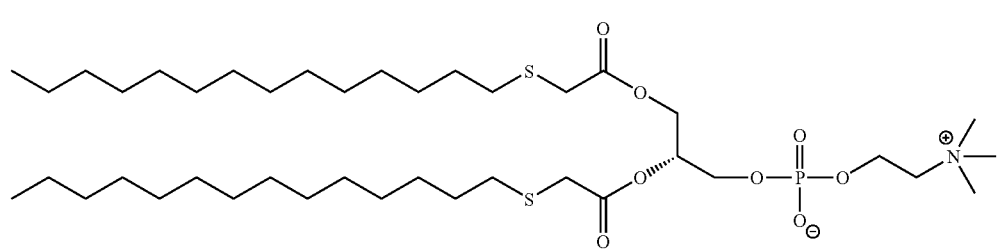

TTA-PC

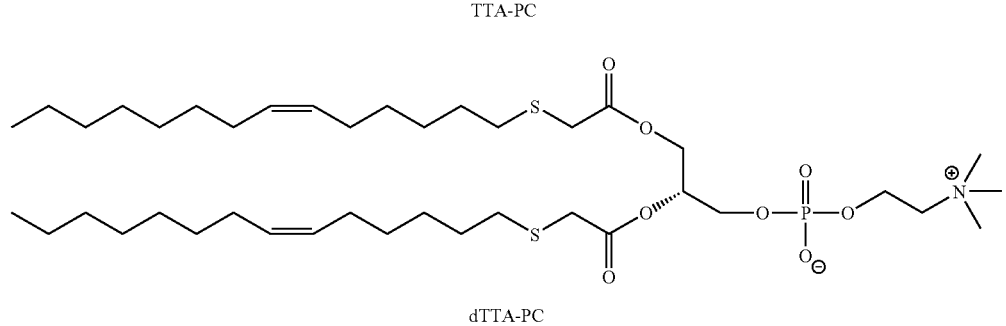

dTTA-PC

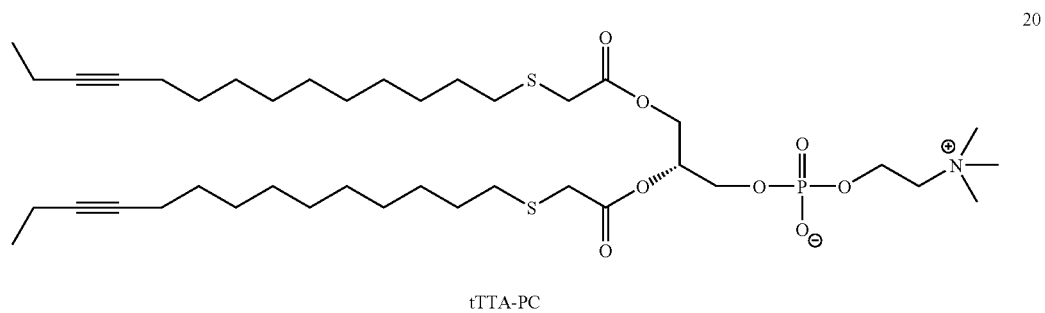
tTTA-PC
The acylation of sn-glycero-3-phosphocholine (GPC) with activated fatty acids, such as fatty acid imidazolides, is a standard procedure in phosphatidylcholine synthesis.[20] It is usually carried out in the presence of DMSO anion with DMSO as solvent. No racemisation was reported.[10]
Scheme 4
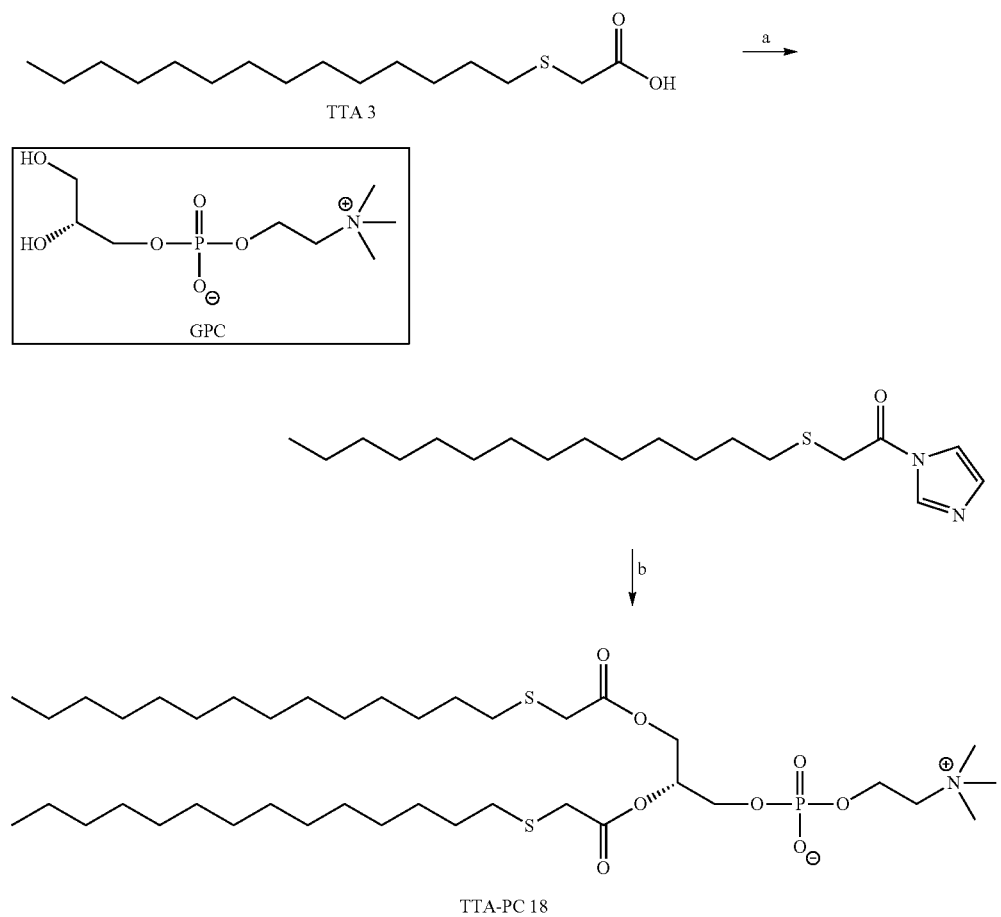
TTA-PC 18
(a) CDI, CHCl$_3$; (b) GPC·CdCl$_2$, DMSO, DBU; 5 h, 56%

Thus in a slight variation of the literature procedure[10] TTA 3 was activated as the imidazolide with N,N'-carbonyldiimidazolide (CDI). sn-Glycero-3-phosphocholine (GPC), as the cadmium (II) adduct, in the presence of DBU (a hindered base which prevents racemisation) was reacted with this imidazolide affording after work-up and purification, the desired TTA-PC, 18 as a yellowish waxy solid in 56% yield Similarly, dTTA-PC, 19 and tTTA-PC, 20, were obtained in 65 and 57% yield respectively.

The synthesis of phosphatidylethanolamine (PE) derivative 1,2-ditetradecylthioacetoyl-sn-glycero-3-phosphoetaanolamine (TFA-PE, 21) is shown in Scheme 4. The analogues dTTA-PE, 22 and tTTA-PE, 23 were synthesized in an analogous manner.

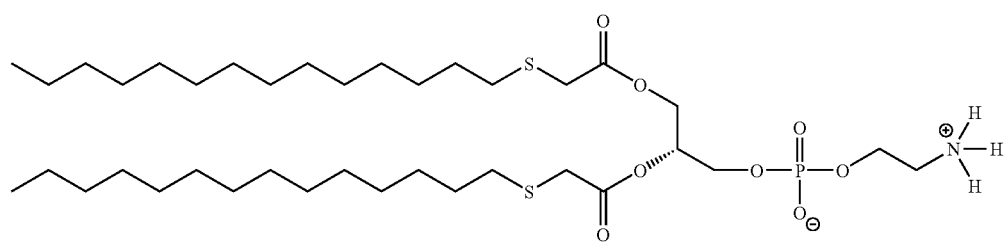

TTA-PE   21

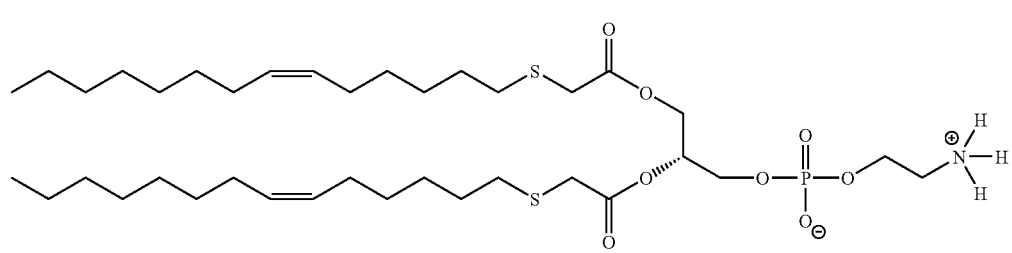

dTTA-PE   22

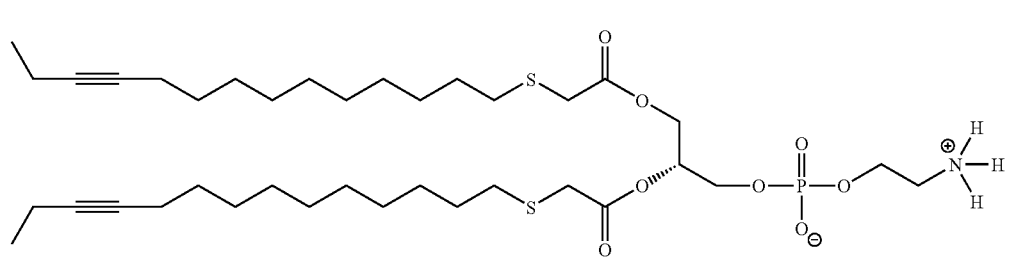

tTTA-PE   23

Slight modification to a procedure by Wang et al.[11] effected the required enzymatic transphosphatidylation from phosphatidylcholine to phosphatidylethanolamine.

Scheme 5

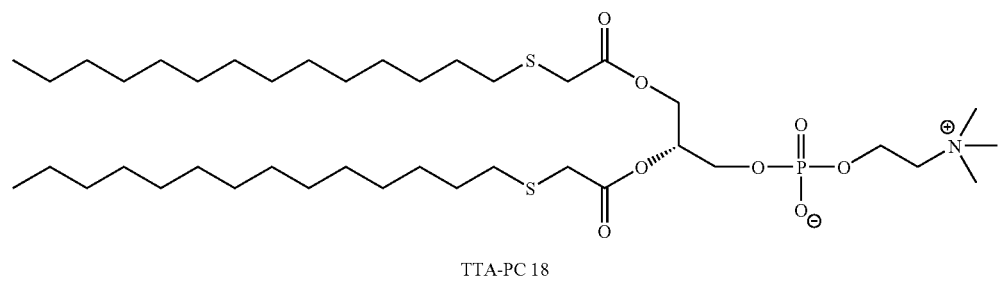

TTA-PC 18

↓a

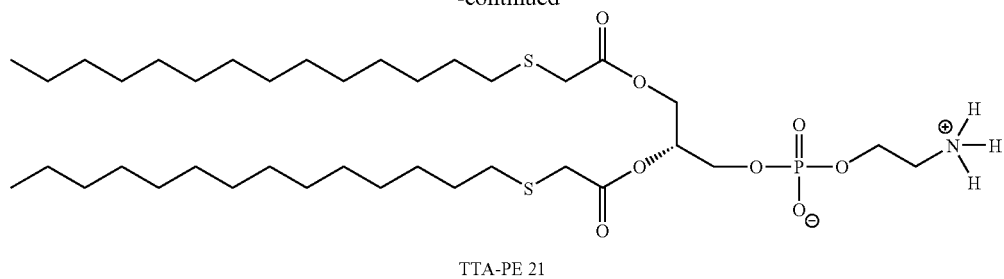

TTA-PE 21

(a) PLD, 30° C., pH 6.5, biphasic system, ethanolamine, 4 h, 94%

Starting from synthesized TTA-PC, 18, TTA-PE, 21 was afforded in good yield (94%) as a pale yellow, waxy solid through enzymatic transphosphatidylation with phospholipase D (PLD) in the presence of excess ethanolamine. Similarly, dTTA-PE, 22 and tTTA-PE 23, were obtained in 89 and 86% yields respectively.

Triacylglycerides, TTA-TAG 24, dTTA-TAG 25, and tTTA-TAG 26, were synthesized by coupling TTA 3, dTTA 4 and tTTA 5 respectively, to glycerol using HBTU/DMAP coupling condition. The desired triglycerides were obtained in good yields (e.g. TTA-TAG 24 in 85% yield).

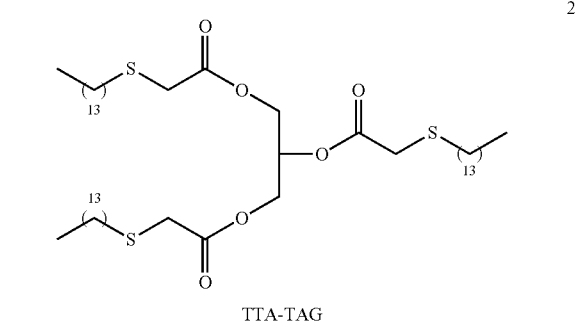

TTA-TAG 24

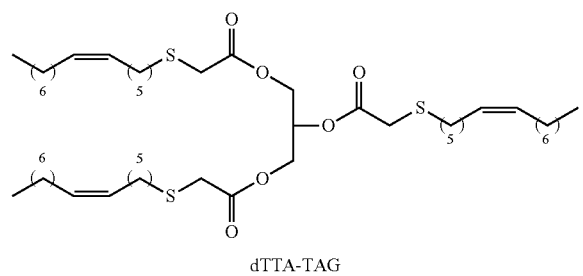

dTTA-TAG 25

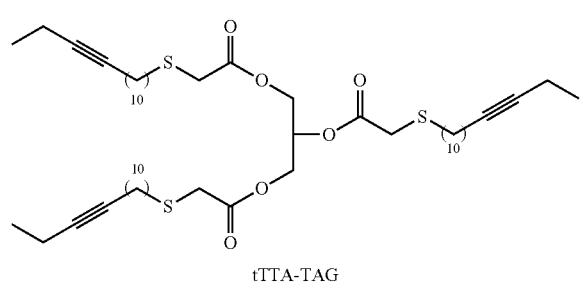

tTTA-TAG 26

2.2.3 Biological Results

Male wistar rats (4-5 rats in each treatment group) were fed TTA, TTA-PC or TTA-TAG at equimolar doses of TTA (1 mmole/day/kg body weight) for 6 days. Control rats received only 0.5% CMC. The rats were sacrificed and evaluated for lipid lowering effects, increased fatty acid oxidation, and activity of key mitochondrian enzymes, carnitine palmitoyl-transferase-II, 3-hydroxy-3-methylglutharyl-CoA synthase and fatty acyl-CoA oxidases.

In a further study, Male wistar rats (4 rats in each treatment group) were injected through the tail vein with liposomes containing TTA (60 μmoles TTA), TTA-PC (50 μmoles TTA) or no TTA (DMPC). 1.5 or 3 hours after injection the rats were killed, plasma collected and triacylglycerol and cholesterol levels determined.

Lipid Lowering Effects of Esterified TTA.

As can be seen from Table 1 all treatments resulted in a significant decrease in plasma triacylglycerol and cholesterol levels compared to the control. The largest decrease (60%) was effected by TTA-PC, which decreased plasma triacylglycerol levels significantly more than non-esterified TTA.

TABLE 1

Effect of esterified and non-esterified TTA on plasma lipids in male Wistar rats (mmol/L).

| Treatment | Triacyl-glycerol | Cholesterol |
|---|---|---|
| Control | 1.20 ± 0.35 | 1.84 ± 0.25 |
| TTA | 0.64 ± 0.31[a] | 1.14 ± 0.23[a] |
| TTA-PC | 0.47 ± 0.21[a,b] | 0.74 ± 0.20[a] |
| TTA-TAG | 0.56 ± 0.21[a] | 1.18 ± 0.12[a] |

Male wistar rats (4-5 rats in each treatment group) were fed TTA, TTA-PC or TTA-TAG at equimolar doses of TTA (1 mmole/day/kg body weight) for 6 days.
Control rats received only 0.5% CMC.
[a]Significantly different from control (0.5% CMC), $p < 0.05$.
[b]Significantly different from unesterified TTA, $p < 0.05$.

Esterified TTA Decrease the Hepatic Lipid Content.

As can be seen from Table 2 feeding esterified TTA resulted in a significant decrease in the hepatic triacylglycerol level compared to the control and the largest decrease (30%) was effected by TTA-PC. This is indicative of a beneficial effect on pathological states associated with fatty liver.

TABLE 2

Effect of esterified and non-esterifled TTA on hepatic triacylglycerol content in male Wistar rats (μmol/mg protein).

| Treatment | Triacylglycerol |
|---|---|
| Control | 3.71 ± 0.50 |
| TTA | 3.09 ± 0.96 |
| TTA-PC | 2.53 ± 0.43[a] |
| TTA-TAG | 2.88 ± 0.50[a] |

Male wistar rats (4-5 rats in each treatment group) were fed TTA, TTA-PC or TTA-TAG at equimolar doses of TTA (1 mmole/day/kg body weight) for 6 days.
Control rats received only 0.5% CMC.
[a]Significantly different from control (0.5% CMC), $p < 0.05$.

Increased Fatty Acid Oxidation by Esterifed TTA.

Increased fatty acid oxidation is an important factor behind the lipid lowering effect of TTA. The increased fatty acid catabolism will decrease the amount of fatty acids available for esterification, and thereby reduce the production and secretion of VLDL by the liver. From Table 3 it can be seen that all three feeding regimes significantly increased the oxidation of palmitoyl-CoenzymeA compared to control, with TTA-PC having a slightly larger effect than the other two treatments.

TABLE 3

Effect of esterified and non-esterified TTA on Palmitoyl-CoA oxidation in rat liver homogenate.

| Treatment | Palm-CoA oxidised (nmol/mg/min) |
|---|---|
| Control | 0.75 ± 0.06 |
| TTA | 1.32 ± 0.22[a] |
| TTA-PC | 1.39 ± 0.15[a] |
| TTA-TAG | 1.37 ± 0.08[a] |

Male wistar rats (4-5 rats in each treatment group) were fed TTA, TTA-PC or TTA-TAG at equimolar doses of TTA (1 mmole/day/kg body weight) for 6 days.
Control rats received only 0.5% CMC.
[a]Significantly different from control (0.5% CMC), $p < 0.05$.

The Activity of Carnitine Palmitoyltransferase-II is Increased by Esterified TTA.

Carnitine palmitoyltransferase-II is an important enzyme for the transport of fatty acids into the mitochondrion. It has been shown that the TTA induced increase in CPT-II activity is an important factor behind the increased fatty acid oxidation effected by TTA. It is seen from Table 4 that all three treatments increased the activity of this enzyme significantly, and that this increase was significantly higher with TTA-PC than with non-esterified TTA.

TABLE 4

Effect of esterified and non-esterified TTA on the mitochondrial carnitine palmitoyltransferase-II activity.

| Treatment | Enzyme activity (nmol/mg/min) |
|---|---|
| Control | 8.32 ± 1.42 |
| TTA | 19.51 ± 5.50[a] |
| TTA-PC | 31.96 ± 2.63[a,b] |
| TTA-TAG | 17.88 ± 4.37[a] |

Male wistar rats (4-5 rats in each treatment group) were fed TTA, TTA-PC or TTA-TAG at equimolar doses of TTA (1 mmole/day/kg body weight) for 6 days.
Control rats received only 0.5% CMC.
[a]Significantly different from control (0.5% CMC), $p < 0.05$.
[b]Significantly different from unesterified TTA, $p < 0.05$.

The Activity of 3-HYDROXY-3-METHYLGLUTHARYL-COA SYNTHASE is Increased by Esterified TTA.

3-Hydroxy-3-methylglutharyl-CoA synthase is considered the rate-limiting enzyme for production of ketone bodies in the mitochondrion. Production of ketone bodies is generally increased with increased fatty acid oxidation, providing fuel for energy production in peripheral tissues. The activity of this enzyme was substantially increased by all treatments compared to the control, and the increased activity after TTA-PC feeding was more than three times as large as after feeding non-esterified TTA (Table 5).

TABLE 5

Effect of esterified and non-esterifled TTA on the 3-Hydroxy-3-methylglutharyl-CoA synthase activity in rat liver homogenate.

| Treatment | Enzyme activity (nmol/mg/min) |
|---|---|
| Control | 28.23 ± 4.43 |
| TTA | 45.72 ± 5.98[a] |
| TTA-PC | 97.77 ± 20.51[a,b] |
| TTA-TAG | 40.35 ± 6.16[a] |

Male wistar rats (4-5 rats in each treatment group) were fed TTA, TTA-PC or TTA-TAG at equimolar doses of TTA (1 mmole/day/kg body weight) for 6 days.
Control rats received only 0.5% CMC.
[a]Significantly different from control (0.5% CMC), $p < 0.05$.
[b]Significantly different from unesterified TTA, $p < 0.05$.

The Activity of Fatty ACYL-COA OXIDASE is Increased by Esterified TTA.

Fatty acyl-CoA oxidase is the rate determining enzyme in the peroxisomal oxidation of fatty acids in rodents. It is one of many enzymes whose gene expression is regulated by the transcription factor PPARα, an important transcription factor in the regulation of lipid catabolism. The enzyme is considered as an excellent marker for compounds that are ligands of PPARα. The activity of this enzyme was increased by all treatments compared to the control, and the increased activity after PC-TTA feeding was significantly higher than after feeding non-esterified TTA (Table 6).

TABLE 6

Effect of esterified and non-esterifled TTA on the Fatty acyl-CoA oxidase activity in rat liver homogenate.

| Treatment | Enzyme activity (nmol/mg/min) |
|---|---|
| Control | 16.50 ± 4.74 |
| TTA | 63.10 ± 35.84[a] |
| TTA-PC | 129.48 ± 15.08[a,b] |
| TTA-TAG | 49.87 ± 22.51[a] |

Male wistar rats (4-5 rats in each treatment group) were fed TTA, TTA-PC or TTA-TAG at equimolar doses of TTA (1 mmole/day/kg body weight) for 6 days.
Control rats received only 0.5% CMC.
[a]Significantly different from control (0.5% CMC), $p < 0.05$.
[b]Significantly different from unesterified TTA, $p < 0.05$.

TTA and PC-TTA Formulated in Liposomes Decrease Plasma Lipids.

Formulation of TTA into liposomes allows for a higher TTA concentration for intravenous injections than in alternative solutions. TTA or TTA-PC was incorporated into liposomes and compared with DMPC liposomes not containing TFA. When determining the plasma levels of triacylglycerol and cholesterol, 1.5 or 3 hours after injection, it can be seen from Table 7 that both TTA and TTA-PC injected in liposomes will lower plasma cholesterol and triacylglycerol compared to DMPC, and that the decreased triacylglycerol levels may be significantly lower than after DMPC injection.

TABLE 7

Effect of esterified and non-esterified TTA containing liposomes on plasma lipids in male Wistar rats (mmol/L).

| Formulation | Triacyl-glycerol 1.5 h | Triacyl-glycerol, 3 h | Cholesterol 1.5 h | Cholesterol 3 h |
|---|---|---|---|---|
| DMPC liposomes | — | 1.97 ± 0.28 | — | 1.80 ± 0.24 |
| TTA liposomes | 1.68 ± 0.20 | 1.38 ± 0.28[a] | 1.56 ± 0.09 | 1.58 ± 0.08 |
| TTA-PC liposomes | 1.00 ± 0.14[a] | 1.69 ± 0.60 | 1.67 ± 0.31 | 1.52 ± 0.29 |

Male wistar rats (4 rats in each treatment group) were injected through the tail vein with liposomes containing TTA (60 μmoles TTA), TTA-PC (50 μmoles TTA) or no TTA (DMPC/SA). 1.5 or 3 hours after injection the rats were killed, plasma collected and triacylglycerol and cholesterol levels determined.
[a]Significantly different from DMPC, $p < 0.05$.

2.2.4 Discussion: Biological Effects

The metabolic syndrome is a complex condition characterised by impaired insulin sensitivity, blood lipid abnormalities (elevated TAG with depressed HDL, elevated small dense LDL and prolonged post-prandial lipaemia), abdominal obesity and hypertension This condition is linked to elevated plasma fatty acid levels and accumulation of triacylglycerol in skeletal muscles. Abnormalities in lipid metabolism are central to the development of these disorders. The regulation of this metabolism is complex and influenced by a range of lipid metabolites and mediators and various transcription factors, representing a complex interplay which is far from understood.

The link between obesity and type 2 diabetes is due to adverse effects of excess body fat on systemic responsiveness to insulin, resulting in impaired action of insulin for both carbohydrate and lipid metabolism, which leads to a compensatory hyperinsulinemia. Adipose tissue mass is a key determinant for the development and pathogenesis of insulin resistance and the metabolic syndrome. Whilst in its most overt form insulin resistance manifests as frank diabetes, less severe degrees of insulin resistance result in the multi-component disorder that has been termed metabolic syndrome (or syndrome X).

There is convincing evidence that moderate physical activity and a decrease in body weight improve insulin sensitivity and features of the metabolic syndrome. This is also reflected in a decreased body fat mass. Thus, it is strong reasons to believe that reductions in adipose tissue mass, triacylglycerol content of skeletal muscles and decreased plasma fatty acid levels will beneficially affect these lipid disorders and improve insulin sensitivity.

The metabolic syndrome has now been defined as a clinical entity both by the World Health Organization and by the American National Cholesterol Education Program (NCEP) Adult Treatment Panel (ATP III) [Curr Opin Lipidol, Volume 14(3), pp 329-332]. Both definitions reflect the heterogeneity of the syndrome. The World Health Organization definition includes impaired glucose tolerance or type 2 diabetes, and/or insulin resistance, plus two of the following: abdominal obesity, dyslipidemia, hypertension and microalbuminuria The NCEP definition, on the other hand, includes three or more of the following: elevated fasting plasma glucose level (above 6.0 mmol/l), elevated triglyceride concentration (>1.6 mmol/l), low HDL cholesterol (women <1.3 mmol/l, men <1 mmol/l), elevated blood pressure (>=130/85 mmHg) and abdominal obesity (waist circumference >102 cm in men and >88 cm in women).

These diseases are increasing in incidence and prevalence (both in industrialized and in developing countries), and becoming an increasing source of mortality, morbidity, and medical costs to individuals, corporations, and society. They are often frustratingly difficult to treat. From a scientific perspective, these diseases and conditions are complex in their origins and pathobiologies, and are only partially understood.

The past five years has seen the introduction of novel, breakthrough drugs for both-type 2 diabetes and obesity. These include such drugs as rosiglitazone (SmithKline Beecham's Avandia), and pioglitazone (Lilly's Actos) for type 2 diabetes and orlistat Roche's Xenical) and sibutramine (Knoll AG's Meridia) for obesity.

The compounds of the present invention (TTA-PC and TTA-TAG) have been demonstrated to increase fatty acid oxidation and decrease plasma and hepatic lipid levels. Due to the structural relations of these novel lipids with respect to TTA and the similar expected biological metabolic pathways which they may follow it is anticipated that the compounds of the present invention can be used for the prevention and/or treatment of obesity, diabetes, hyperinsulinemia and fatty liver and hypertension. These favourable effects have also been demonstrated for the parent fatty acid analogue tetradecylthioacetic acid (TTA), which has qualitatively similar effects on fatty acid oxidation and plasma and hepatic lipids. TTA has been demonstrated to ameliorate hyperinsulinemia, hyperglycemia, fatty liver and obesity (WO 01/68582)

Fatty acid analogues substituted with S or Se have been demonstrated to have antioxidant properties due to the presence of the heteroatom (WO 97/03663). Due to the similar molecular structure the compounds of the present invention are also anticipated to have anti-oxidant properties, and thus may inhibit the oxidative modification of low density lipoproteins.

Due to the similarity in molecular structure with S and Se substituted fatty acids the compounds of the present invention is also anticipated to have anti-inflammatory properties as has been demonstrated for tetradecylthioacetic acid and tetradecylselenoacetic acid (WO 02/43728).

The process of restenosis and atherosclerosis is related, but not similar. Restenosis is a response to vessel injury after the use of balloon coronary angioplasty (PTCA) or the insertion of stents in the vessel wall implicating an inflammatory response and oxidative stress. It is a repair process resulting in lumen narrowing due to proliferation and migration of smooth muscle cells in the vessel wall, in addition to changes in amount of collagen and collagen bridging. Thus, it is anticipated that the compounds of the present invention will inhibit the process of restenosis. It is furthermore anticipated that they will be effective in the prevention and/or treatment of inflammatory disorders. (cf. for TTA WO 02/43728)

It is further anticipated that the compounds of the present invention will inhibit the proliferation of specific cancer cells and smooth muscle cells as has been demonstrated for other heterosubstituted fatty acid analogues. Thus, these compounds may be effective in the prevention and/or treatment of proliferative skin disorders, which are related to increased proliferation and diminished differentiation of keratinocytes. (cf. for TTA WO 02/26218).

It is furthermore anticipated that they will be effective in the inhibition of the growth of tumours and may be used for the inhibition of the metastatic properties of a tumour, i.e. to inhibit the formation of secondary tumours. (cf. for TTA WO 02/03983)

2.3 Experimental

2.3.1 Chemistry Experimental

General Procedure:

Dried $CH_2Cl_2$ was distilled with phosphorous pentoxide, other solvents were purchased predried as required. Thin layer chromatography (TLC) was performed on pre-coated Merck-Kieselgel 60 $F_{254}$ aluminium backed plated and revealed with ultraviolet light, iodine, acidic ammonium molybdate(IV), acidic ethanolic vanillin, or other agents as appropriate. Flash column chromatography was accomplished on Merck-Kieselgel 60 (230-400 mesh). Infared Spectra were recorded on Jasco FT/IR 620 using NaCl plates. Mass spectra were recorded using Bruker Esquire 3000, VG-7070B or JEOL SX-102 instruments. $^1H$ & $^{13}C$ NMR spectra were recorded on either Bruker DRX300, Advance 400 Ultrashield™ or Jeol GX-270Q machines using residual isotopic solvent as an internal reference ($CHCl_3$, $\delta_H$=7.26 ppm).(s=singlet, d=doublet, t=triplet, q=quartet, quin=quintet). All chemicals were purchased from Sigma-Aldrich or Lancaster if not otherwise stated. FCC refers to flash column chromatography on silica gel, Tetradecylthioacetic Acid (TTA) 3

3

Thioacetic acid (3.32 g, 36.0 mmol) in MeOH (150 ml) was treated successively with NaOMe (25% in MeOH, 12 g, 0.08 mol) and tetradecyl bromide (10.0 g, 0.036 mol) and stirred vigorously at room temperature for 48 h. The mixture was poured into $H_2O$, acidified to pH 2 (conc. HCl) and extracted with diethyl ether. Drying ($MgSO_4$) and concentration in vacuo afforded a crude solid which was purified by flash column chromatography (FCC) (25% EtOAc in hexanes to 35% EtOAc in hexanes) to yield 3 as a colourless solid (8.6 g, 82%); m.p. 64-66° C. (lit. 65-67° C.); $\delta_H$(300 M, $CDCl_3$) 0.89 (t, 3H, J=6.7 Hz), 1.27 (m, 22H), 1.32 (m, 2H), 1.61 (m, 2H), 2.67 (t, 2H, J 7.4) and 3.28 (s, 2H); MS (FAB$^+$) 289 (M+H)$^+$, 288 M$^+$; HRMS: Found M$^+$0288.211823. Calc. for $C_{16}H_{32}O_2S$: M$^+$0288.212302.

(6-Hydroxyphexyl)triphenylphosphonium bromide 6

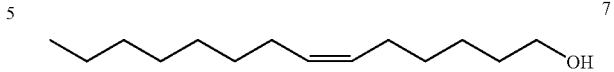

6

6-Bromo-1-hexanol (5.0 g, 27.6 mmol) and triphenylphosphine (7.6 g, 28.2 mmol) in acetonitrile (100 ml) was refluxed for 6 days after which the solvent was removed in vacuo affording crude 6 (12.0 g, 98%); $\delta_H$(300 $CDCl_3$) 1.53 (m, 4H), 1.69 (m, 4H), 3.65 (m, 2H), 3.73 (m, 3H), 7.7-7.9 (m, 15H).

(Z)-6-Tetradecen-1-ol 7

7

(6-Hydroxyhexyl)triphenylphosphonium bromide 6 (0.5 g, 1.13 mmol) in warm DMSO (3 ml) was added to THF solution of methylsulfinylmethanide ion (prepared from NaH (57 mg, 2.37 mmol) and DMSO (1 ml) under $N_2$ at 70-75° C. for 80 min) with cooling in an ice-bath. The bright yellow solution of phosphorane was stirred at room temperature for 10 min, then treated with octanal (0.159 g, 1.25 mmol) at 0° C. After stirring for 20 min, the reaction mixture was poured into 5 ml $H_2O$ and extracted several times with ether. Drying with $MgSO_4$ and concentration affords a residue which was purified by FCC (14% EtOAc in hexanes) to yield 7 (0.13 g, 54%, lit. 60%); $\delta_H$(270 MHz, $CDCl_3$) 0.86 (3H, t, J=6.5 Hz), 1.10-1.43 (16H, m), 1.55 (2H, m), 2.00 (4H, m), 3.6 (2H, t, J=6.5 Hz) and 5.3-5.4 (2H, m).

Cis-1-Bromo-tetradec-6-ene 8

8

Alcohol 7 (115 mg, 0.541 mmol) in dichloromethane (100 ml) at 0° C. was treated successively with carbon tetrabromide (395 mg, 1.20 mmol) and triphenylphosphine (312 mg, 1.20 mmol), and allowed to warm to room temperature with stirring over 2 h. The reaction mixture was triturated with water and extracted with methylene chloride, dried ($MgSO_4$) and concentrated in vacuo. The crude product was purified by flash column chromatography using hexanes as an eluent, thus affording pure 8 as a light oil (105 mg, 0.381 mmol, 70%); $\delta_H$(270 MHz, $CDCl_3$); 0.87 (3H, t, J=6.1 Hz), 1.1-1.65 (14H, m), 1.85 (2H, quin, J 7.0), 2.03 (4H, m), 3.4 (2H, t, J 6.8) and 5.35 (4H, m); $\delta_C$(67.5 MHz, $CDCl_3$) 27.06, 27.32 27.72, 27.91, 28.04, 28.96, 29.32, 29.37, 29.71, 29.83, 31.96, 32.82, 34.01, 129.31, 130.47.

Cis-Tetradec-6-enylthioacetic acid (dTTA) 4

4

Thioacetic acid (35 mg, 0.38 mmol) in methanol (20 ml) was treated successively with sodium methoxide (50 mg, 0.9144 mmol) and bromide 8 (105 mg, 0.381 mmol) and stirred at r.t. for 2 d. The reaction mixture was diluted in water and acidified with cold conc. aq. HCl. The aqueous layer was extracted with hexanes, dried ($MgSO_4$) and concentrated invacuo to afford a crude residue was purified by flash column chromatography (eluent gradient elution 65-75% EtOAc in Hexanes) to afford the pure 4 as a viscous oil (105 mg, 0.367 mmol, 96%); $\delta_H$(270 MHz, $CDCl_3$); 0.86 (3H, t, J 6.8), 1.35 (14H, m), 1.60 (2H, m), 2.00 (4H, m), 2.65 (21, t, J 7.4), 3.24 (2H, s), 5.34 (2H, m) and 10.0 (1H, br s); $\delta_C$(67.5 MHz, $CDCl_3$) 14.20, 22.76, 27.09, 27.31, 28.45, 28.89, 29.32, 29.35, 29.35, 29.83, 31.95, 32.82, 33.54, 129.44, 130.36 and 176.77; MS (CI) 304 (M+NH$_4$)$^+$; HRMS: Found [M+NH$_4$]$^+$ 304.230876. Calc. for C$_{16}$H$_{34}$NO$_2$S: [M+NH$_4$]$^+$ 0304.231026.

2-(5-Iodo-pentyloxy)-tetrahydro-pyran 10

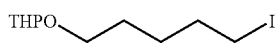

The title compound 10 was synthesized in 3 steps from 5-bromo-pentyl acetate 9 utilizing the method of Bestmann and Gunawardena[10]. Thus 9 (58.8 g, 0.281 mol) yielded pure iodide 10 (54.7 g, 0.183, mol, 65%); $\delta_H$(270 MHz, CDCl$_3$); 1.40-1.90 (12H, m), 3.17 (2H, t, J 6.9), 3.30-3.55 (21H, m), 3.69-3.90 (2H, m) and 4.55 (1H, m); $\delta_C$(67.5 MHz, CDCl$_3$) 7.05, 19.75, 25.54, 27.38, 28.74, 30.82, 33.42, 62.47, 67.28, 69.65, 73.45, 98.97 and 116.07; MS (EI) 297 (M–H)$^+$; HRMS: Found [M–H]$^+$0297.034067. Calc. for C$_{10}$H$_{18}$O$_2$I: [M–H]$^+$0297.035157.

2-Tetradec-6-ynyloxy-tetrahydro-pyran 12

1-Nonyne 11 (1.0 g, 8.06 mmol) in THF (20 ml) was treated with n-BuLi (1.7 M in hexanes, 6.6 ml, 0.011 mmol) at 0° C. and the resulting pale yellow solution stirred for a 15 min. HMPA (15 ml) was then added and the mixture stirred for a further 15 min at 0° C. To the resultant dark yellow/orange solution was then added 10 (3.6 g, 0.0121 mol) at 0° C. which resulted in a immediate colour change in the solution to light yellow. This light yellow solution was stirred at r.t. overnight at which stage it was triturated with water and extracted with hexanes. The hexane extract were well washed with water, dried (MgSO$_4$) and concentrated invacuo to afford a light yellow residue which was purified by flash column chromatography (eluent—8.5% EtOAc in hexanes) to yield a the pure 12 (1.6 g, 70%); $\delta_H$(270 MHz, CDCl$_3$); 0.86 (3H, t, J 6.2), 1.15-1.85 (13H, m), 2.11 (4H, m), 3.30-3.55 (2H, m), 3.69-3.90 (2H, m) and 4.56 (1H, m); $\delta_C$(67.5 MHz, CDCl$_3$) 14.17, 18.82, 18.82, 19.74, 22.71, 25.57, 25.57, 28.91, 28.91, 29.08, 29.24, 29.38, 30.49, 30.84, 31.84, 62.40, 62.40, 67.57, 67.57, 98.90. MS (EI) 295 (M+H)$^+$; HRMS: Found 295.2616 [M+H]$^+$. Calc. for C$_{19}$H$_{35}$O$_2$: 295.263706 [M+H]$^+$.

Cis-1-Bromo-tetradec-6-ene 8

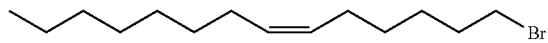

A mixture of alkyne 12 (150 mg, 0.509 mmol), quinoline (0.18 ml, 1.50 mmol) and Lindlar catalyst (Pd, 5% wt % on calcium carbonate, poisoned with lead, 100 mg) was stirred under a H$_2$ atmosphere (balloon pressure) at room temperature for 3 h After removal of the solids residues by filtration through Celite, the filate was washed with water and extracted with hexanes, dried MgSO$_4$) and concentrated to afford a crude residue which was not purified. The residue was dissolved in dichloromethane at 0° C. and the mixture treated successively with triphenylphosphine (52 mg, 0.20 mmol) and triphenylphosphine dibromide (236 mg, 0.56 mmol) and the resultant mixture stirred for 1 h at 0° C. The mixture was then washed with 10% aq. potassium carbonate, water and dried (MgSO$_4$). Concentration afforded a crude residue which was purified by flash column chromatography (eluent—hexanes) to afford the pure 8 (81%); $\delta_H$(270 M CDCl$_3$); 0.87 (3H, t, J=6.1 Hz), 1.1-1.65 (14H, m), 1.85 (2H, quin, J 7.0), 2.03 (4H, m), 3.4 (2H, t, J 6.8) and 5.35 (4H, m); $\delta_C$(67.5 MHz, CDCl$_3$) 27.06, 27.32 27.72, 27.91, 28.04, 28.96, 29.32, 29.37, 29.71, 29.83, 31.96, 32.82, 34.01, 129.31, 130.47.

2-(10-bromodecyloxy)tetrahydropyran 14

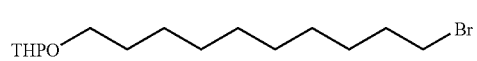

1-Bromodecan-1-ol 13 (5.0 g, 21.1 mmol) was treated with dihydropyran (2.14 g, 25.4 mmol) and pyridinium-p-toluene sulfonate (0.1 g cat.) in anhydrous methylene chloride (100 ml) at 0° C. and stirred at room temperature for 8 h. The reaction was quenched with 10% NaHCO$_3$ and extracted with methylene chloride. The organic extract was washed with brine and water and dried over anhydrous MgSO$_4$. The solvent was removed in vacuo to afford an oil which was purified by FCC (4-8% Et$_2$O in hexanes). Pure 14 was obtained as a viscous oil (5.0 g, 15.5 mmol, 73%); $\delta_H$(270 MHz, CDCl$_3$) 1.27-1.91 (22H, m), 3.36 (2H, t, J=6.9 Hz), 3.34-3.90 (4H, m) and 4.55 (1H, m); MS (FAB$^+$) 321 M$^+$, HMRS: Found, 319.127007 (M–H$^+$). Calc. for C$_{15}$H$_{28}$BrO$_2$, 319.127267 (M–H)$^+$.

2-(Dodec-11-ynyl-1-oxy)tetrahydropyran 15

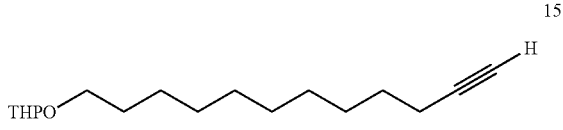

Anhydrous DMSO (15 ml) was added to cooled lithium acetylide (1.47 g, 15.2 mmol) under a dry N$_2$ atmosphere. The mixtutre was stirred for 10 min at 5° C. then treated dropwise with 14 (3 g, 11.3 mmol) in DMSO (4 ml). The resultant mixture was stirred at 5° C. for 3 h, allowed to warm to room temperature overnight and then quenched with iced water followed by several extractions with ether. The ether extracts were washed several times with water, dried over MgSO$_4$ and concentrated in vacuo to give the crude product. Purification by FCC (4% EtOAc in hexanes) yielded pure 15 (1.95 g, 65%); $\delta_H$(270 MHz, CDCl$_3$) 1.20-1.50 (12H, m), 1.50-1.88 (10H, m), 1.95 (1H, t, J=2.6 Hz), 2.19 (2H, dt, J 2.6, 7.0 Hz), 3.35-3.92 (4H, m) and 4.58 (1H, m); HRMS: Found, 267.231735 (M+H)$^+$. Calc. for C$_{17}$H$_{31}$O$_2$: 267.232406 (M+H)$^+$.

2-Tetradec-11-ynyloxy-tetrahydro-pyran 16

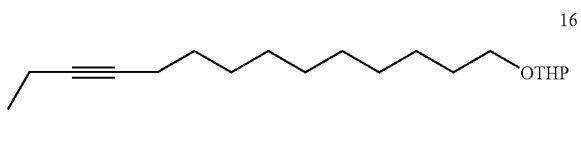

Alkyne 16 was synthesized in an identical manner as alkyne 12. Thus terminal alkyne 15 (5.09 g, 0.0191 mol) and ethyl iodide (5.46 g, 0.031 mol) yielded crude 16 which was not purified but used directly in the next step ie. synthesis of bromide 17.

14-Bromo-tetradec-3-yne 17

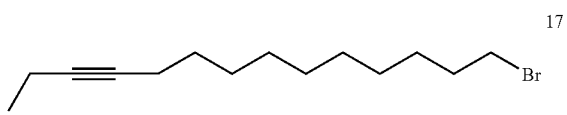

The alkynyl ether 16 (5.62 g, 0.0191 mol) in dichloromethane (150 ml) at 0° C. was treated successively with carbon tetrabromide (8.23 g, 0.0248 mol) and triphenylphosphine (13 g, 0.050 mol) and stirred for 5 h at r.t. The solution was treated with silica gel, the solvent removed invacuo and the dry residue loaded onto a prepared flash column. Elution with hexanes yielded the pure bromide 17 (87% from 15); $\delta_H$ (270 MHz, CDCl$_3$) 1.10 (3H, t, J 7.4), 1.27-1.54 (14H, m), 1.84 (2H, quin, J 7.3), 2.15 (4H, m) and 3.40 (2H, t, J 6.8). $\delta_C$ (100 MHz, CDCl$_3$) 12.82, 14.79, 27.28, 29.23, 29.26, 29.4, 29.53, 29.80, 30.11, 33.04, 79.96 (quartenary) and 82.00 (quartenary).

Tetradec-11-ynylthioacetic acid (tTTA) 5

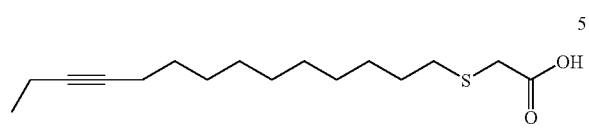

Acid 5 was synthesized in an identical maneer as compounds 3 and 4. Thus bromide 17 (4.4 g, 15.98 mmol) and thioacetic acid (1.5 g, 16.2 mmol) afforded crude acid which was crystallized from hexanes to yield pure acid 5 (3.90 g, 86%) as a white solid; $\delta_H$ (270 MHz, CDCl$_3$) 1.10 (3H, t, J 7.30), 1.20-1.50 (14H), 1.60 (2H, m), 2.15 (4H, m), 2.64 (2H, t, J 7.30), 3.25 (2H, s) and 11.0 (1H, br s); $\delta_C$(67.5 MHz, CDCl$_3$) 12.49, 14.47, 18.80, 28.80, 28.95, 28.95, 29.21, 29.21, 29.21, 29.51, 32.88, 33.56, 79.82, 81.80 and 176.51; MS (CI) 302 [M+NH$_4$]$^+$, HMRS: Found, 302.214964 [+NH$_4$]$^+$. Calc. for C$_{16}$H$_{32}$NO$_2$S: 302.215376 [M+NH$_4$]$^+$.

1,2-Ditetradecylthioacetoyl-sn-glycero-3-Rhosiphocholine (TTA-PC, 18)

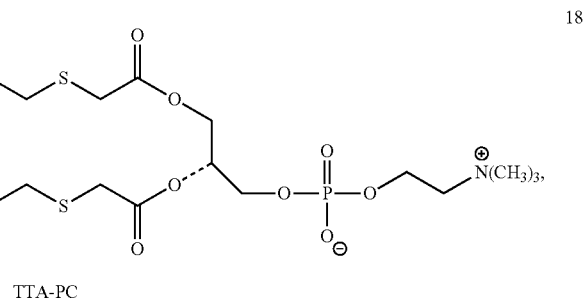

TTA-PC

To a stirred solution of TTA 3 (231 mg, 0.80 mmol) in anhydrous CHCl$_3$ (5 ml) was added N,N'-carbonyldiimidazole (CDI; 162 mg, 1.00 mmol) under a N$_2$ atmosphere. Meanwhile, sn-glycero-3-phosphocholine:cadmium (II) chloride adduct (GPC; 137 mg, 0.30 mmol, 1 eq.) was dissolved in DMSO (5 ml), with a little heating. To this solution was added DBU (120 µl, 0.80 mmol). The CHCl$_3$ solution was transferred to the DMSO solution via a cannula with further CHCl$_3$ (2 ml). After 7 h, the crude reaction mixture was neutralised with 0.1 M acetic acid (20 ml), then extracted into a 2:1 mixture of CHCl$_3$:MeOH (total volume 150 ml), and washed with a 1:1 mixture of H$_2$O:MeOH (100 ml→250 ml stepwise, over five washes), back-extracting each time. The subsequent organic fractions were combined, and concentrated in vacuo, azeotroping the water and methanol with benzene. The residual orange-brown, viscous oil was purified by SiO$_2$ flash column chromatography [CH$_2$Cl$_2$:MeOH:H$_2$O, 77.54:20.23:2.23], to afford TTA-PC 18 as an off-white waxy solid (135 mg, 56%): R$_f$ 0.33 [CH$_2$Cl$_2$:MeOH:H$_2$O, 65:25:4]; $^1$H NMR (270 MHz, CDCl$_3$) $\delta_H$ 0.82 (6 H, t, J=6.5 Hz, 2 CH$_2$CH$_3$), 1.15-1.39 (44 H, 2 m, 22 CH$_2$), 1.47-1.65 (4 H, m, 2 CH$_2$CH$_3$), 2.54-2.61 (4 H, 2×t, J=7.2 Hz, 2 CH$_2$SCH$_2$CO$_2$), 3.20 and 3.23 (2×1 H, 2 s, 2 CH$_2$SCH$_2$CO$_2$), 3.34 (9 H, s, N(CH$_3$)$_3$) 3.59-3.67 (2 H, m, CH$_2$N(CH$_3$)$_3$), 3.87-3.98 (2 H, m, glycerol-C3-H$_{a,b}$), 4.07-4.15 (1 H, dd, $^2$J=12.0 Hz, $^3$J=7.8 Hz, glycerol-C1-H$_b$), 4.26-4.33 (2 H, m, CH$_2$CH$_2$N(CH$_3$)$_3$), 4.34-4.39 (1 H, dd, $^2$J=12.0 Hz, 3J=2.5 Hz, glycerol-C1-H$_a$), 5.13-5.22 (1 H, m, glycerol-C2-H), $^{13}$C NMR (67.5 MHz, CDCl$_3$) $\delta_C$ 170.44, 170.19 (2 CO), 71.66 (d, J$_{CP}$=7.74 Hz, POCH$_2$CHCH$_2$), 66.30 (d, J$_{CP}$=4.67 Hz, POCH$_2$CH$_2$N (CH$_3$)$_3$), 63.63 (POCH$_2$CHCH$_2$), 63.28 (d, J$_{CP}$=25.2 Hz, POCH$_2$ [glycerol]), 59.38 (d, J$_{CP}$=21.2 Hz, POCH$_2$ [choline]), 54.42 (N(CH$_3$)$_3$), 33.66, 33.50, 32.80, 32.73, 29.77 (40×CH$_2$), 29.43, 28.91, 28.89, 28.89, 22.75, 14.18 (2 CH$_3$); m/z FAB+) 820 ([M+Na]$^+$), 798 ([M+H]$^+$); HRMS: Calculated for C$_{40}$H$_{81}$NO$_8$PS$_2$:798.514126. Found: 798.510895 ([M+H]$^+$).

1,2-Di(Cis-tetradec-6-enylthioacetoyl)-sn-glycero-3-phosphocholine (dTTA-PC, 19)

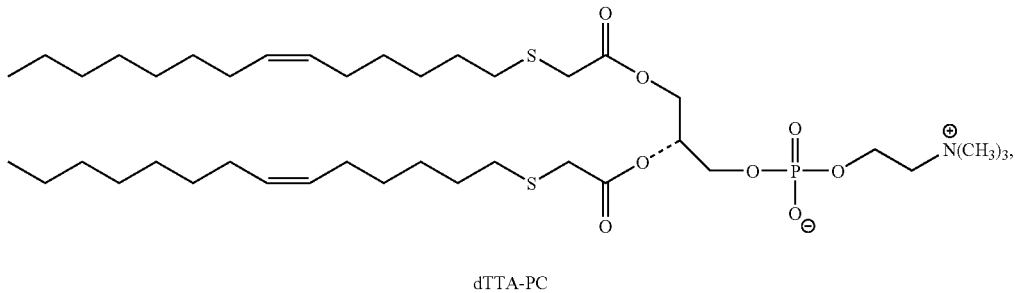

dTTA-PC

To a stirred solution of dTTA 4 (229 mg, 0.80 mmol) in anhydrous CHCl$_3$ (5 ml) was added N,N'-carbonyldiimidazole (CDI; 162 mg, 1.00 mmol) under a N$_2$ atmosphere. Meanwhile, sn-glycero-3-phosphocholine:cadmium (II) chloride adduct (GPC; 137 mg, 0.30 mmol, 1 eq.) was dissolved in DMSO (5 ml), with a little heating. To this solution was added DBU (120 μl, 0.80 mmol). The CHCl$_3$ solution was transferred to the DMSO solution via a cannula with further CHCl$_3$ (2 ml). After 7 h, the crude reaction mixture was neutralised with 0.1 M acetic acid (20 ml), then extracted into a 2:1 mixture of CHCl$_3$:MeOH (total volume 150 ml), and washed with a 1:1 mixture of H$_2$O:MeOH (100 ml→250 ml stepwise, over five washes), back-extracting each time. The subsequent organic fractions were combined, and concentrated in vacuo, azeotroping the water and methanol with benzene. The residual orange-brown, viscous oil was purified by SiO$_2$ flash column chromatography [CH$_2$Cl$_2$:MeOH:H$_2$O, 77.54:20.23:2.23], to afford dTTA-PC 19 as an off-white waxy solid (155 mg, 65%): R$_f$ 0.33 [CH$_2$Cl$_2$:MeOH:H$_2$O, 65:25:4]; $^1$H NMR (270 MHz, CDCl$_3$) δ$_H$ 0.82 (6 H, t, J=6.5 Hz, 2 CH$_2$CH$_3$), 1.15-1.39 (28 H, 2 m, 14 CH$_2$), 1.47-1.65 (4 H, m, 2 CH$_2$CH$_3$), 1.92-2.07 (8 H, m, 2 CH$_2$CH=CHCH$_2$), 2.54-2.61 (4H, 2xt, J=7.2 Hz, 2 CH$_2$SCH$_2$CO$_2$), 3.20 and 3.23 (2×1H, 2 s, 2 CH$_2$SCH$_2$CO$_2$), 3.34 (9 H, s, N(CH$_3$)$_3$) 3.59-3.67 (2 H, m, CH$_2$N(CH$_3$)$_3$), 3.87-3.98 (2 H, m, glycerol-C3-H$_{a,b}$), 4.07-4.15 (1 H, dd, $^2$J=12.0 Hz, $^3$J=7.8 Hz, glycerol-C1-H$_b$), 4.26-4.33 (2 H, m, CH$_2$CH$_2$N(CH$_3$)$_3$), 4.34-4.39 (1 H, dd, $^2$J=12.0 Hz, $^3$J=2.5 Hz, glycerol-C1-H$_a$), 5.13-5.27 (1 H, m, glycerol-C2-H) and 5.25-5.38 (4H, m, 2 CH=CH); $^{13}$C NMR (67.5 MHz, CDCl$_3$) δ$_C$ 170.36, 170.09 (2 CO), 130.29, 129.38 (2 C=C), 71.58 (d, J$_{CP}$=7.74 Hz, POCH$_2$CHCH$_2$), 66.30 (d, J$_{CP}$=4.67 Hz, POCH$_2$CH$_2$N(CH$_3$)$_3$), 63.63 (POCH$_2$CHCH$_2$), 63.16 (d, J$_{CP}$=25.2 Hz, POCH$_2$ [glycerol]), 59.38 (d, J$_{CP}$=21.2 Hz, POCH$_2$ [choline]), 54.42 (N(CH$_3$)$_3$), 33.60, 33.46, 32.72, 32.64, 31.91, 29.77, 29.40, 29.32, 29.28, 28.96, 28.47, 27.29, 27.11, 22.75 and 14.18 (2 CH$_3$); m/z (FAB+) 816 ([M+Na]$^+$), 794 ([M+H]$^+$); HRMS: Calculated for C$_{40}$H$_{77}$NO$_8$PS$_2$:794.482826. Found: 794.480957 ([M+H]$^+$).

1,2-Di(tetradec-11-ynylthioacetoyl)-sn-glycero-3-phosphocholine (tTTA-PC, 20)

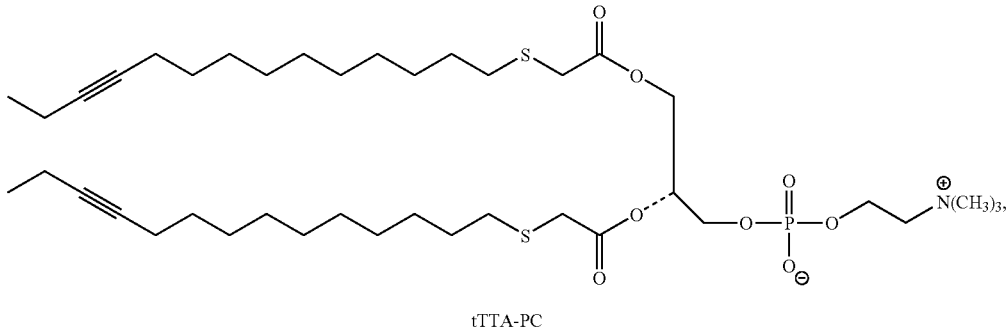

tTTA-PC

To a stirred solution of tTTA 5 (228 mg, 0.80 mmol) in anhydrous CHCl$_3$ (5 ml) was added N,N'-carbonyldiimidazole (CDI; 162 mg, 1.00 mmol) under a N$_2$ atmosphere. Meanwhile, sn-glycero-3-phosphocholine:cadmium (II) chloride adduct (GPC; 137 mg, 0.30 mmol, 1 eq.) was dissolved in DMSO (5 ml), with a little heating. To this solution was added DBU (120 μl, 0.80 mmol). The CHCl$_3$ solution was transferred to the DMSO solution via a cannula with further CHCl$_3$ (2 ml). After 7 h, the crude reaction mixture was neutralised with 0.1 M acetic acid (20 ml), then extracted into a 2:1 mixture of CHCl$_3$:MeOH (total volume 150 ml), and washed with a 1:1 mixture of H$_2$O:MeOH (100 ml→250 ml stepwise, over five washes), back-extracting each time. The subsequent organic fractions were combined, and concentrated in vacuo, azeotroping the water and methanol with benzene. The residual orange-brown, viscous oil was purified by SiO$_2$ flash column chromatography [CH$_2$Cl$_2$:MeOH:H$_2$O, 77.54:20.23:2.23], to afford tTTA-PC 20 as an off-white waxy solid (135 mg, 57%): R$_f$ 0.33 [CH$_2$Cl$_2$:MeOH:H$_2$O, 65:25:4]; $^1$H NMR (270 MHz, CDCl$_3$) δ$_H$ 1.09 (6 H, t, J=6.9 Hz, 2 CH$_2$CH$_3$), 1.15-1.60 (32 H, m, 16 CH$_2$), 2.0-2.17 (CH$_2$C≡CCH$_2$), 2.56 (4 H, 2xt, J=7.2 Hz, 2 CH$_2$SCH$_2$CO$_2$), 3.20 and 3.23 (2×1 H, 2 s, 2 CH$_2$SCH$_2$CO$_2$), 3.34 (9 H, s, N(CH$_3$)$_3$), 3.59-3.67 (2 H, m, CH$_2$N(CH$_3$)$_3$), 3.87-3.98 (2 H, m, glycerol-C3-H$_{a,b}$), 4.07-4.15 (1 H, dd, $^2J$=12.0 Hz, $^3J$=7.8 Hz, glycerol-C1-H$_b$), 4.26-4.33 (2 H, m, CH$_2$CH$_2$N(CH$_3$)$_3$), 4.34-4.39 (1 H, dd, $^2J$=12.0 Hz, $^3J$=2.5 Hz, glycerol-C1-H$_a$), 5.13-5.27 (1 H, m, glycerol-C2-H); $^{13}$C NMR (67.5 z, CDCl$_3$) δ$_C$ 170.36, 170.09 (2 CO), 81.6 and 79.58 (2 C≡C), 71.61 (d, J$_{CP}$=7.74 Hz, POCH$_2$CHCH$_2$), 66.35 (d, J$_{CP}$=4.67 Hz, POCH$_2$CH$_2$N(CH$_3$)$_3$), 63.65 (POCH$_2$CHCH$_2$), 63.22 (d, J$_{CP}$=25.2 Hz, POCH$_2$ [glycerol]), 59.33 (d, J$_{CP}$=21.2 Hz, POCH$_2$ [choline]), 54.47 (N(CH$_3$)$_3$), 33.64, 33.50, 32.79, 32.72, 29.56, 29.56, 29.32, 29.21, 29.21, 29.03, 28.92, 28.87, 18.76, 14.45 and 12.46 (2 CH$_3$); m/z (FAB+) 812 ([M+Na]$^+$), 790 ([M+H]$^+$); HRMS: Calculated for C$_{40}$H$_{73}$NO$_8$PS$_2$: 790.451526. Found: 790.453156 ([M+H]$^+$).

1,2-Ditetradecylthioacetoyl-sn-glycero-3-phosphoethanolamine (TTA-PE, 21)

CH$_2$CH$_3$), 1.15-1.41 (44 H, 2 m, 22 CH$_2$), 1.50-1.62 (4 H, m, 2 CH$_2$CH$_3$), 2.58 (4 H, 2 t, J=6.9 Hz, 2 CH$_2$SCH$_2$CO$_2$), 3.05-3.13 (2 H, m, CH$_2$NH$_3$), 3.20 and 3.24 (2 H, 2 s, 2 CH$_2$SCH$_2$CO$_2$), 3.85-3.91 (2 H, m, glycerol-C3-H$_{a,b}$), 3.97-4.05 (2 H, m, CH$_2$CH$_2$NH$_3$), 4.09-4.14 (1H, dd, $^2J$=12.0 Hz, $^3J$=6.4 Hz, glycerol-C1-H$_b$), 4.30-4.35 (1 H, dd, $^2J$=11.8 Hz, $^3J$=2.6 Hz, glycerol-C1-H$_a$), 5.14-5.20 (1 H, m, glycerol-C2-H), 8.20-8.60 (br s, NH$_3$); $^{13}$C NMR (400 MHz, CDCl$_3$) δ$_C$ 170.29, 170.13 (2 CO), 71.28 (d, J$_{CP}$=27.6 Hz, POCH$_2$CHCH$_2$), 63.73 (d, J$_{CP}$=22.0 Hz, POCH$_2$ [glycerol]), 63.25 (POCH$_2$CHCH$_2$), 62.40 (m, POCH$_2$ [choline]), 40.49 (CH$_2$NH$_3$), 33.59, 33.42, 32.81, 32.75, 32.01, 29.81 (14 CH$_2$), 29.46, 29.09, 28.97, 28.93, 22.77 and 14.19.

1,2-Di(Cis-tetradec-6-enylthioacetoyl)-sn-glycero-3-phosphoethanolamine (dTTA-PE, 22)

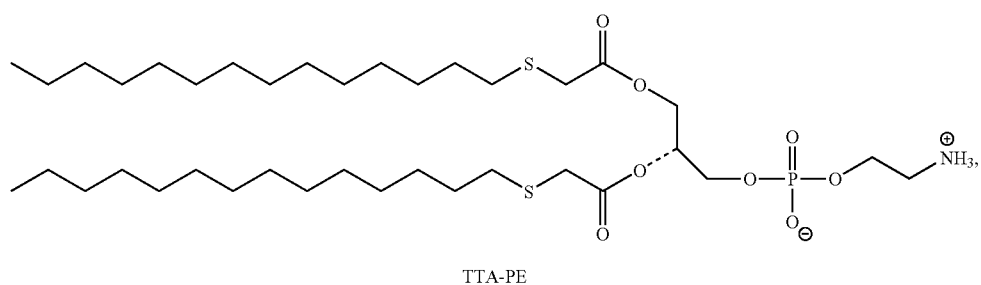

TTA-PE

A solution of ethanolamine (91 μl, 1.50 mmol, 6 eq.) in a 100 mM NaOAc/50 mM CaCl$_2$ buffer (0.625 ml) at pH 6.5 (pH adjusted with acetic acid), was added to a stirred solution of 18 (135 mg, 0.169 mmol, 1 eq.) in CHCl$_3$ (5 ml) at 30° C. To this biphasic system was added PLD (310 units in 440 μl of the aforementioned buffer, pH 6.5), and the reaction mixture was allowed to stir at 30° C. for 3 h. Further PLD (35 units) was added. After 10 h, the aqueous phase was diluted to 15 ml, and the crude organic material was extracted by washing with CHCl$_3$:MeOH, 2:1 (30 ml×3). The organic layers were combined and washed with H$_2$O (15 ml), then concentrated in vacuo, and subjected to SiO$_2$ flash column chromatography [CH$_2$Cl$_2$:MeOH:H$_2$O, 77.54:20.23:2.23] to purify. This afforded the title compound, 21, as a very pale-yellow, waxy solid (120 mg, 94%): R$_f$ 0.32 [CH$_2$Cl$_2$:MeOH:H$_2$O, 65:25:4]; $^1$H NMR (400 MHz, CDCl$_3$) δ$_H$ 0.85 (6 H, t, J=6.9 Hz, 2

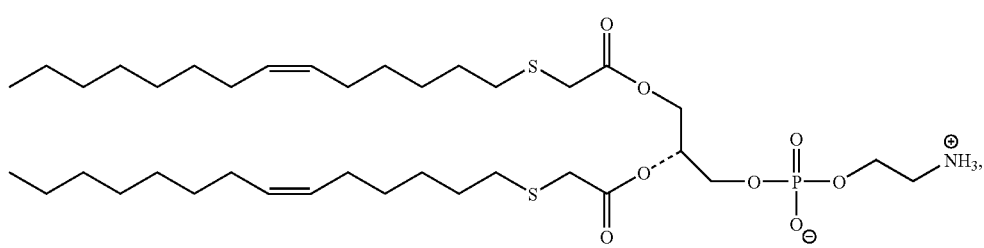

dTTA-PE

A solution of ethanolamine (91 μl, 1.50 mmol, 6 eq.) in a 100 mM NaOAc/50 mM CaCl$_2$ buffer (0.625 ml) at pH 6.5 (pH adjusted with acetic acid), was added to a stirred solution of 19 (188 mg, 0.237 mmol, 1 eq.) in CHCl$_3$ (5 ml) at 30° C. To this bipbasic system was added PLD (250 units in 440 μl of the aforementioned buffer, pH 6.5), and the reaction mixture was allowed to stir at 30° C. for 3 h. Further PLD (35 units) was added. After 10 h, the aqueous phase was diluted to 15 ml, and the crude organic material was extracted by washing with CHCl$_3$:MeOH, 2:1 (30 ml×3). The organic layers were combined and washed with H$_2$O (15 ml), then concentrated in vacuo, and subjected to SiO$_2$ flash column chromatography [CH$_2$Cl$_2$:MeOH:H$_2$O, 77.54:20.23:2.23] to purify. This afforded the title compound, 22, as a very pale-yellow, waxy solid (158 mg, 89%): R$_f$ 0.32 [CH$_2$Cl$_2$:MeOH:H$_2$O, 65:25:4]; $^1$H NMR (400 MHz, CDCl$_3$) $\delta_H$ 0.85 (6 H, t, J=6.9 Hz, 2 CH$_2$CH$_3$), 1.15-1.41 (36 H, 2 m, 18 CH$_2$), 1.50-1.62 (4 H, m, 2 CH$_2$CH$_3$), 1.90-1.21 (8 H, m, 2 CH$_2$CH=CHCH$_2$), 2.58 (4 H, 2 t, J=6.9 Hz, 2 CH$_2$SCH$_2$CO$_2$), 3.05-3.13 (2 H, m, CH$_2$NH$_3$), 3.20 and 3.24 (2 H, 2 s, 2 CH$_2$SCH$_2$CO$_2$), 9 Hz, 2 CH$_2$SCH$_2$CO$_2$), 3.05-3.13 (2 H, m, CH$_2$NH$_3$), 3.20 and 3.24 (2 H, 2 s, 2 CH$_2$SCH$_2$CO$_2$), 3.85-3.91 (2 H, m, glycerol-C3-H$_{a,b}$), 3.97-4.05 (2 H, m, CH$_2$CH$_2$NH$_3$), 4.09-4.14 (1H, dd, $^2$J=12.0 Hz, $^3$J=6.4 Hz, glycerol-C1-H$_b$), 4.30-4.35 (1 H, dd, $^2$J=11.8 Hz, $^3$J=2.6 Hz, glycerol-C1-H$_a$), 5.14-5.20 (1 H, m, glycerol-C2-H), 5.22-5.32 (4 H, m, 2 CH=CH), 8.20-8.60 (br s, NH$_3$); $^{13}$C NMR (400 MHz, CDCl$_3$) $\delta_C$ 170.28, 170.11 (2 CO), 130.29, 129.41 (2 C=C), 71.28 (d, J$_{CP}$=27.6 Hz, POCH$_2$CHCH$_2$), 63.73 (m, POCH$_2$ [glycerol]), 63.25 (POCH$_2$CHCH$_2$), 62.40 (m, POCH$_2$ [choline]), 40.49 (CH$_2$NH$_3$), 33.58, 33.41, 32.72, 32.67, 31.94, 29.82, 29.46, 29.35, 29.31, 28.99, 28.55, 28.52, 27.32, 27.16, 22.75 and 14.18 (2 CH$_3$); m/z (FAB+) 748 ([M+Na]$^+$), 770 ([M+H]$^+$); HRMS: Calculated for C$_{37}$H$_{67}$NO$_8$PS$_2$:748.404576. Found: 748.404526 ([M+H]$^+$).

1,2-Di(tetradec-11-ynylthioacetoyl)-sn-glycero-3-phosphoethanolamine (tTTA-PE, 23) ([M+H]$^+$).

the aforementioned buffer, pH 6.5), and the reaction mixture was allowed to stir at 30° C. for 3 h. Further PLD (35 units) was added. After 10 h, the aqueous phase was diluted to 15 ml, and the crude organic material was extracted by washing with CHCl$_3$:MeOH, 2:1 (30 ml×3). The organic layers were combined and washed with H$_2$O (15 ml), then concentrated in vacuo, and subjected to SiO$_2$ flash column chromatography [CH$_2$Cl$_2$:MeOH:H$_2$O, 77.54:20.23:2.23] to purify. This afforded the title compound, 23, as a very pale-yellow, waxy solid (151 mg, 86%): R$_f$ 0.32 [CH$_2$Cl$_2$:MeOH:H$_2$O, 65:25:4]; $^1$H NMR (400 MHz, CDCl$_3$) $\delta_H$ 1.09 (6 H, t, J=6.9 Hz, 2 CH$_2$CH$_3$), 1.15-1.60 (32 H, m, 8 CH$_2$), 2.0-2.17 (CH$_2$C=CCH$_2$), 2.56 (4 H, 2×t, J=7.2 Hz, 2 CH$_2$SCH$_2$CO$_2$), 3.05-3.13 (2H, m, CH$_2$NH$_3$), 3.20 and 3.23 (2×1 H, 2 s, 2 CH$_2$SCH$_2$CO$_2$), 3.85-3.91 (2 H, m, glycerol-C3-H$_{a,b}$), 3.97-4.05 (2 H, m, CH$_2$CH$_2$NH$_3$), 4.09-4.14 (1 H, dd, $^2$J=12.0 Hz, $^3$J=6.4 Hz, glycerol-C1-H$_b$), 4.30-4.35 (1 H, m, glycerol-C1-H$_a$), 5.14-5.20 (1 H, m, glycerol-C2-H), 8.20-8.60 (br s, NH$_3$); $^{13}$C NMR (67.5 MHz, CDCl$_3$) $\delta_C$ 170.27, 170.11 (2 CO), 81.60 and 79.58 (2 C=C), 71.28 (d, J$_{CP}$=27.6 Hz, POCH$_2$CHCH$_2$), 63.70 (d, J$_{CP}$=22.0 Hz, POCH$_2$ [glycerol]), 63.22 (POCH$_2$CHCH$_2$), 62.35 (m, POCH$_2$ [choline]), 40.47 (CH$_2$NH$_3$), 33.58, 33.41, 32.78, 32.72, 29.61 (3 CH$_2$), 29.56, 29.37, 29.23 (3 CH$_2$), 29.04, 28.95 (2 CH$_2$), 28.88, 18.79, 14.45 and 12.47 (2 CH$_3$).

1,2,3-Tritetradecylthioacetoyl-sn-glycerol (TTA-TAG, 24)

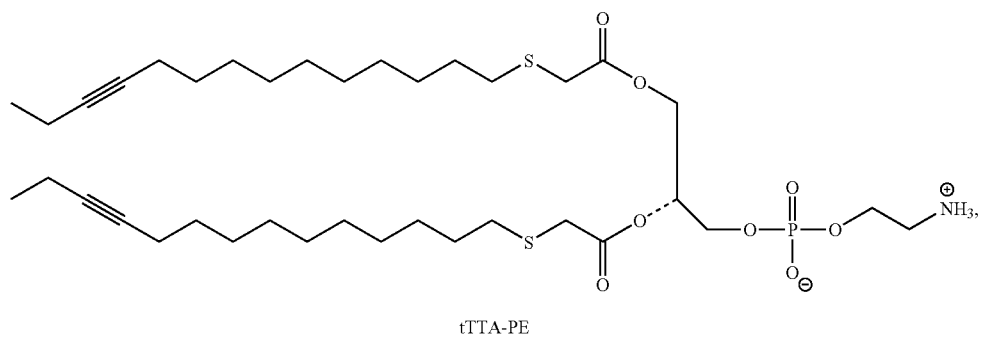

tTTA-PE

A solution of ethanolamine (91 μl, 1.50 mmol, 6 eq.) in a 100 mM NaOAc/50 mM CaCl$_2$ buffer (0.625 ml) at pH 6.5 (pH adjusted with acetic acid), was added to a stirred solution of 20 (185 mg, 0.234 mmol, 1 eq.) in CHCl$_3$ (5 ml) at 30° C. To this biphasic system was added PLD (250 units in 440 μl of

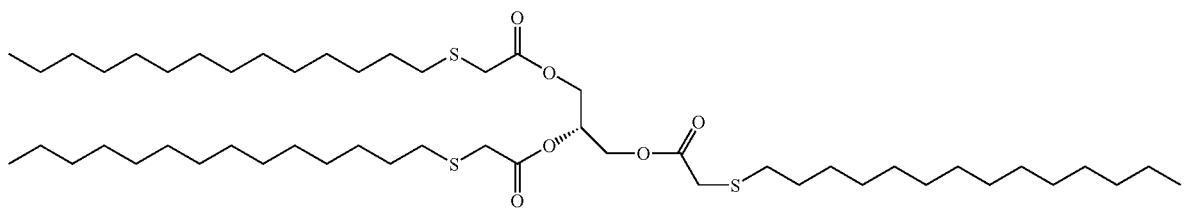

Dimethylaminopyridine (2.08 g, 17.00 mmol), 2-(1H-benzotriazol-1-yl)-N,N,N',N'-teramethyluroniumhexafluorophosphate (HBTU; 6.45 g, 17.00 mmol) and glycerol (0.45 g, 4.95 mmol) were added to a stirred solution of TTA 3 (5.00 g, 17.00 mmol) in anhydrous $CHCl_3$ (120 ml) under a $N_2$ atmosphere. The resultant mixture was stirred at room temperature for 24 h. The crude reaction mixture was washed with 7% citric acid and the organic phase was dried over $MgSO_4$. The residual solid was purified by $SiO_2$ flash column chromatography [$Et_2O$: Hexane, 1:5], to afford TTA-TAG 24 as a white solid (3.80 g, 85%): $R_f$ 0.35 [$Et_2O$: Hexane, 1:5]; $^1H$ NMR (400 MHz, $CDCl_3$) δ 0.88 (9H, t, J=6.0 Hz, 3 $CH_2CH_3$), 1.23-1.41 (66 H, 2 m, 33 $CH_2$), 1.55-1.63 (6 H, m, 3 $CH_2CH_3$), 2.62 (4 H, t, J=7.6, $CH_2SCH_2CO_2$), 2.63 (4 H, t, J=7.6, $CH_2SCH_2CO_2$), 3.15 (6 H, s, $CH_2SCH_2CO_2$), 4.19 (2 H, dd, $^2J$=12.0 Hz, $^3J$=6.0 Hz, glycerol-C1-$H_a$ and glycerol-C3-$H_a$), 4.32 (2 H, dd, $^2J$=12.0 Hz, $^3J$=4.4 Hz, glycerol-C1-$H_b$ and glycerol-C3-$H_b$), 5.30-5.35 (1 H, m, glycerol-C2-H); $^{13}C$ NMR (100 MHz, $CDCl_3$) δ 170.08, 169.77 (3 CO), 69.69 (glycerol-C2), 62.66 (glycerol-C1 and glycerol-C3), 33.45, 33.34, 32.81, 32.77, 31.97, 29.73, 29.74, 29.66, 29.58, 29.41, 29.28, 29.0, 28.84, 28.81, 22.74, 14.17 (3 $CH_3$); m/z (ESI) 925 ($[M+Na]^+$).

2.3.4 Biological Experimental

Methods
Animals and Treatments

Male Wistar Charles River rats weighing 200-250 g at the start of the experiment were housed in metal wire cages in a temperature (22±1° C.) and light-controlled (light from 7.00 a.m. to 7.00 p.m.) room. They were given free access to chow and water. They were fed a Standard Laboratory Rat Chow R-34-EWOS-ALAB (EWOS Sweden) grower rat maintenance chow. Two rats were housed per cage. The animals were acclimatized for at least 5 days before the start of the experiments. Weight gain and food intake were recorded daily. TTA and esterified TFAs (1,2-Di(1,2-Di(tetradecylthioacetoyl)-sn -glycero-3-phosphocholine (TTA-PC) and Glyceryl 1,2,3-Tri(tetradecylthioacetate) (triacylglycerol) (TTA-TAG)) were suspended in 0.5% carboxymethylcellulose (CMC) and administered by by gastric intubation in a final volume of 0.8-1.2 ml once a day for 6 days.

At the end of the experiments the animals were anaesthetized with Fluorane (0.4 ml/100 g body weight) and cardiac puncture was performed to obtain blood samples in EDTA containing vacutainers. Plasma was prepared and triacylglycerol and cholesterol were measured using the Monotest enzymatic kit (Boehringer Mannheim, Germany).

Preparation of Post-Nuclear and Mitochondrial Fractions and Measurement of Enzyme Activities Freshly isolated livers from individual male wistar rats, were homogenised in ice-cold sucrose buffer (0.25 M sucrose, 10 mM HEPES (pH 7.4) and 2 mM EDTA). Post-nuclear and mitochondrial fractions were prepared using preparative differential centrifugation according to DeDuve et al.[13] Modifications, purity and yield were as described in literature[14]. Acid soluble products were measured in post-nuclear fractions, using [1-$^{14}C$]-palmitoyl-CoA (Radiochemical Centre, Amersham, England) as substrates as described in literature.[15] Carnitine palmitoyltransferase-II activities were measured in the mitochondrial fraction essentially as described by Bremer[16] and 3-hydroxy-3-methylglutharyl-CoA synthase was measured according to Clinkenbeard et al.[17] in the post-nuclear fraction. Fatty acyl-CoA oxidase was measured in the post-nuclear fraction by the coupled assay described by Small et al.[18] The production of hydrogen peroxide was measured by monitoring the increase in dichlorofluorescein absorbance in the presence of palmitoyl-CoA.

Formulation and Administration of Liposomes.

General procedures. 1,2-Dimyristoyl-sn-glycero-3-phosphocholine (DMPC) and stearic acid (SA) were purchased from Sigma-Aldrich. Tetradecylthioacetic acid (TTA) and 1,2-ditetradecylthioacetoyl-sn-glycero-3-phosphocholine (TTA-PC) were synthesised in our Laboratory. Stock solutions of the lipids (5 mg/ml) were prepared in dichloromethane and stored at −20° C. Dichloromethane was used freshly distilled and PBS (10 mM Phosphate buffer, 150 mM NaCl, pH 7.4) was used for liposome hydration.

Preparation of liposomes. The relevant lipid mixture in dichloromethane was dried as a thin layer in a 50 ml round-bottom flask. PBS was added to the lipid film and the mixture was then shaken for 10 min in a water bath at 40-50° C. The liposome suspension obtained was sonicated for 5 min. Differential scanning calorimetry (DSC). Thermograms were obtained using a VP-DSC Microcalorimeter (MicroCal™ Incorporated), at a heating rate of 1° C./min from 5° C. to 60° C. The phase transition temperature ($T_c$) was determined based on the peak top temperature.

Photon correlation spectroscopy (PCS). Particle sizes were measured on an N4 plus MD submicron particle analyser (Beckman Coulter, High Wycombe, Buckinghamshire, U.K.). All measurements were performed at 20° C. and recorded at 90° C., with an equilibration time of 1 min and individual run times of 300 s. The refractive index of the buffer was set to 1.333. Unimodal analysis was used throughout to calculate the mean particle size and standard distribution. Zeta potential (ZP). Zeta potentials were measured using surface charge electrophoresis on a Delsa 440 SX (Beckman Coulter, High Wycombe, Buckinghamshire, U.K.).

TTA Liposomes

TTA was formulated as a DMPC/TTA liposome system. Different molar ratios of DMPC:TTA liposomes were analysed and characterised The final formulation used for the intravenous injection of TTA was DMPC/TTA (1:1) in PBS. The concentration of TTA prepared and injected is shown in Table 7.

TABLE 7

| Liposome | TTA cc. (mg/ml) | Total lipid cc. (mg/ml) | PCS (nm) |
| --- | --- | --- | --- |
| TTA | 8.94 | 28.64 | 265.3 ± 114.3 |

TTA-PC liposomes

TTA-PC liposomes were initially formulated from TTA-PC alone, but it was found that the highest concentration that could be achieved was 2.5 mg/ml of lipid. In order to reach higher concentrations, TTA-PC liposomes were stabilized with stearic acid. The final formulation used for the intravenous injection of TTA-PC was TTA-PC:SA (2:1) in PBS. The concentration of TTA-PC prepared and injected is shown in Table 8. These doses were calculated in relation to amount of latent TTA present in TTA-PC.

TABLE 8

| Liposome | TTA-PC cc. (mg/ml) | Total lipid cc. (mg/ml) | PCS (nm) |
|---|---|---|---|
| TTA-PC | 12.5 | 14.72 | 209.1 ± 84.6 |

The liposomes were suspended in phosphate buffered saline in the concentrations indicated and the solution sonicated before use. Non-esterified TTA (10 mmoles/L) was dissolved in 200 mg/ml albumin injection solution ("Qctapharma") after dissolution in equimolar amounts of NaOH. Final pH 7.0. Liposomes or TTA solution (1 ml) was injected trough the tail vein after the rats had been anaesthetized with Fluorane (0.4 ml/100 g body weight). The rats were killed as described above.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims

REFERENCES

1a. WO-A-01/68582 (PCT/NO01/00082)
1b. WO-A-99/58121 (PCT/N099/00135)
1c. WO-A-99/58122 (PCT/NO99/00136)
1d. WO-A-99/58123 (PCT/N099/00149)
2. Berg, R. K. and Hvattuu, E.; *Pharmac. Ther.* (1994), 61, 345.
3. Skrede, S. et al; *Biochim. Biophys. Acta* (1997), 1344, 115.
4. EP-A-0345038
5. WO-A-97/03663 (PCT/N095/00195)
6. WO-A-02/03983 (PCT/NO01/00301)
7. Horiike, M; Masaru, T. and Hirano, C.; *Agric. Biol. Chem.*, (1978), 42(10), 1963.
8. Skarma, A.; Chattopadhyay, J.; *J. Org Chem.*, (1998), 63, 6128.
9. Jayasuriya, N.; Bosak, S.; Regan, S. L.; *J. Am. Chem. Soc.*, (1990), 112, 5844.
10. A. Hermetter and F. Paltauf; *Chemistry and Physics of Lipids*, (1981), 28, 111-115.
11. Wang, P., Schuster, M. Wang, Y. F., Wong, C. H. *J. Am. Chem Soc.* (1993), 115, 10487-10491.
12. Bestmann and Gunawarden; *Synthesis*, (1992), 1239.
13. De Duve, C., et al., Biochem. J., 60, 604-617 1955.
14. Garras, A., et al., Biochim. Biophys. Acta, 1255, 154-160 1995.
15. Willumsen, N., et al., J. Lipid Res., 34, 13-22 1993.
16. Bremer, J., Biochim. Biophys. Acta, 665, 628-631 1981.
17. Clinkenbeard, K. D., et al., J. Biol. Chem, 250, 3108-3116 1975.
18. Small, G M et al. Biochem. J. 227, 205-210, 1985.

The invention claimed is:
1. A compound chosen from

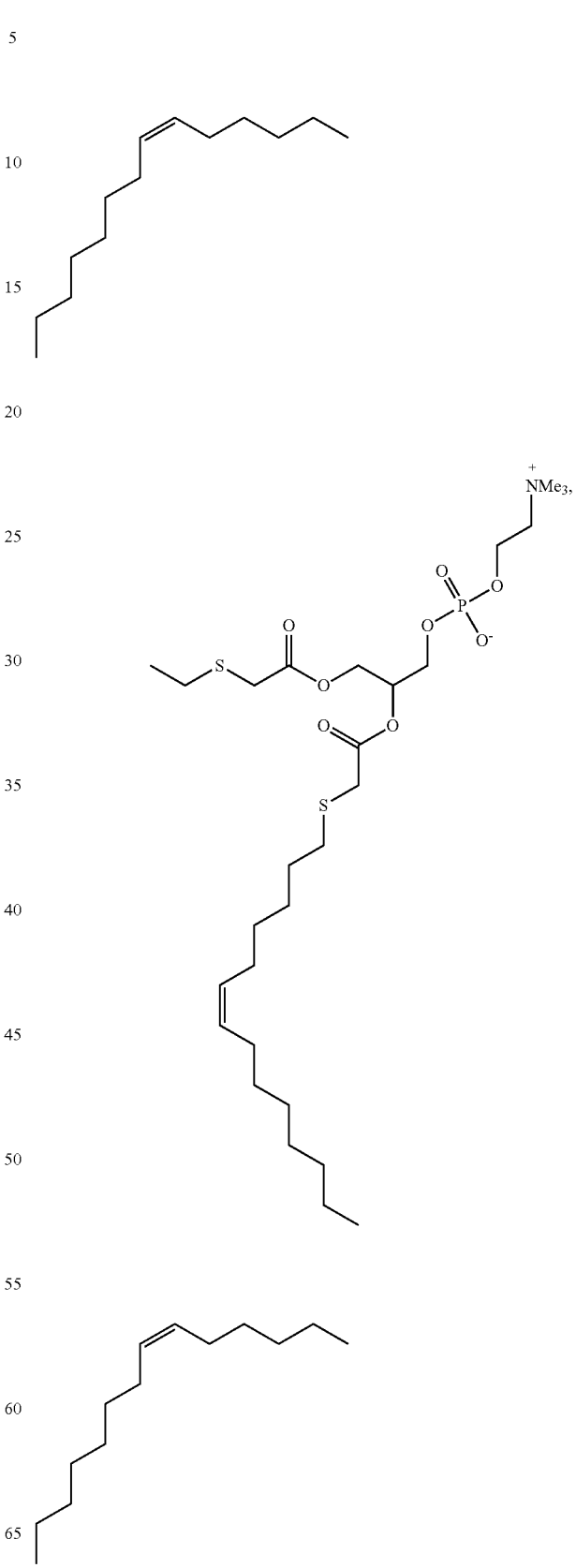

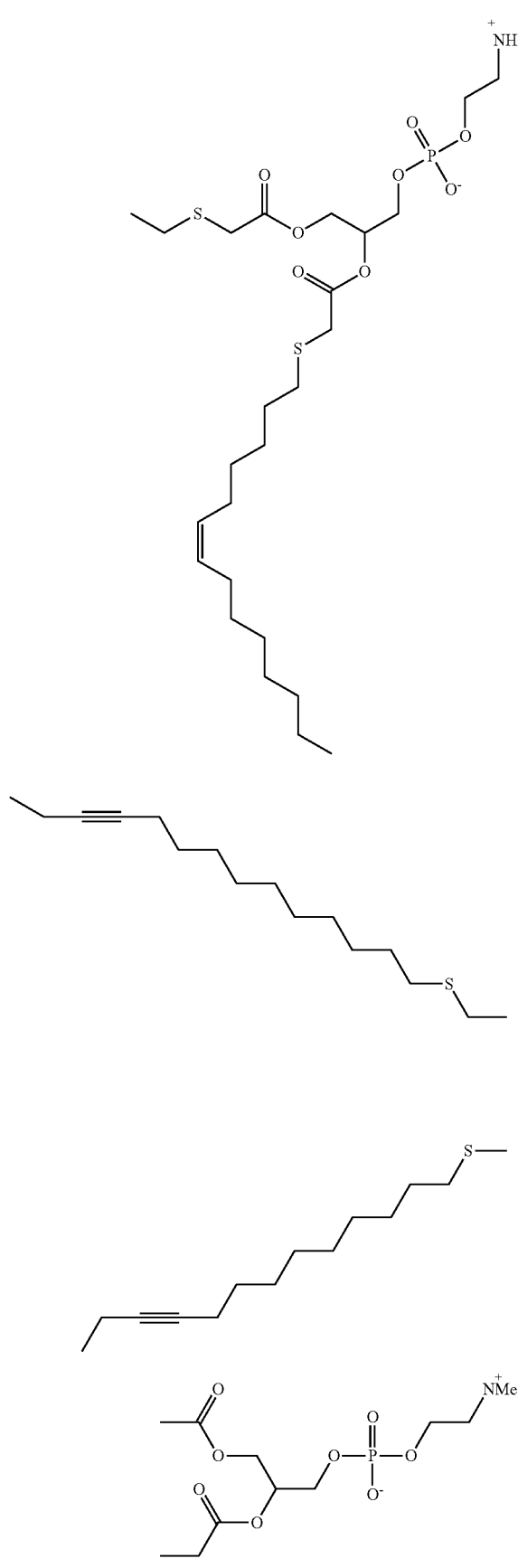
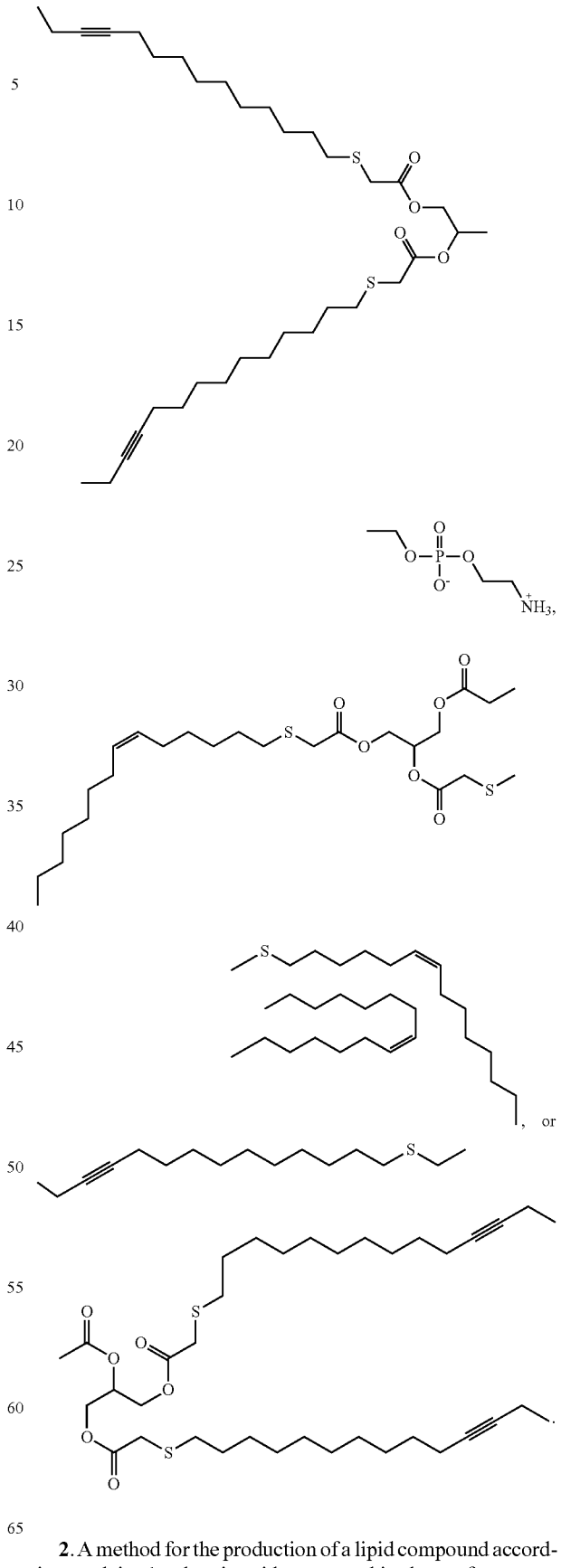
2. A method for the production of a lipid compound according to claim 1, wherein said compound is chosen from

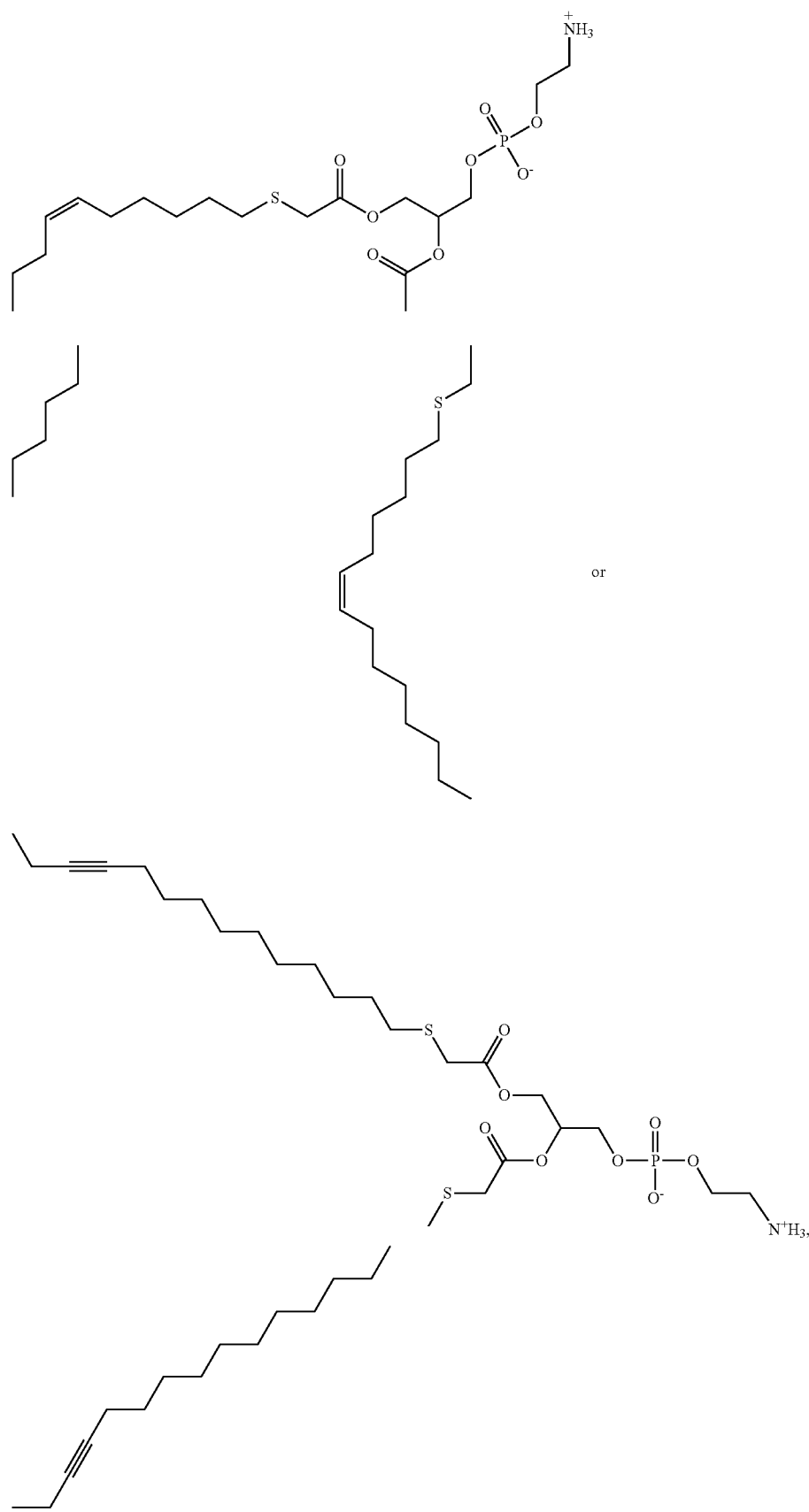

the method comprising:
(a) combining an unsaturated analogue of tetradecylthio-acetic acid (TTA 3) chosen from dTTA 4 or tTTA 5 with N,N'-carbonyldiimidazolide (CDI) to form an imidazolide;
(b) combining the imidazolide of step (a) with sn-Glycero-3-phosphocholine (GPC) cadmium (II) adduct (GPC.CdC$_2$) to form a phosphatidylcholine derivative; and
(c) subjecting the phosphatidylcholine derivative of step (b) to enzymatic transphosphatidylation to form said compound.

3. A method for the production of a lipid compound according to claim 1, wherein said compound is chosen from

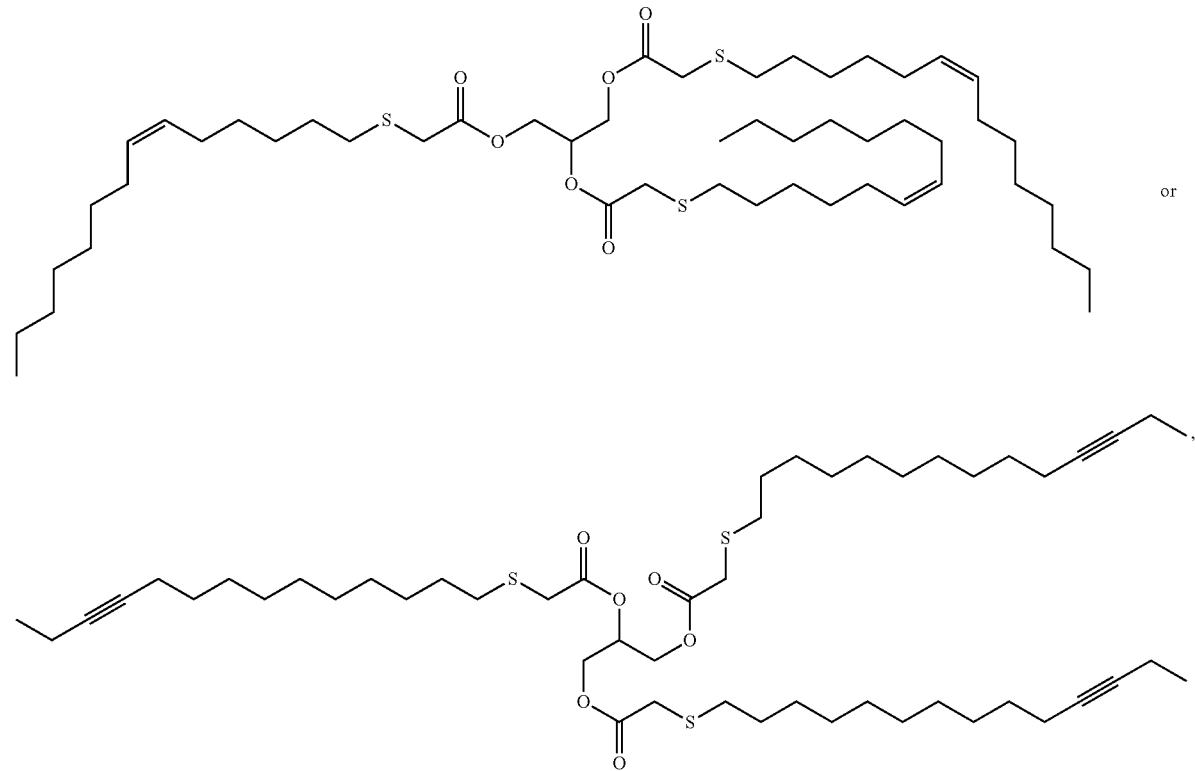

or the method comprising combining an unsaturated analogue of tetradecylthioacetic acid (TTA 3) chosen from dTTA 4 or tTTA 5 with glycerol.

4. A combination comprising a liposome and a compound according to claim 1.

5. A method for the production of a lipid compound according to claim 1, wherein said compound is chosen from

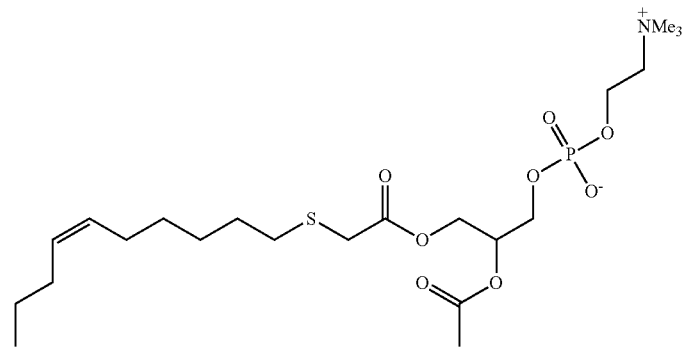

-continued

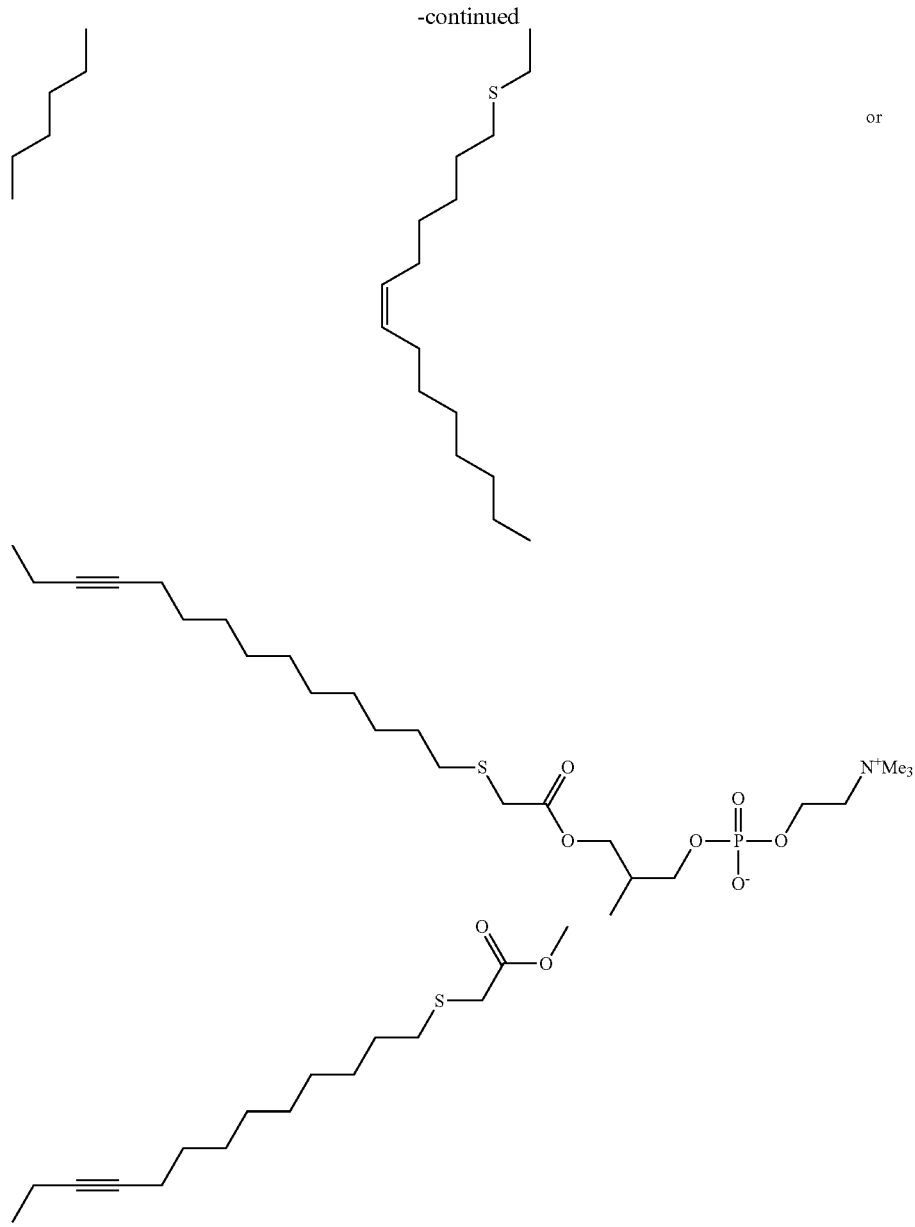

the method comprising:
(a) combining an unsaturated analogue of tetradecylthioacetic acid (TTA 3) chosen from dTTA 4 or tTTA 5 with N,N'-carbonyldiimidazolide (CDI) to form an imidazolide; and
(b) combining the imidazolide of step (a) with sn-Glycero-3-phosphocholine (GPC) cadmium (II) adduct (GPC.CdCl$_2$) to form said compound.

6. A cosmetic formulation comprising a lipid compound according to claim 1.

7. A pharmaceutical composition comprising a compound according to claim 1.

8. A method of treating a condition chosen from syndrome X, obesity or an overweight condition, hypertension, fatty liver, diabetes, hyperglycaemia, hyperinsulinemia, insulin resistance, hyperlipidemia, hypercholesterolemia, hypertriglyceridemia (HTG), and stenosis, comprising administering to a subject in need thereof an effective amount of a compound according to claim 1 or a pharmaceutically acceptable salt thereof.

9. The method according to claim 8, for producing weight loss or a reduction of fat mass in a human or non-human animal in need thereof.

10. A method for the treatment of inflammatory disorders, comprising administering to a subject in need thereof an effective amount of a compound according to claim 1 or a pharmaceutically acceptable salt thereof.

11. A method of lowering concentration of cholesterol and triglycerides in the blood of mammals and/or inhibiting the oxidative modification of low density lipoprotein, comprising administering to a subject in need thereof an effective amount of a compound according to claim 1 or a pharmaceutically acceptable salt thereof.

12. A method for producing weight loss or a reduction of the fat mass in a human or non-human animal in need thereof, comprising administering thereto an effective amount of a compound according to claim 1 or a pharmaceutically acceptable salt thereof.

13. A method for the modification of the fat distribution and content of animals, comprising administering to a subject in need thereof an effective amount of a compound according to claim 1 or a pharmaceutically acceptable salt thereof.

14. A method of inhibiting the growth of tumours, comprising administering to a subject in need thereof an effective amount of a compound according to claim 1 or a pharmaceutically acceptable salt thereof.

15. A method for the treatment or inhibition of primary and secondary metastatic neoplasms, comprising administering to a subject in need thereof an effective amount of a compound according to claim 1 or a pharmaceutically acceptable salt thereof.

16. A method for the treatment of proliferative skin disorders, comprising administering to a subject in need thereof an effective amount of a compound according to claim 1 or a pharmaceutically acceptable salt thereof.

17. A method for the inhibition of proliferation or induction of differentiation of keratinocytes, comprising administering to a subject in need thereof an effective amount of a compound according to claim 1 or a pharmaceutically acceptable salt thereof.

18. A method for the treatment of inflammatory disorders, comprising administering to a subject in need thereof an effective amount of a compound according to claim 1 or a pharmaceutically acceptable salt thereof.

19. A method for enhancing the endogenous production of interleukin-10 (IL-10) in mammalian cells or tissues, comprising administering to a subject in need thereof an effective amount of a compound according to claim 1 or a pharmaceutically acceptable salt thereof.

20. A method for suppression of the endogenous production of interleukin-2 (IL-2) in mammalian cells or tissues, comprising administering to a subject in need thereof an effective amount of a compound according to claim 1 or a pharmaceutically acceptable salt thereof.

21. A method for the inhibition of proliferation of stimulated peripheral mononuclear cells (PBMC), comprising administering to a subject in need thereof an effective amount of a compound according to claim 1 or a pharmaceutically acceptable salt thereof.

22. The pharmaceutical composition according to claim 7, admixed with at least one of a pharmaceutically acceptable carrier, diluent, excipient, or adjuvant.

23. A topically administrable pharmaceutical composition according to claim 22.

24. A parenterally administrable pharmaceutical composition according to claim 22.

25. An intravenously administrable pharmaceutical composition according to claim 22.

* * * * *